(12) United States Patent
Ginn et al.

(10) Patent No.: US 9,579,091 B2
(45) Date of Patent: *Feb. 28, 2017

(54) CLOSURE SYSTEM AND METHODS OF USE

(75) Inventors: Richard S. Ginn, Gilroy, CA (US);
William N. Aldrich, Napa, CA (US);
W. Martin Belef, San Jose, CA (US);
Steven N. Roe, San Mateo, CA (US);
Michael T. Carley, San Jose, CA (US);
Ronald J. Jabba, Redwood City, CA (US); Stephen M. Salmon, Napa, CA (US); Anthony Pantages, San Jose, CA (US); Javier Sagastegui, Castro Valley, CA (US); Janina Sagastegui, legal representative, Wroclaw (PL)

(73) Assignee: INTEGRATED VASCULAR SYSTEMS, INC., Redwood City, CA (US)

(*) Notice: Subject to any disclaimer, the term of this patent is extended or adjusted under 35 U.S.C. 154(b) by 913 days.

This patent is subject to a terminal disclaimer.

(21) Appl. No.: 11/396,731

(22) Filed: Apr. 3, 2006

(65) Prior Publication Data

US 2006/0287674 A1 Dec. 21, 2006

Related U.S. Application Data

(63) Continuation-in-part of application No. 10/264,306, filed on Oct. 3, 2002, now Pat. No. 7,901,428, which
(Continued)

(51) Int. Cl.
*A61B 17/08* (2006.01)
*A61B 17/00* (2006.01)
*A61B 17/064* (2006.01)

(52) U.S. Cl.
CPC ........ *A61B 17/0057* (2013.01); *A61B 17/083* (2013.01); *A61B 17/064* (2013.01);
(Continued)

(58) Field of Classification Search
CPC ..... A61B 17/064; A61B 17/08; A61B 17/083; A61B 17/0057; A61B 17/0644;
(Continued)

(56) References Cited

U.S. PATENT DOCUMENTS 287,046 A 10/1883 Norton
438,400 A 10/1890 Brennen
(Continued)

FOREIGN PATENT DOCUMENTS

AU 2003297432 7/2004
CA 2 339 060 2/2000
(Continued)

OTHER PUBLICATIONS

"Hand tool for forming telephone connections—comprises pliers with reciprocably driven ram crimping clip around conductors against anvil", Derwent-ACC-No. 1978-B8090A.
(Continued)

*Primary Examiner* — Alexander Orkin
(74) *Attorney, Agent, or Firm* — Workman Nydegger; Randy Shen

(57) ABSTRACT

A closure system and methods of use are provided for use in sealing an opening in a body tissue, such as a vascular puncture site. A method of closing the opening in the body tissue can be performed with the closure system having a closure clip. The method can include positioning the closure clip in a first closure clip position adjacent to the opening in the body tissue such that a plurality of spikes of the closure clip are inserted into the tissue at a location outward from a central axis of the opening. Subsequently, the closure clip can be positioned in a second closure clip position such that the plurality of spikes are pulled inward toward the central
(Continued)

axis of the opening so as to pull the tissue between the opening and each of the spikes together and close the opening.

24 Claims, 37 Drawing Sheets

Related U.S. Application Data is a continuation of application No. 09/546,998, filed on Apr. 11, 2000, now Pat. No. 6,461,364, which is a continuation-in-part of application No. 09/478,179, filed on Jan. 5, 2000, now Pat. No. 6,197,042, said application No. 11/396,731 is a continuation-in-part of application No. 11/198,811, filed on Aug. 4, 2005, now Pat. No. 7,828,817, which is a continuation of application No. 10/081,723, filed on Feb. 21, 2002, now Pat. No. 6,942,674, which is a continuation-in-part of application No. 09/732,835, filed on Dec. 7, 2000, now Pat. No. 6,780,197, which is a continuation-in-part of application No. 09/610,238, filed on Jul. 5, 2000, now Pat. No. 6,391,048, which is a continuation-in-part of application No. 09/478,179, filed on Jan. 5, 2000, now Pat. No. 6,197,042, application No. 11/396,731, which is a continuation-in-part of application No. 10/006,400, filed on Nov. 30, 2001, now Pat. No. 7,842,068, which is a continuation-in-part of application No. 09/732,835, filed on Dec. 7, 2000, now Pat. No. 6,780,197, which is a continuation-in-part of application No. 09/610,238, filed on Jul. 5, 2000, now Pat. No. 6,391,048, which is a continuation-in-part of application No. 09/478, 179, filed on Jan. 5, 2000, now Pat. No. 6,197,042, application No. 11/396,731, which is a continuation-in-part of application No. 10/147,774, filed on May 17, 2002, now Pat. No. 7,931,669, which is a continuation-in-part of application No. 09/610,238, filed on Jul. 5, 2000, now Pat. No. 6,391,048, which is a continuation-in-part of application No. 09/478,179, filed on Jan. 5, 2000, now Pat. No. 6,197,042.

(52) U.S. Cl.
CPC . *A61B 17/0643* (2013.01); *A61B 2017/00637* (2013.01); *A61B 2017/00654* (2013.01); *A61B 2017/00668* (2013.01); *A61B 2017/00672* (2013.01); *A61B 2017/00862* (2013.01); *A61B 2017/0641* (2013.01)

(58) Field of Classification Search
CPC .......... A61B 17/0643; A61B 2017/081; A61B 2017/088; A61B 2017/0641; A61B 2017/0645; A61B 2017/00654; A61B 2017/00637; A61B 2017/00575
USPC ........ 606/213, 215, 216, 155, 157, 219, 221
See application file for complete search history.

(56) References Cited

U.S. PATENT DOCUMENTS

| | | | |
|---|---|---|---|
| 556,082 A | 3/1896 | Boeddinghaus | |
| 1,088,393 A | 2/1914 | Backus | |
| 1,123,290 A * | 1/1915 | Herff | 606/221 |
| 1,242,139 A | 10/1917 | Callahan | |
| 1,331,401 A | 2/1920 | Summers | |
| 1,426,111 A | 8/1922 | Sacker | |
| 1,480,935 A | 1/1924 | Gleason | |
| 1,516,990 A | 11/1924 | Silverman | |
| 1,596,004 A | 8/1926 | De Bengoa | |
| 1,647,958 A | 11/1927 | Ciarlante | |
| 1,847,347 A | 3/1932 | Maisto | |
| 1,852,098 A | 4/1932 | Anderson | |
| 1,880,569 A | 10/1932 | Weis | |
| 2,075,508 A | 3/1937 | Davidson | |
| 2,087,074 A | 7/1937 | Tucker | |
| 2,210,061 A | 8/1940 | Caminez | |
| 2,254,620 A | 9/1941 | Miller | |
| 2,316,297 A | 4/1943 | Southerland et al. | |
| 2,371,978 A | 3/1945 | Perham | |
| 2,453,227 A | 11/1948 | James | |
| 2,583,625 A | 1/1952 | Bergan | |
| 2,684,070 A | 7/1954 | Kelsey | |
| 2,755,699 A | 7/1956 | Forster | |
| 2,910,067 A | 10/1959 | White | |
| 2,944,311 A | 7/1960 | Schneckenberger | |
| 2,951,482 A | 9/1960 | Sullivan | |
| 2,969,887 A | 1/1961 | Darmstadt et al. | |
| 3,014,483 A | 12/1961 | McCarthy | |
| 3,015,403 A | 1/1962 | Fuller | |
| 3,113,379 A | 12/1963 | Frank | |
| 3,120,230 A | 2/1964 | Skold | |
| 3,142,878 A | 8/1964 | Santora | |
| 3,209,754 A | 10/1965 | Brown | |
| 3,348,595 A | 10/1967 | Stevens, Jr. | |
| 3,357,070 A | 12/1967 | Sloan | |
| 3,482,428 A | 12/1969 | Kapitanov et al. | |
| 3,494,533 A | 2/1970 | Green et al. | |
| 3,510,923 A | 5/1970 | Blake | |
| 3,513,848 A | 5/1970 | Winston et al. | |
| 3,523,351 A | 8/1970 | Filia | |
| 3,525,340 A | 8/1970 | Gilbert | |
| 3,586,002 A | 6/1971 | Wood | 165/240 |
| 3,604,425 A | 9/1971 | LeRoy | 403/302 |
| 3,618,447 A | 11/1971 | Goins | |
| 3,664,345 A | 5/1972 | Dabbs et al. | |
| 3,677,243 A | 7/1972 | Nerz | 604/161 |
| 3,682,180 A | 8/1972 | McFarlane | |
| 3,732,719 A | 5/1973 | Pallotta | |
| 3,750,650 A | 8/1973 | Ruttgers | |
| 3,753,438 A | 8/1973 | Wood et al. | |
| 3,757,629 A | 9/1973 | Schneider | 411/443 |
| 3,805,337 A | 4/1974 | Branstetter | 24/27 |
| 3,823,719 A | 7/1974 | Cummings | |
| 3,828,791 A | 8/1974 | Santos | |
| 3,831,608 A | 8/1974 | Kletschka et al. | |
| 3,856,016 A | 12/1974 | Davis | |
| 3,874,388 A | 4/1975 | King et al. | |
| 3,908,662 A | 9/1975 | Razgulov et al. | |
| 3,926,194 A | 12/1975 | Greenberg et al. | |
| 3,931,821 A | 1/1976 | Kletschka et al. | |
| 3,939,820 A | 2/1976 | Grayzel | |
| 3,944,114 A | 3/1976 | Coppens | |
| 3,960,147 A | 6/1976 | Murray | |
| 3,976,079 A | 8/1976 | Samuels et al. | |
| 3,985,138 A | 10/1976 | Jarvik | |
| 4,007,743 A | 2/1977 | Blake | |
| 4,014,492 A | 3/1977 | Rothfuss | |
| 4,018,228 A | 4/1977 | Goosen | |
| 4,047,533 A | 9/1977 | Perciaccante et al. | |
| 4,064,881 A | 12/1977 | Meredith | |
| 4,112,944 A | 9/1978 | Williams | |
| 4,153,321 A | 5/1979 | Pombrol | |
| 4,162,673 A | 7/1979 | Patel | |
| 4,169,476 A | 10/1979 | Hiltebrandt | |
| 4,189,808 A | 2/1980 | Brown | |
| 4,192,315 A | 3/1980 | Hilzinger et al. | 606/158 |
| 4,201,215 A | 5/1980 | Crossett et al. | |
| 4,204,541 A | 5/1980 | Kapitanov | |
| 4,207,870 A | 6/1980 | Eldridge | |
| 4,214,587 A | 7/1980 | Sakura, Jr. | |
| 4,215,699 A | 8/1980 | Patel | |
| 4,217,902 A | 8/1980 | March | 606/221 |
| 4,267,995 A | 5/1981 | McMillan | |
| 4,273,129 A | 6/1981 | Boebel | |
| 4,274,415 A | 6/1981 | Kanamoto et al. | |
| 4,278,091 A | 7/1981 | Borzone | |
| 4,287,489 A | 9/1981 | Pinkham | |

(56) References Cited

U.S. PATENT DOCUMENTS

| | | | |
|---|---|---|---|
| 4,291,698 A | 9/1981 | Fuchs et al. | |
| 4,317,445 A | 3/1982 | Robinson | |
| 4,317,451 A | 3/1982 | Cerwin et al. | |
| 4,318,401 A | 3/1982 | Zimmerman | |
| 4,327,485 A | 5/1982 | Rix | |
| 4,345,606 A | 8/1982 | Littleford | 607/122 |
| 4,359,052 A | 11/1982 | Staub | |
| 4,368,736 A | 1/1983 | Kaster | |
| 4,387,489 A | 6/1983 | Dudek | |
| 4,396,139 A | 8/1983 | Hall et al. | 227/19 |
| 4,400,879 A | 8/1983 | Hildreth | |
| 4,407,286 A | 10/1983 | Noiles et al. | |
| 4,411,654 A | 10/1983 | Boarini et al. | 604/165.4 |
| 4,412,832 A | 11/1983 | Kling et al. | 604/164.05 |
| 4,428,376 A | 1/1984 | Mericle | |
| 4,440,170 A | 4/1984 | Golden et al. | |
| 4,449,531 A | 5/1984 | Cerwin et al. | |
| 4,475,544 A | 10/1984 | Reis | |
| 4,480,356 A | 11/1984 | Martin | |
| 4,485,816 A | 12/1984 | Krumme | 606/219 |
| RE31,855 E | 3/1985 | Osborne | 604/161 |
| 4,505,273 A | 3/1985 | Braun et al. | |
| 4,505,274 A | 3/1985 | Speelman | 606/221 |
| 4,523,591 A | 6/1985 | Kaplan et al. | |
| 4,523,695 A | 6/1985 | Braun et al. | |
| 4,525,157 A | 6/1985 | Valaincourt | |
| 4,526,174 A | 7/1985 | Froehlich | |
| 4,577,635 A | 3/1986 | Meredith | |
| 4,586,503 A | 5/1986 | Kirsch et al. | 606/155 |
| 4,592,498 A | 6/1986 | Braun et al. | |
| 4,596,559 A | 6/1986 | Fleischhacker | |
| 4,607,638 A | 8/1986 | Crainich | |
| 4,610,251 A | 9/1986 | Kumar | |
| 4,610,252 A | 9/1986 | Catalano | |
| 4,635,634 A | 1/1987 | Santos | |
| 4,644,956 A | 2/1987 | Morgenstern | |
| 4,651,737 A | 3/1987 | Deniega | |
| 4,664,305 A | 5/1987 | Blake, III et al. | |
| 4,665,906 A | 5/1987 | Jervis | |
| 4,667,675 A | 5/1987 | Davis | |
| 4,683,895 A | 8/1987 | Pohndorf | |
| 4,687,469 A | 8/1987 | Osypka | 604/161 |
| 4,693,249 A | 9/1987 | Schenck et al. | |
| 4,697,312 A | 10/1987 | Freyer | |
| 4,719,917 A | 1/1988 | Barrows et al. | |
| 4,724,840 A | 2/1988 | McVay et al. | |
| 4,738,658 A | 4/1988 | Magro et al. | |
| 4,744,364 A | 5/1988 | Kensey | |
| 4,747,407 A | 5/1988 | Liu et al. | |
| 4,750,492 A | 6/1988 | Jacobs | |
| 4,759,364 A | 7/1988 | Boebel | |
| 4,771,782 A | 9/1988 | Millar | |
| 4,772,266 A | 9/1988 | Groshong | 604/164.05 |
| 4,773,421 A | 9/1988 | Davis | |
| 4,777,950 A | 10/1988 | Kees, Jr. | 606/158 |
| 4,789,090 A | 12/1988 | Blake, III | |
| 4,813,586 A | 3/1989 | Seifert | |
| 4,823,794 A | 4/1989 | Pierce | |
| 4,832,688 A | 5/1989 | Sagae et al. | |
| 4,836,204 A | 6/1989 | Landymore et al. | |
| 4,852,568 A | 8/1989 | Kensey | |
| 4,860,746 A | 8/1989 | Yoon | 128/830 |
| 4,865,026 A | 9/1989 | Barrett | 606/214 |
| 4,866,818 A | 9/1989 | Thompson | |
| 4,874,122 A | 10/1989 | Froelich et al. | |
| 4,878,915 A | 11/1989 | Brantigan | |
| 4,885,003 A | 12/1989 | Hillstead | |
| 4,886,067 A | 12/1989 | Palermo | |
| 4,887,601 A | 12/1989 | Richards | |
| 4,890,612 A | 1/1990 | Kensey | |
| 4,900,303 A | 2/1990 | Lemelson | |
| 4,902,508 A | 2/1990 | Badylak et al. | |
| 4,917,087 A | 4/1990 | Walsh et al. | 606/153 |
| 4,917,089 A | 4/1990 | Sideris | |
| 4,929,240 A | 5/1990 | Kirsch et al. | |
| 4,934,364 A | 6/1990 | Green | |
| 4,950,258 A | 8/1990 | Kawai et al. | 604/530 |
| 4,957,499 A | 9/1990 | Lipatov et al. | |
| 4,961,729 A | 10/1990 | Vaillancourt | |
| 4,967,949 A | 11/1990 | Sandhaus | |
| 4,976,721 A | 12/1990 | Blasnik et al. | |
| 4,983,176 A | 1/1991 | Cushman et al. | |
| 4,997,436 A | 3/1991 | Oberlander | |
| 4,997,439 A | 3/1991 | Chen | |
| 5,002,562 A | 3/1991 | Oberlander | |
| 5,007,921 A | 4/1991 | Brown | 606/221 |
| 5,009,663 A | 4/1991 | Broomé | |
| 5,015,247 A | 5/1991 | Michelson | |
| 5,021,059 A | 6/1991 | Kensey et al. | |
| 5,026,390 A | 6/1991 | Brown | 606/221 |
| 5,030,226 A | 7/1991 | Green et al. | |
| 5,032,127 A | 7/1991 | Frazee et al. | |
| 5,035,692 A | 7/1991 | Lyon et al. | |
| 5,042,707 A | 8/1991 | Taheri | |
| 5,047,047 A | 9/1991 | Yoon | |
| 5,053,008 A | 10/1991 | Bajaj | 604/104 |
| 5,059,201 A | 10/1991 | Asnis | |
| 5,061,274 A | 10/1991 | Kensey | 606/213 |
| 5,071,430 A | 12/1991 | de Salis et al. | |
| 5,078,731 A | 1/1992 | Hayhurst | |
| 5,092,941 A | 3/1992 | Miura | |
| 5,100,418 A | 3/1992 | Yoon et al. | 606/139 |
| 5,100,422 A | 3/1992 | Berguer et al. | |
| 5,108,420 A | 4/1992 | Marks | 606/213 |
| 5,108,421 A | 4/1992 | Fowler | |
| 5,114,032 A | 5/1992 | Laidlaw | |
| 5,114,065 A | 5/1992 | Storace | |
| 5,116,349 A | 5/1992 | Aranyi | |
| 5,122,122 A | 6/1992 | Allgood | |
| 5,122,156 A | 6/1992 | Granger et al. | |
| 5,131,379 A | 7/1992 | Sewell, Jr. | |
| 5,141,520 A | 8/1992 | Goble et al. | |
| 5,147,381 A | 9/1992 | Heimerl et al. | |
| 5,156,609 A | 10/1992 | Nakao et al. | 606/142 |
| 5,158,566 A | 10/1992 | Pianetti | |
| 5,160,339 A | 11/1992 | Chen et al. | |
| 5,163,343 A | 11/1992 | Gish | |
| 5,167,634 A | 12/1992 | Corrigan, Jr. et al. | |
| 5,167,643 A | 12/1992 | Lynn | 604/263 |
| 5,171,249 A | 12/1992 | Stefanchik et al. | 606/142 |
| 5,171,250 A | 12/1992 | Yoon | |
| 5,171,251 A | 12/1992 | Bregen et al. | |
| 5,171,259 A | 12/1992 | Inoue | |
| 5,176,648 A | 1/1993 | Holmes et al. | 604/180 |
| 5,176,682 A | 1/1993 | Chow | |
| 5,192,288 A | 3/1993 | Thompson et al. | |
| 5,192,300 A | 3/1993 | Fowler | |
| 5,192,301 A | 3/1993 | Kamiya et al. | |
| 5,192,302 A | 3/1993 | Kensey et al. | 606/213 |
| 5,192,602 A | 3/1993 | Spencer et al. | |
| 5,193,533 A | 3/1993 | Body et al. | |
| 5,197,971 A | 3/1993 | Bonutti | |
| 5,203,787 A | 4/1993 | Noblitt et al. | |
| 5,207,697 A | 5/1993 | Carusillo et al. | |
| 5,209,756 A | 5/1993 | Seedhorn et al. | |
| 5,217,024 A | 6/1993 | Dorsey et al. | |
| 5,219,359 A | 6/1993 | McQuilkin et al. | |
| 5,222,974 A | 6/1993 | Kensey et al. | 606/213 |
| 5,226,908 A | 7/1993 | Yoon | |
| 5,234,449 A | 8/1993 | Bruker et al. | |
| 5,236,435 A | 8/1993 | Sewell, Jr. | |
| 5,236,445 A | 8/1993 | Hayhurst et al. | |
| 5,242,456 A | 9/1993 | Nash et al. | |
| 5,242,457 A | 9/1993 | Akopov et al. | |
| 5,242,459 A | 9/1993 | Buelna | |
| 5,246,156 A | 9/1993 | Rothfuss et al. | |
| 5,246,443 A | 9/1993 | Mai | |
| 5,250,058 A | 10/1993 | Miller et al. | |
| 5,254,105 A | 10/1993 | Haaga | |
| 5,255,679 A | 10/1993 | Imran | |
| 5,258,015 A | 11/1993 | Li et al. | |
| 5,269,792 A | 12/1993 | Kovac et al. | |
| 5,275,616 A | 1/1994 | Fowler | 606/213 |
| 5,281,422 A | 1/1994 | Badylak et al. | |

(56) References Cited

U.S. PATENT DOCUMENTS

| | | |
|---|---|---|
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. ............ 606/144 |
| 5,304,204 A | 4/1994 | Bregen |
| 5,306,254 A | 4/1994 | Nash et al. |
| 5,306,280 A | 4/1994 | Bregen et al. |
| 5,309,927 A | 5/1994 | Welch |
| 5,318,542 A | 6/1994 | Hirsch et al. ................. 606/161 |
| 5,320,639 A | 6/1994 | Rudnick |
| 5,327,908 A | 7/1994 | Gerry |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das ............................ 606/213 |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. .............. 606/151 |
| 5,366,479 A | 11/1994 | McGarry et al. |
| 5,376,101 A | 12/1994 | Green et al. |
| 5,383,896 A | 1/1995 | Gershony et al. |
| 5,383,897 A | 1/1995 | Wholey |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Velez |
| 5,395,030 A | 3/1995 | Kuramoto et al. |
| 5,404,621 A | 4/1995 | Heinke |
| 5,409,499 A | 4/1995 | Yi |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A * | 8/1995 | Shichman et al. ............ 606/220 |
| 5,443,477 A | 8/1995 | Marin et al. |
| 5,443,481 A | 8/1995 | Lee |
| 5,445,167 A * | 8/1995 | Yoon et al. ................... 128/898 |
| 5,449,359 A | 9/1995 | Groiso |
| 5,451,235 A | 9/1995 | Lock et al. |
| 5,454,413 A | 10/1995 | Morelli |
| 5,456,400 A | 10/1995 | Shichman et al. |
| 5,462,558 A | 10/1995 | Kolesa et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,474,572 A | 12/1995 | Hayhurst |
| 5,476,505 A | 12/1995 | Limon |
| 5,478,352 A | 12/1995 | Fowler |
| 5,478,353 A | 12/1995 | Yoon et al. |
| 5,478,354 A | 12/1995 | Tovey et al. .................. 606/219 |
| 5,486,195 A | 1/1996 | Myers et al. |
| 5,496,332 A | 3/1996 | Sierra et al. |
| 5,497,933 A | 3/1996 | DeFonzo et al. |
| 5,501,698 A | 3/1996 | Roth et al. |
| 5,507,744 A | 4/1996 | Tay et al. |
| 5,507,755 A | 4/1996 | Gresl et al. ................... 606/139 |
| 5,510,115 A | 4/1996 | Breillatt, Jr. et al. |
| 5,514,159 A | 5/1996 | Matula et al. |
| 5,521,184 A | 5/1996 | Zimmerman |
| 5,522,840 A | 6/1996 | Krajicek |
| 5,527,322 A | 6/1996 | Klein et al. ................... 606/144 |
| 5,536,251 A | 7/1996 | Evard et al. |
| 5,540,712 A | 7/1996 | Kleshinski et al. |
| 5,540,716 A * | 7/1996 | Hlavacek ...................... 606/219 |
| 5,543,520 A | 8/1996 | Zimmerman |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,593,422 A | 1/1997 | Muijs Van der Moer et al. |
| 5,593,425 A | 1/1997 | Bonutti et al. |
| 5,601,602 A | 2/1997 | Fowler |
| 5,609,597 A | 3/1997 | Lehrer |
| 5,611,986 A | 3/1997 | Datta et al. |
| 5,613,974 A | 3/1997 | Andreas et al. |
| 5,618,291 A | 4/1997 | Thompson et al. |
| 5,618,306 A | 4/1997 | Roth et al. |
| 5,620,452 A | 4/1997 | Yoon |
| 5,620,461 A | 4/1997 | Muijs et al. |
| 5,626,614 A | 5/1997 | Hart |
| 5,630,824 A | 5/1997 | Hart |
| 5,634,936 A | 6/1997 | Lindon et al. |
| 5,643,318 A | 7/1997 | Tsukernik et al. |
| 5,645,553 A | 7/1997 | Kolesa et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,917 A | 9/1997 | Sauer et al. |
| 5,669,935 A | 9/1997 | Rosenman et al. |
| 5,674,231 A * | 10/1997 | Green et al. .................. 606/142 |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,681,351 A | 10/1997 | Jamiolkowski et al. |
| 5,683,405 A | 11/1997 | Yacoubian et al. ........... 606/158 |
| 5,690,674 A | 11/1997 | Diaz |
| 5,695,504 A | 12/1997 | Gifford, III et al. |
| 5,695,505 A | 12/1997 | Yoon ............................. 606/157 |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,709,708 A | 1/1998 | Thal |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. .................. 606/148 |
| 5,728,116 A | 3/1998 | Rosenman |

(56) References Cited

U.S. PATENT DOCUMENTS

| | | |
|---|---|---|
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,735,875 A | 4/1998 | Bonutti et al. |
| 5,735,877 A | 4/1998 | Pagedas |
| 5,749,826 A | 5/1998 | Faulkner |
| 5,749,898 A | 5/1998 | Schulze et al. |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,147 A | 7/1998 | Dolendo |
| 5,776,150 A | 7/1998 | Nolan et al. |
| 5,779,707 A | 7/1998 | Bertholet et al. |
| 5,780,807 A | 7/1998 | Saunders |
| 5,782,844 A | 7/1998 | Yoon et al. .................... 606/139 |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. ................ 606/142 |
| 5,810,851 A | 9/1998 | Yoon ............................ 606/148 |
| 5,810,877 A | 9/1998 | Roth et al. |
| 5,814,069 A | 9/1998 | Schulze et al. |
| 5,817,113 A | 10/1998 | Gifford ........................ 606/153 |
| 5,820,631 A | 10/1998 | Nobles ......................... 606/213 |
| 5,827,298 A | 10/1998 | Hart et al. |
| 5,830,125 A | 11/1998 | Scribner et al. .............. 606/139 |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,845,657 A | 12/1998 | Carberry et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,861,043 A | 1/1999 | Carn |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. .................... 606/213 |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. ................ 606/213 |
| 5,919,207 A * | 7/1999 | Taheri ........................... 606/219 |
| 5,919,208 A | 7/1999 | Valenti |
| 5,922,009 A | 7/1999 | Epstein et al. ................ 606/213 |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. ................ 606/213 |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. .................. 604/161 |
| 5,951,575 A | 9/1999 | Bolduc et al. |
| 5,951,576 A | 9/1999 | Wakabayashi |
| 5,951,589 A | 9/1999 | Epstein et al. ................ 606/213 |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A * | 9/1999 | Tanner et al. ................. 606/155 |
| 5,964,782 A | 10/1999 | LaFontaine et al. ......... 606/213 |
| 5,972,023 A | 10/1999 | Tanner et al. |
| 5,972,034 A | 10/1999 | Hofmann et al. |
| 5,976,159 A | 11/1999 | Bolduc et al. |
| 5,976,161 A | 11/1999 | Kirsch et al. |
| 5,976,174 A | 11/1999 | Ruiz |
| 5,984,934 A | 11/1999 | Ashby et al. ................. 606/151 |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. ................... 606/213 |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. ............... 606/213 |
| 6,045,570 A | 4/2000 | Epstein et al. ................ 606/214 |
| 6,048,358 A | 4/2000 | Barak |
| 6,056,768 A | 5/2000 | Cates et al. |
| 6,056,769 A | 5/2000 | Epstein et al. ................ 606/213 |
| 6,059,800 A | 5/2000 | Hart et al. |
| 6,059,825 A | 5/2000 | Hobbs et al. |
| 6,063,085 A | 5/2000 | Tay et al. ........................ 606/50 |
| 6,063,114 A | 5/2000 | Nash et al. |
| 6,066,160 A | 5/2000 | Colvin et al. |
| 6,071,300 A | 6/2000 | Brenneman et al. |
| 6,074,395 A | 6/2000 | Trott et al. |
| 6,074,409 A | 6/2000 | Goldfarb |
| 6,077,281 A | 6/2000 | Das .............................. 606/151 |
| 6,077,291 A | 6/2000 | Das .............................. 606/213 |
| 6,080,182 A | 6/2000 | Shaw ............................ 606/213 |
| 6,080,183 A | 6/2000 | Tsugita et al. ................ 606/213 |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,095,155 A | 8/2000 | Criscuolo |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock ...................... 606/144 |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri ........................... 606/213 |
| 6,126,675 A | 10/2000 | Shchervinsky et al. |

(56) References Cited

U.S. PATENT DOCUMENTS

| | | | |
|---|---|---|---|
| 6,126,677 A | 10/2000 | Ganaja et al. | |
| 6,136,010 A | 10/2000 | Modesitt et al. | |
| 6,143,017 A | 11/2000 | Thal | |
| 6,146,385 A | 11/2000 | Torrie et al. | |
| 6,149,660 A | 11/2000 | Laufer et al. | |
| 6,149,667 A | 11/2000 | Hovland et al. | |
| 6,152,144 A | 11/2000 | Lesh et al. | |
| 6,152,934 A | 11/2000 | Harper et al. | |
| 6,152,936 A | 11/2000 | Christy et al. | |
| 6,152,937 A | 11/2000 | Peterson et al. | |
| 6,159,234 A | 12/2000 | Bonutti et al. | |
| 6,161,263 A | 12/2000 | Anderson | |
| 6,165,204 A | 12/2000 | Levinson et al. | |
| 6,171,277 B1 | 1/2001 | Ponzi | |
| 6,171,329 B1 | 1/2001 | Shaw et al. | |
| 6,174,322 B1 | 1/2001 | Schneidt | |
| 6,174,324 B1 | 1/2001 | Egan et al. | |
| 6,179,849 B1 | 1/2001 | Yencho et al. | |
| 6,179,860 B1 | 1/2001 | Fulton, III et al. | |
| 6,193,708 B1 | 2/2001 | Ken et al. | |
| 6,193,734 B1 | 2/2001 | Bolduc et al. | |
| 6,197,042 B1 | 3/2001 | Ginn et al. | 606/213 |
| 6,198,974 B1 | 3/2001 | Webster, Jr. | |
| 6,200,329 B1 | 3/2001 | Fung et al. | |
| 6,200,330 B1 | 3/2001 | Benderev et al. | |
| 6,203,565 B1 | 3/2001 | Bonutti et al. | |
| 6,206,895 B1 | 3/2001 | Levinson | |
| 6,206,913 B1 | 3/2001 | Yencho et al. | |
| 6,206,931 B1 | 3/2001 | Cook et al. | |
| 6,210,407 B1 | 4/2001 | Webster | |
| 6,210,418 B1 | 4/2001 | Storz et al. | |
| 6,220,248 B1 | 4/2001 | Voegele et al. | |
| 6,221,102 B1 | 4/2001 | Baker et al. | |
| 6,231,561 B1 | 5/2001 | Frazier et al. | |
| 6,231,592 B1 | 5/2001 | Bonutti et al. | |
| 6,238,705 B1 | 5/2001 | Liu et al. | |
| 6,241,740 B1 | 6/2001 | Davis et al. | |
| 6,245,079 B1 | 6/2001 | Nobles et al. | |
| 6,248,124 B1 | 6/2001 | Pedros et al. | |
| 6,254,615 B1 | 7/2001 | Bolduc et al. | |
| 6,254,617 B1 | 7/2001 | Spence et al. | |
| 6,254,642 B1 | 7/2001 | Taylor | |
| 6,258,115 B1 | 7/2001 | Dubrul | |
| 6,261,309 B1 | 7/2001 | Urbanski | |
| 6,267,773 B1 | 7/2001 | Gadberry et al. | |
| 6,273,903 B1* | 8/2001 | Wilk | 606/219 |
| 6,277,140 B2 | 8/2001 | Ginn et al. | 606/213 |
| 6,280,460 B1 | 8/2001 | Bolduc et al. | |
| 6,287,322 B1 | 9/2001 | Zhu et al. | |
| 6,287,335 B1 | 9/2001 | Drasler et al. | |
| 6,290,674 B1 | 9/2001 | Roue et al. | |
| 6,296,657 B1 | 10/2001 | Brucker | |
| 6,302,870 B1 | 10/2001 | Jacobsen et al. | |
| 6,302,898 B1 | 10/2001 | Edwards et al. | |
| 6,305,891 B1 | 10/2001 | Burlingame | |
| 6,309,416 B1 | 10/2001 | Swanson et al. | |
| 6,319,258 B1 | 11/2001 | McAllen, III et al. | |
| 6,322,580 B1 | 11/2001 | Kanner | |
| 6,328,727 B1 | 12/2001 | Frazier et al. | |
| 6,329,386 B1 | 12/2001 | Mollison | |
| 6,334,865 B1 | 1/2002 | Redmond et al. | 606/213 |
| 6,348,064 B1 | 2/2002 | Kanner | 606/219 |
| 6,355,052 B1 | 3/2002 | Neuss et al. | |
| 6,358,258 B1 | 3/2002 | Arcia et al. | |
| 6,375,671 B1 | 4/2002 | Kobayashi et al. | |
| D457,958 S | 5/2002 | Dycus | |
| 6,383,208 B1 | 5/2002 | Sancoff et al. | |
| 6,391,048 B1 | 5/2002 | Ginn et al. | 606/213 |
| 6,395,015 B1 | 5/2002 | Borst et al. | |
| 6,398,752 B1 | 6/2002 | Sweezer et al. | |
| 6,402,765 B1 | 6/2002 | Monassevitch et al. | |
| 6,409,739 B1 | 6/2002 | Nobles et al. | 606/148 |
| 6,419,669 B1 | 7/2002 | Frazier et al. | |
| 6,421,899 B1 | 7/2002 | Zitnay | |
| 6,423,054 B1 | 7/2002 | Ouchi | |
| 6,425,911 B1 | 7/2002 | Akerfeldt et al. | |
| 6,428,472 B1 | 8/2002 | Haas | |
| 6,428,548 B1 | 8/2002 | Durgin et al. | |
| 6,443,158 B1 | 9/2002 | Lafontaine et al. | |
| 6,443,963 B1 | 9/2002 | Baldwin et al. | |
| 6,447,540 B1 | 9/2002 | Fontaine et al. | |
| 6,450,391 B1 | 9/2002 | Kayan et al. | |
| 6,455,053 B1 | 9/2002 | Okada et al. | |
| 6,458,130 B1 | 10/2002 | Frazier et al. | |
| 6,461,364 B1 | 10/2002 | Ginn et al. | |
| 6,482,224 B1 | 11/2002 | Michler et al. | |
| 6,488,692 B1 | 12/2002 | Spence et al. | |
| 6,494,848 B1 | 12/2002 | Sommercorn et al. | |
| 6,500,115 B2 | 12/2002 | Krattiger et al. | |
| 6,506,210 B1 | 1/2003 | Kanner | |
| 6,508,828 B1 | 1/2003 | Akerfeldt et al. | |
| 6,514,280 B1 | 2/2003 | Gilson | |
| 6,517,555 B1 | 2/2003 | Caro | |
| 6,517,569 B2 | 2/2003 | Mikus et al. | |
| 6,527,737 B2 | 3/2003 | Kaneshige | |
| 6,533,762 B2 | 3/2003 | Kanner et al. | |
| 6,533,812 B2 | 3/2003 | Swanson et al. | |
| 6,537,288 B2 | 3/2003 | Vargas et al. | |
| 6,544,230 B1 | 4/2003 | Flaherty et al. | |
| 6,547,806 B1 | 4/2003 | Ding | 606/213 |
| 6,551,319 B2 | 4/2003 | Lieberman | |
| 6,558,349 B1 | 5/2003 | Kirkman | |
| 6,569,173 B1 | 5/2003 | Blatter et al. | |
| 6,569,185 B2 | 5/2003 | Ungs | |
| 6,572,629 B2 | 6/2003 | Kalloo et al. | |
| 6,578,585 B1 | 6/2003 | Stachowski et al. | |
| 6,582,452 B2 | 6/2003 | Coleman et al. | 606/213 |
| 6,582,482 B2 | 6/2003 | Gillman et al. | |
| 6,596,012 B2 | 7/2003 | Akerfeldt et al. | |
| 6,596,013 B2 | 7/2003 | Yang et al. | |
| 6,599,303 B1 | 7/2003 | Peterson et al. | |
| 6,599,311 B1 | 7/2003 | Biggs et al. | |
| 6,602,263 B1 | 8/2003 | Swanson et al. | |
| 6,610,072 B1 | 8/2003 | Christy et al. | |
| 6,613,059 B2 | 9/2003 | Schaller et al. | |
| 6,613,060 B2 | 9/2003 | Adams et al. | |
| 6,616,686 B2 | 9/2003 | Coleman et al. | |
| 6,620,165 B2 | 9/2003 | Wellisz | |
| 6,623,509 B2 | 9/2003 | Ginn | |
| 6,623,510 B2 | 9/2003 | Carley et al. | |
| 6,626,918 B1 | 9/2003 | Ginn et al. | |
| 6,626,919 B1 | 9/2003 | Swanstrom | |
| 6,626,920 B2 | 9/2003 | Whayne | |
| 6,626,930 B1 | 9/2003 | Allen et al. | |
| 6,632,197 B2 | 10/2003 | Lyon | |
| 6,632,238 B2 | 10/2003 | Ginn et al. | 606/213 |
| 6,634,537 B2 | 10/2003 | Chen | |
| 6,645,205 B2 | 11/2003 | Ginn | |
| 6,645,225 B1 | 11/2003 | Atkinson | |
| 6,652,538 B2 | 11/2003 | Kayan et al. | |
| 6,652,556 B1 | 11/2003 | VanTassel et al. | |
| 6,663,633 B1 | 12/2003 | Pierson, III | |
| 6,663,655 B2 | 12/2003 | Ginn et al. | |
| 6,669,714 B2 | 12/2003 | Coleman et al. | |
| 6,673,083 B1 | 1/2004 | Kayan et al. | |
| 6,676,665 B2 | 1/2004 | Foley et al. | |
| 6,676,671 B2 | 1/2004 | Robertson et al. | |
| 6,676,685 B2 | 1/2004 | Pedros et al. | |
| 6,679,904 B2 | 1/2004 | Gleeson et al. | |
| 6,685,707 B2 | 2/2004 | Roman et al. | |
| 6,689,147 B1 | 2/2004 | Koster, Jr. | |
| 6,695,867 B2 | 2/2004 | Ginn et al. | 606/213 |
| 6,699,256 B1 | 3/2004 | Logan et al. | |
| 6,702,826 B2 | 3/2004 | Liddicoat et al. | |
| 6,712,836 B1 | 3/2004 | Berg et al. | |
| 6,712,837 B2 | 3/2004 | Akerfeldt et al. | |
| 6,719,777 B2 | 4/2004 | Ginn et al. | |
| 6,726,704 B1 | 4/2004 | Loshakove et al. | |
| 6,736,822 B2 | 5/2004 | McClellan et al. | |
| 6,743,195 B2 | 6/2004 | Zucker | |
| 6,743,243 B1 | 6/2004 | Roy et al. | |
| 6,743,259 B2 | 6/2004 | Ginn | |
| 6,746,472 B2 | 6/2004 | Frazier et al. | |
| 6,749,621 B2 | 6/2004 | Pantages et al. | |

(56) References Cited

U.S. PATENT DOCUMENTS

| | | |
|---|---|---|
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. ............. 606/213 |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,850,710 B2 | 12/2010 | Huss |
| 7,875,054 B2 | 1/2011 | LaFontaine |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 8,409,228 B2 | 4/2013 | Blatter et al. |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026208 A1 | 2/2002 | Belef |
| 2002/0026215 A1 | 2/2002 | Redmond et al. ............. 606/213 |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049472 A1 | 4/2002 | Coleman et al. |
| 2002/0058960 A1 | 5/2002 | Hudson et al. |
| 2002/0062104 A1 | 5/2002 | Ashby et al. |
| 2002/0072768 A1 | 6/2002 | Ginn ............................. 606/213 |
| 2002/0077656 A1 | 6/2002 | Ginn et al. |
| 2002/0077657 A1 | 6/2002 | Ginn et al. ................... 606/213 |
| 2002/0077658 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0188318 A1 | 12/2002 | Carley et al. .................. 606/213 |
| 2002/0193808 A1 | 12/2002 | Belef et al. ................... 606/139 |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. ........... 606/144 |
| 2003/0009196 A1 | 1/2003 | Peterson |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. .................... 606/142 |
| 2003/0083679 A1 | 5/2003 | Grudem et al. |
| 2003/0093096 A1 | 5/2003 | McGuckin, Jr. et al. .... 606/157 |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding ............................. 606/213 |
| 2003/0139819 A1 | 7/2003 | Beer et al. |
| 2003/0144695 A1 | 7/2003 | McGuckin, Jr. et al. |
| 2003/0158577 A1 | 8/2003 | Ginn et al. .................... 606/213 |
| 2003/0158578 A1 | 8/2003 | Pantages et al. ............. 606/213 |
| 2003/0195504 A1 | 10/2003 | Tallarida et al. |
| 2003/0195561 A1 | 10/2003 | Carley et al. |
| 2003/0208211 A1 | 11/2003 | Kortenbach |

(56) References Cited

U.S. PATENT DOCUMENTS

| | | |
|---|---|---|
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0195125 A1 | 8/2006 | Sakakine et al. |
| 2006/0206146 A1 | 9/2006 | Tenerez |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0114378 A1 | 5/2008 | Matsushita |
| 2008/0114395 A1 | 5/2008 | Mathisen et al. |

(56) References Cited

U.S. PATENT DOCUMENTS

| | | |
|---|---|---|
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312666 A1 | 12/2008 | Ellingwood et al. |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0082495 A1 | 4/2011 | Ruiz |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Kariniemi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |
| 2014/0142624 A1 | 5/2014 | Pantages et al. |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |

FOREIGN PATENT DOCUMENTS

| | | | |
|---|---|---|---|
| DE | 197 11 288 | 1/1998 | |
| DE | 297 23 736 U 1 | 4/1999 | |
| DE | 19859952 | 2/2000 | |
| DE | 102006056283 | 6/2008 | |
| EP | 0 386 361 | 9/1990 | |
| EP | 0 534 696 | 3/1993 | |
| EP | 0 621 032 | 10/1994 | |
| EP | 0 756 851 | 2/1997 | |
| EP | 0 744 237 | 5/1997 | ............ A61B 17/00 |
| EP | 0 858 776 | 8/1998 | |
| EP | 0 941 697 | 9/1999 | |
| EP | 1 867 287 | 12/2007 | |
| FR | 2 443 238 | 7/1980 | |
| FR | 2 715 290 | 7/1995 | |
| FR | 2 722 975 | 2/1996 | |
| FR | 2 768 324 | 3/1999 | |
| GB | 1 358 466 | 7/1974 | |
| GB | 2 075 144 | 11/1981 | |
| GB | 2 397 240 | 7/2004 | |
| IE | S 2000/0722 | 10/2001 | |
| IE | S 2000/0724 | 10/2001 | |
| IE | S 2001/0547 | 7/2002 | |
| IE | S 2001/0815 | 7/2002 | |
| IE | S 2001/0748 | 8/2002 | |
| IE | S 2001/0749 | 8/2002 | |
| IE | S 2002/0452 | 12/2002 | |
| IE | S 2002/0664 | 2/2003 | |
| IE | S 2002/0665 | 2/2003 | |
| IE | S 2002/0451 | 7/2003 | |
| IE | S 2002/0552 | 7/2003 | |
| IE | S 2003/0424 | 12/2003 | |
| IE | S 2003/0490 | 1/2004 | |
| IE | S 2004/0368 | 11/2005 | |
| IE | S 2005/0342 | 11/2005 | |
| JP | 58-181006 | 12/1983 | |
| JP | 12 74750 | 11/1989 | |
| JP | 11500642 | 8/1997 | |
| JP | 2000102546 | 4/2000 | |
| NL | 9302140 | 7/1995 | |
| PL | 171425 | 4/1997 | |
| RU | 2086192 | 8/1997 | |
| SU | 197801 | 6/1967 | |
| SU | 495067 | 12/1975 | |
| SU | 912155 | 3/1982 | |
| SU | 1243708 | 7/1986 | |
| SU | 1324650 | 7/1987 | |
| SU | 1405828 | 6/1988 | |
| SU | 1456109 | 2/1989 | |
| SU | 1560133 | 4/1990 | |
| WO | WO 95/21573 | 8/1995 | |
| WO | WO 96/24291 | 8/1996 | ............ A61B 17/04 |
| WO | WO 97/07741 | 3/1997 | |
| WO | WO 97/20505 | 6/1997 | ............ A61B 17/00 |
| WO | WO 97/27897 | 8/1997 | |
| WO | WO 97/28745 | 8/1997 | |
| WO | WO 98/06346 | 2/1998 | |
| WO | WO 98/06448 | 2/1998 | |
| WO | WO 98/16161 | 4/1998 | |
| WO | WO 98/17179 | 4/1998 | |
| WO | WO 98/18389 | 5/1998 | |
| WO | WO 98/24374 | 6/1998 | ............ A61B 17/00 |
| WO | WO 98/25508 | 6/1998 | |
| WO | WO 98/58591 | 12/1998 | |
| WO | WO 99/21491 | 5/1999 | |
| WO | WO 99/40849 | 8/1999 | |
| WO | WO 99/60941 | 12/1999 | |
| WO | WO 99/62408 | 12/1999 | ............ A61B 17/08 |
| WO | WO 99/62415 | 12/1999 | |
| WO | WO 00/06029 | 2/2000 | |
| WO | WO 00/07505 | 2/2000 | |
| WO | WO 00/07640 | 2/2000 | ............ A61B 17/04 |
| WO | WO 00/27311 | 5/2000 | |
| WO | WO 00/27313 | 5/2000 | |
| WO | WO 00/56223 | 9/2000 | ............ A61B 17/00 |
| WO | WO 00/56227 | 9/2000 | ............ A61B 17/08 |
| WO | WO 00/56228 | 9/2000 | |
| WO | WO 00/60029 | 10/2000 | ............ C10L 1/08 |
| WO | WO 00/71032 | 11/2000 | |
| WO | WO 01/21058 | 3/2001 | |
| WO | WO 01/35832 | 5/2001 | ............ A61B 17/03 |
| WO | WO 01/47594 | 7/2001 | |
| WO | WO 01/49186 | 7/2001 | |
| WO | WO 01/91628 | 12/2001 | |
| WO | WO 02/19915 | 3/2002 | |
| WO | WO 02/19920 | 3/2002 | |
| WO | WO 02/19922 | 3/2002 | |
| WO | WO 02/19924 | 3/2002 | |
| WO | WO 02/28286 | 4/2002 | |
| WO | WO 02/38055 | 5/2002 | |

(56) References Cited

FOREIGN PATENT DOCUMENTS

| | | |
|---|---|---|
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 03/071957 | 1/2004 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 20010527 | 1/2001 |
| ZA | 200100528 | 1/2001 |

OTHER PUBLICATIONS

U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
U.S. Appl. No. 60/696,069, filed Jul. 1, 2005, Pantages et al.
U.S. Appl. No. 60/946,026, filed Jun. 25, 2007, Ellingwood.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials And Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
McCarthy, et al., "Tension (Stay) Suture Bridge", J. of International College of Surgeons, 34(5), pp. 613-614 (Nov. 1960).
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

(56) References Cited

OTHER PUBLICATIONS

SA Beyer-Enke et al, Immediate sealing of arterial puncture site following femoropopliteal angioplasty: A prospective randomized trial, Cardiovascular And Interventional Radiology 1996, Nov.-Dec. 1996, pp. 406-410, vol. 19—No. 6, Gen Hosp North, Dept Dianost & Intervent Radiol, Numberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

Database WPI; Section PQ, Week 200120; Derwent Publications Ltd., London GB; Class P31, AN 2001-203165; XP002199926 & ZA 200 100 528 A (Anthony T), Feb. 28, 2001 abstract.

U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
Stretch Comb by Scunci, retrieved via internet at www.scunci.com/productdetail by examiner on Oct. 9, 2007, publication date unavailable.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/680,837, Sep. 11, 2003, Issue Notification.
U.S. Appl. No. 10/006,400, Jul. 9, 2009, Notice of Allowance.
U.S. Appl. No. 10/264,306, Aug. 13, 2009, Office Action.
U.S. Appl. No. 10/356,214, Apr. 29, 2009, Office Action.
U.S. Appl. No. 10/517,004, Jun. 26, 2009, Notice of Allowance.
U.S. Appl. No. 10/541,083, Apr. 16, 2009, Notice of Allowance.
U.S. Appl. No. 10/616,832, Jul. 21, 2009, Office Action.
U.S. Appl. No. 10/638,115, May 7, 2009, Notice of Allowance.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/669,313, Nov. 15, 2006, Issue Notification.
U.S. Appl. No. 10/682,459, Jun. 10, 2009, Office Action.
U.S. Appl. No. 10/786,444, Jun. 18, 2009, Office Action.
U.S. Appl. No. 10/787,073, Aug. 13, 2009, Office Action.
U.S. Appl. No. 10/908,721, Jun. 23, 2009, Office Action.
U.S. Appl. No. 11/048,503, Jun. 26, 2009, Office Action.
U.S. Appl. No. 11/113,549, Jul. 21, 2009, Office Action.
U.S. Appl. No. 11/152,562, Jul. 6, 2009, Office Action.
U.S. Appl. No. 11/198,811, Sep. 22, 2009, Office Action.
U.S. Appl. No. 11/390,586, Jun. 24, 2009, Office Action.
U.S. Appl. No. 11/396,141, May 22, 2009, Restriction Requirement.
U.S. Appl. No. 11/396,141, Aug. 26, 2009, Office Action.
U.S. Appl. No. 11/406,203, Sep. 16, 2009, Office Action.
U.S. Appl. No. 11/411,925, Sep. 10, 2009, Office Action.
U.S. Appl. No. 11/427,297, Sep. 15, 2009, Office Action.
U.S. Appl. No. 11/461,323, Jul. 27, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/744,089, Aug. 14, 2009, Office Action.
U.S. Appl. No. 11/958,295, Aug. 27, 2009, Office Action.
U.S. Appl. No. 29/296,370, Apr. 1, 2009, Notice of Allowance.
U.S. Appl. No. 11/852,190, Mar. 2, 2011, Office Action.
U.S. Appl. No. 12/122,603, Mar. 3, 2011, Office Action.
U.S. Appl. No. 13/030,922, filed Feb. 18, 2011, Cummins.
U.S. Appl. No. 13/039,087, filed Mar. 2, 2011, Palermo et al.
U.S. Appl. No. 10/356,214, Feb. 23, 2011, Issue Notification.
U.S. Appl. No. 10/638,115, Dec. 22, 2010, Issue Notification.
U.S. Appl. No. 10/435,104, Jan. 12, 2011, Issue Notification.
U.S. Appl. No. 12/113,851, Dec. 16, 2010, Office Action.
U.S. Appl. No. 12/114,091, Dec. 17, 2010, Office Action.
U.S. Appl. No. 10/147,774, Dec. 2, 2010, Notice of Allowance.
U.S. Appl. No. 10/264,306, Oct. 29, 2010, Notice of Allowance.
U.S. Appl. No. 10/356,214, Sep. 3, 2010, Notice of Allowance.
U.S. Appl. No. 10/435,104, Oct. 5, 2010, Notice of Allowance.
U.S. Appl. No. 10/517,004, Nov. 23, 2010, Issue Notification.
U.S. Appl. No. 10/682,459, Oct. 12, 2010, Office Action.
U.S. Appl. No. 11/198,811, Oct. 20, 2010, Issue Notification.
U.S. Appl. No. 11/406,203, Oct. 6, 2010, Issue Notification.
U.S. Appl. No. 11/427,309, Nov. 15, 2010, Office Action.
U.S. Appl. No. 11/532,576, Oct. 13, 2010, Notice of Allowance.
U.S. Appl. No. 11/852,190, Nov. 1, 2010, Office Action.
U.S. Appl. No. 11/958,281, Oct. 8, 2010, Office Action.
U.S. Appl. No. 12/106,928, Oct. 25, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/403,256, Nov. 23, 2010, Issue Notification.
U.S. Appl. No. 12/403,277, Oct. 12, 2010, Office Action.
U.S. Appl. No. 12/114,091, Oct. 27, 2010, Office Action.
U.S. Appl. No. 10/541,083, Dec. 1, 2010, Issue Notification.
U.S. Appl. No. 12/897,358, filed Oct. 4, 2010, Carley.
U.S. Appl. No. 12/961,331, filed Dec. 6, 2010, Voss.
U.S. Appl. No. 12/966,923, filed Dec. 13, 2010, Cummins et al.
U.S. Appl. No. 11/048,503, Dec. 8, 2010, Issue Notification.
U.S. Appl. No. 11/959,334, Nov. 10, 2010, Issue Notification.
U.S. Appl. No. 11/427,297, Sep. 15, 2010, Office Action.
U.S. Appl. No. 11/767,818, Sep. 30, 2010, Office Action.
U.S. Appl. No. 12/365,397, Sep. 13, 2010, Office Action.
U.S. Appl. No. 12/402,398, Jan. 24, 2011, Office Action.
U.S. Appl. No. 12/945,646, Jan. 20, 2011, Office Action.
U.S. Appl. No. 60/693,531, filed Jun. 24, 2005, Carly.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.

(56) References Cited

OTHER PUBLICATIONS

U.S. Appl. No. 09/866,551, filed May 25, 2001, Ginn.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/147,774, Oct. 26, 2009, Office Action.
U.S. Appl. No. 10/147,774, Jun. 8, 2010, Office Action.
U.S. Appl. No. 10/264,306, Jan. 27, 2010, Office Action.
U.S. Appl. No. 10/264,306, Jun. 15, 2010, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Jan. 14, 2010, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Feb. 2, 2010, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Jul. 6, 2010, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jul. 6, 2010, Office Action.
U.S. Appl. No. 11/396,141, May 4, 2010, Office Action.
U.S. Appl. No. 11/406,203, Jun. 18, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,281, Sep. 2, 2010, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Oct. 5, 2009, Office Action.
U.S. Appl. No. 12/106,928, May 10, 2010, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 29/296,370, Feb. 10, 2010, Issue Notification.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, field Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 11/113,549, Jan. 4, 2011, Office Action.
U.S. Appl. No. 10/616,832, Jan. 26, 2011, Issue Notification.
U.S. Appl. No. 11/152,562, Jan. 26, 2011, Issue Notification.
U.S. Appl. No. 11/958,281, Mar. 10, 2011, Office Action.
U.S. Appl. No. 13/111,371, filed May 19, 2011, Ziobro.
U.S. Appl. No. 10/682,459, Aug. 10, 2011, Issue Notification.
U.S. Appl. No. 13/153,594, filed Jun. 6, 2011, Reyes et al.
U.S. Appl. No. 10/667,144, Jun. 6, 2011, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 12/135,858, Jul. 13, 2011, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 13/028,041, filed Feb. 15, 2011, Von Oepen.
U.S. Appl. No. 13/112,618, filed May 20, 2011, Gainotti et al.
U.S. Appl. No. 13/112,631, filed May 20, 2011, Voss.
U.S. Appl. No. 10/682,459, Apr. 1, 2011, Office Action.
U.S. Appl. No. 11/427,297, Mar. 21, 2011, Office Action.
U.S. Appl. No. 12/113,851, Apr. 27, 2011, Office Action.
U.S. Appl. No. 12/114,031, May 11, 2011, Office Action.
U.S. Appl. No. 12/122,603, Apr. 22, 2011, Office Action.
U.S. Appl. No. 12/143,020, May 11, 2011, Office Action.
U.S. Appl. No. 12/403,277, Mar. 31, 2011, Office Action.
U.S. Appl. No. 12/481,377, Apr. 28, 2011, Office Action.
U.S. Appl. No. 12/955,859, May 26, 2011, Office Action.
U.S. Appl. No. 12/608,769, Feb. 10, 2012, Office Action.
U.S. Appl. No. 12/684,400, Feb. 13, 2012, Office Action.

(56) References Cited

OTHER PUBLICATIONS

U.S. Appl. No. 12/724,304, Feb. 10, 2012, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/684,562, Feb. 16, 2012, Office Action.
U.S. Appl. No. 12/945,646, Feb. 21, 2012, Notice of Allowance.
U.S. Appl. No. 12/402,398, Mar. 13, 2013, Notice of Allowance.
U.S. Appl. No. 13/028,041, Jan. 4, 2013, Office Action.
U.S. Appl. No. 13/028,041, Feb. 26, 2013, Office Action.
U.S. Appl. No. 12/113,851, Mar. 29, 2012, Office Action.
U.S. Appl. No. 12/403,277, Apr. 3, 2012, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 11/427,309, Jun. 7, 2013, Notice of Allowance.
U.S. Appl. No. 13/111,371, Jun. 6, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 10/786,444, Jul. 11, 2013, Notice of Allowance.
U.S. Appl. No. 11/532,325, Jul. 17, 2013, Office Action.
U.S. Appl. No. 13/030,922, Jul. 18, 2013, Office Action.
U.S. Appl. No. 13/525,839, Jul. 15, 2013, Notice of Allowance.
U.S. Appl. No. 13/615,547, Jul. 10, 2013, Issue Notification.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 13/026,989, Aug. 23, 2013, Office Action.
U.S. Appl. No. 13/308,277, Sep. 11, 2013, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 12/987,792, Sep. 17, 2012, Office Action.
U.S. Appl. No. 13/111,371, Oct. 12, 2012, Office Action.
U.S. Appl. No. 11/675,462, Dec. 22, 2011, Notice of Allowance.
U.S. Appl. No. 12/393,877, Dec. 13, 2011, Office Action.
U.S. Appl. No. 12/684,470, Dec. 20, 2011, Restriction Requirement.
U.S. Appl. No. 12/684,569, Dec. 20, 2011, Restriction Requirement.
U.S. Appl. No. 12/941,809, Dec. 13, 2011, Restriction Requirement.
U.S. Appl. No. 12/955,859, Dec. 15, 2011, Office Action.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 12/961,331, Feb. 1, 2013, Office Action.
U.S. Appl. No. 13/488,233, Feb. 5, 2013, Notice of Allowance.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 12/684,470, Mar. 23, 2012, Office Action.
U.S. Appl. No. 13/791,829, filed Mar. 8, 2013, Roorda et al.
U.S. Appl. No. 13/791,746, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 12/114,091, Apr. 5, 2012, Office Action.
U.S. Appl. No. 12/684,542, Apr. 16, 2012, Office Action.
U.S. Appl. No. 13/308,227, filed Nov. 30, 2011, Yibarren.
U.S. Appl. No. 12/688,065, Apr. 26, 2012, Office Action.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 13/898,202, filed May 20, 2013, Walberg et al.
U.S. Appl. No. 13/153,594, May 29, 2013, Office Action.
U.S. Appl. No. 13/791,829, May 29, 2013, Office Action.
U.S. Appl. No. 12/608,773, Jun. 7, 2012, Office Action.
U.S. Appl. No. 13/026,989, Jun. 8, 2012, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 12/724,304, Jul. 11, 2012, Notice of Allowance.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 11/396,141, Aug. 21, 2013, Office Action.
U.S. Appl. No. 13/028,041, Aug. 21, 2013, Notice of Allowance.
U.S. Appl. No. 13/490,143, Aug. 21, 2013, Issue Notification.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/724,304, Oct. 17, 2012, Issue Notification.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 13/222,899, filed Aug. 31, 2011, Carley et al.
U.S. Appl. No. 10/667,144, Oct. 28, 2011, Notice of Allowance.
U.S. Appl. No. 12/122,603, Sep. 23, 2011, Office Action.
U.S. Appl. No. 12/143,020, Aug. 31, 2011, Office Action.
U.S. Appl. No. 12/393,877, Sep. 29, 2011, Office Action.
U.S. Appl. No. 12/897,358, Aug. 22, 2011, Office Action.
U.S. Appl. No. 12/945,646, Oct. 26, 2011, Office Action.
U.S. Appl. No. 13/026,989, Sep. 16, 2011, Office Action.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 13/111,371, Dec. 18, 2012, Office Action.
U.S. Appl. No. 12/338,977, Jun. 19, 2013, Office Action.
U.S. Appl. No. 12/114,031, Mar. 6, 2012, Office Action.
U.S. Appl. No. 12/688,065, Mar. 13, 2012, Office Action.
U.S. Appl. No. 12/724,304, Mar. 13, 2013, Interview Summary.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.

(56) References Cited

OTHER PUBLICATIONS

U.S. Appl. No. 12/338,977, Jan. 19, 2012, Office Action.
U.S. Appl. No. 12/684,569, Jan. 27, 2012, Office Action.
U.S. Appl. No. 12/897,358, Jan. 12, 2012, Notice of Allowance.
U.S. Appl. No. 12/608,773, Jan. 7, 2013, Office Action.
U.S. Appl. No. 13/490,143, Jan. 4, 2013, Restriction Requirement.
U.S. Appl. No. 13/615,547, Jan. 18, 2013, Office Action.
U.S. Appl. No. 12/106,928, Jun. 28, 2013, Office Action.
U.S. Appl. No. 12/106,937, Jun. 28, 2013, Office Action.
U.S. Appl. No. 12/941,809, Jul. 3, 2013, Office Action.
U.S. Appl. No. 12/961,331, Jul. 3, 2013, Office Action.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 14/539,830, filed Nov. 12, 2014, Clark.
U.S. Appl. No. 14/562,467, filed Dec. 5, 2014, Ellingwood et al.
U.S. Appl. No. 11/113,549, Mar. 14, 2014, Notice of Allowance.
U.S. Appl. No. 11/396,141, Nov. 4, 2013, Notice of Allowance.
U.S. Appl. No. 11/411,925, Oct. 1, 2013, Office Action.
U.S. Appl. No. 11/411,925, Feb. 5, 2014, Notice of Allowance.
U.S. Appl. No. 11/455,993, Jan. 29, 2014, Office Action.
U.S. Appl. No. 11/455,993, Aug. 11, 2014, Notice of Allowance.
U.S. Appl. No. 11/455,993, Dec. 17, 2014, Issue Notification.
U.S. Appl. No. 11/532,325, Dec. 2, 2013, Office Action.
U.S. Appl. No. 11/532,325, Jan. 16, 2015, Notice of Allowance.
U.S. Appl. No. 11/674,930, Apr. 3, 2014, Notice of Allowance.
U.S. Appl. No. 11/852,190, Nov. 26, 2013, Office Action.
U.S. Appl. No. 11/852,190, Feb. 12, 2014, Notice of Allowance.
U.S. Appl. No. 11/958,295, Jun. 13, 2014, Notice of Allowance.
U.S. Appl. No. 12/106,928, Dec. 2, 2013, Office Action.
U.S. Appl. No. 12/106,928, Mar. 25, 2014, Advisory Action.
U.S. Appl. No. 12/106,928, Oct. 3, 2014, Notice of Allowance.
U.S. Appl. No. 12/106,928, Jan. 27, 2015, Issue Notification.
U.S. Appl. No. 12/106,937, Jan. 22, 2014, Office Action.
U.S. Appl. No. 12/113,851, Mar. 17, 2014, Office Action.
U.S. Appl. No. 12/113,851, Aug. 21, 2014, Office Action.
U.S. Appl. No. 12/114,031, Mar. 10, 2014, Office Action.
U.S. Appl. No. 12/122,603, Nov. 20, 2013, Office Action.
U.S. Appl. No. 12/122,603, Apr. 30, 2014, Office Action.
U.S. Appl. No. 12/393,877, Aug. 4, 2014, Notice of Allowance.
U.S. Appl. No. 12/403,277, Jan. 27, 2014, Office Action.
U.S. Appl. No. 12/403,277, Aug. 15, 2014, Office Action.
U.S. Appl. No. 12/548,274, Aug. 14, 2014, Office Action.
U.S. Appl. No. 12/608,773, Jul. 17, 2014, Office Action.
U.S. Appl. No. 12/642,319, Dec. 16, 2013, Office Action.
U.S. Appl. No. 12/642,319, May 27, 2014, Notice of Allowance.
U.S. Appl. No. 12/684,470, Jun. 4, 2014, Office Action.
U.S. Appl. No. 12/684,470, Nov. 14, 2014, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Sep. 10, 2014, Office Action.
U.S. Appl. No. 12/684,569, Apr. 23, 2014, Office Action.
U.S. Appl. No. 12/688,065, Oct. 18, 2013, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/941,809, Nov. 8, 2013, Office Action.
U.S. Appl. No. 12/941,809, Feb. 3, 2014, Notice of Allowance.
U.S. Appl. No. 12/950,628, Apr. 25, 2014, Notice of Allowance.
U.S. Appl. No. 12/961,331, Sep. 20, 2013, Advisory Action.
U.S. Appl. No. 12/961,331, Apr. 25, 2014, Notice of Allowance.
U.S. Appl. No. 12/987,792, Jan. 21, 2014, Office Action.
U.S. Appl. No. 12/987,792, Jun. 11, 2014, Office Action.
U.S. Appl. No. 12/987,792, Aug. 25, 2014, Notice of Allowance.
U.S. Appl. No. 13/030,922, Jan. 8, 2014, Notice of Allowance.
U.S. Appl. No. 13/112,618, Nov. 20, 2013, Office Action.
U.S. Appl. No. 13/112,618, Dec. 15, 2014, Office Action.
U.S. Appl. No. 13/112,631, Dec. 2, 2013, Office Action.
U.S. Appl. No. 13/112,631, Nov. 20, 2014, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/222,899, Jul. 31, 2014, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 13/898,202, Aug. 21, 2014, Office Action.
U.S. Appl. No. 14/017,039, Jan. 23, 2015, Office Action.
U.S. Appl. No. 12/106,937, Mar. 5, 2015, Notice of Allowance.
U.S. Appl. No. 12/113,851, Feb. 20, 2015, Notice of Allowance.
U.S. Appl. No. 12/114,091, Feb. 12, 2015, Office Action.
U.S. Appl. No. 12/122,603, Apr. 9, 2012, Office Action.
U.S. Appl. No. 12/608,773, Mar. 12, 2015, Office Action.
U.S. Appl. No. 12/684,400, Feb. 23, 2015, Office Action.
U.S. Appl. No. 12/684,562, Feb. 17, 2015, Notice of Allowance.
U.S. Appl. No. 13/112,631, Apr. 15, 2015, Office Action.
U.S. Appl. No. 13/222,899, Apr. 1, 2015, Office Action.
U.S. Appl. No. 13/898,202, Feb. 10, 2015, Notice of Allowance.
U.S. Appl. No. 12/106,937, May 20, 2015, Issue Notification.
U.S. Appl. No. 12/113,851, Jun. 3, 2015, Issue Notification.
U.S. Appl. No. 13/112,618, May 18, 2015, Office Action.
U.S. Appl. No. 13/791,846, Jun. 4, 2015, Office Action.
U.S. Appl. No. 13/898,202, May 20, 2015, Issue Notification.
U.S. Appl. No. 14/017,039, Jun. 10, 2015, Office Action.
U.S. Appl. No. 12/114,091, Jul. 23, 2015, Office Action.
U.S. Appl. No. 12/684,400, Jul. 28, 2015, Notice of Allowance.
U.S. Appl. No. 13/222,899, Aug. 5, 2015, Office Action.
U.S. Appl. No. 13/908,796, Jul. 21, 2015, Office Action.
U.S. Appl. No. 14/023,428, Jul. 27, 2015, Office Action.
U.S. Appl. No. 14/077,007, Jul. 27, 2015, Office Action.
U.S. Appl. No. 14/246,926, Aug. 5, 2015, Office Action.

* cited by examiner

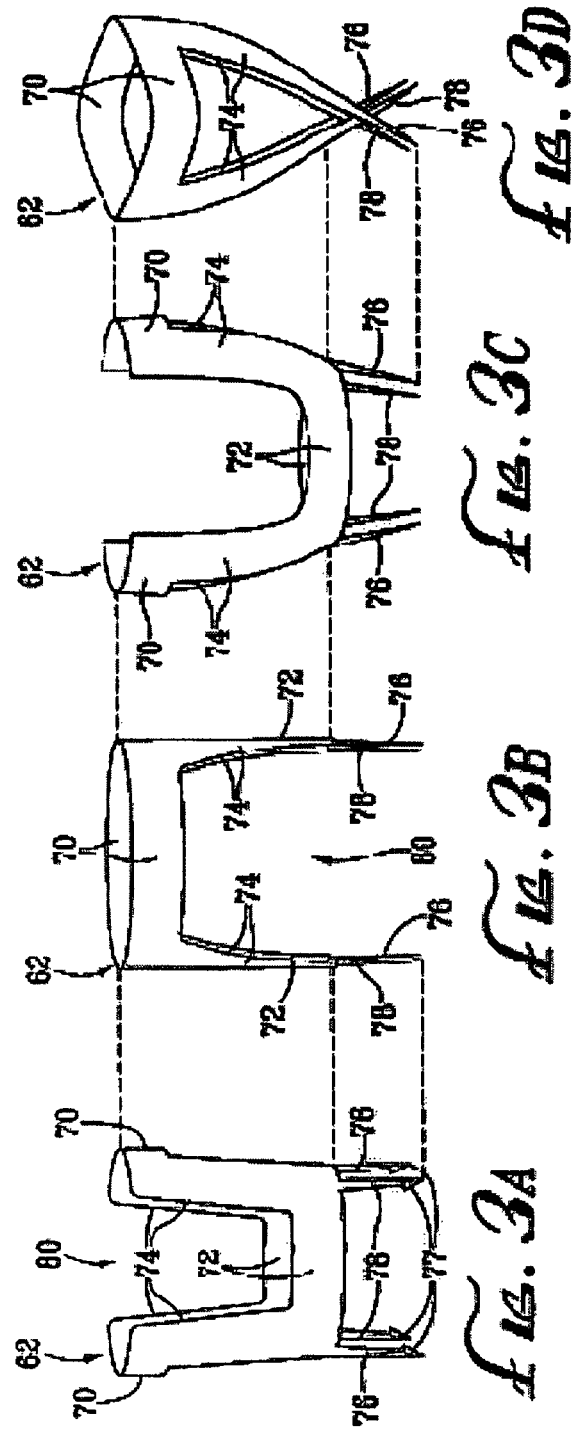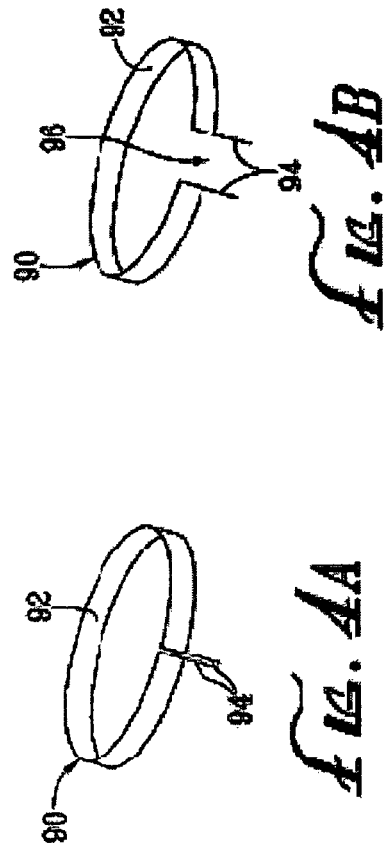

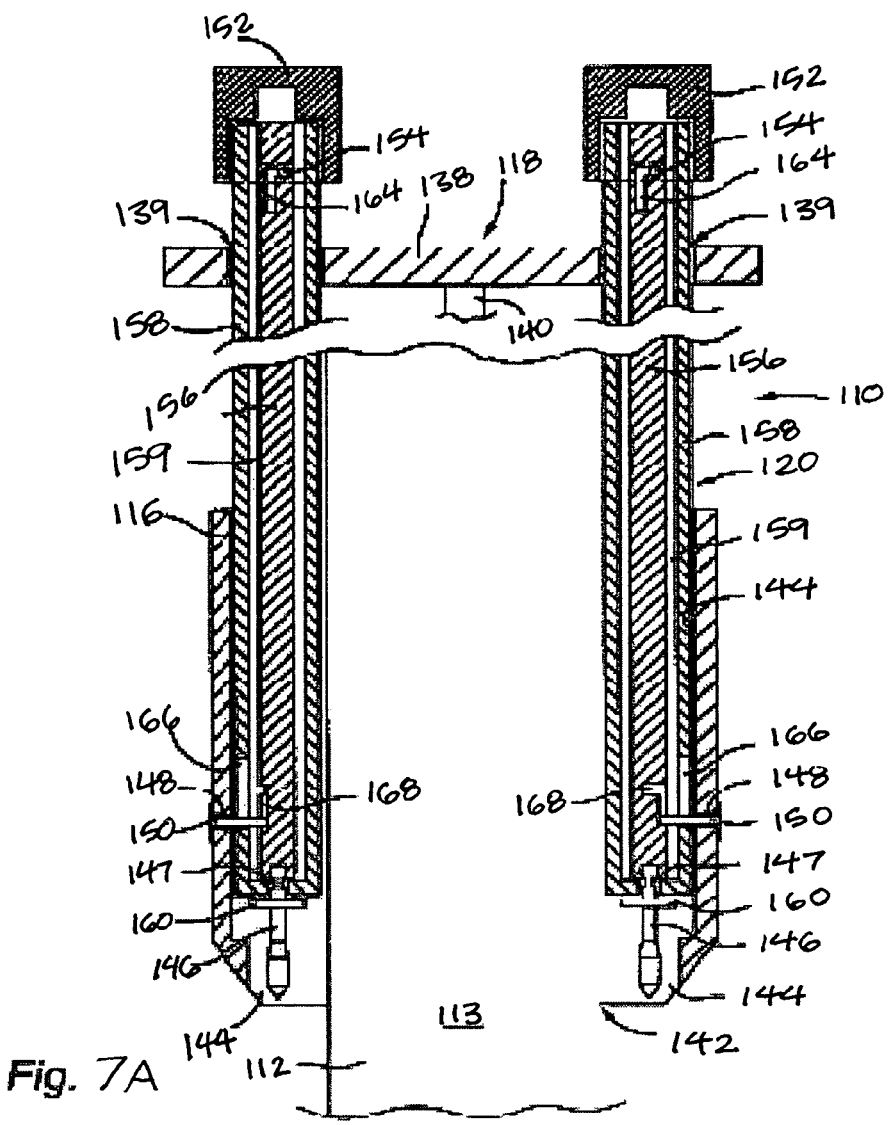
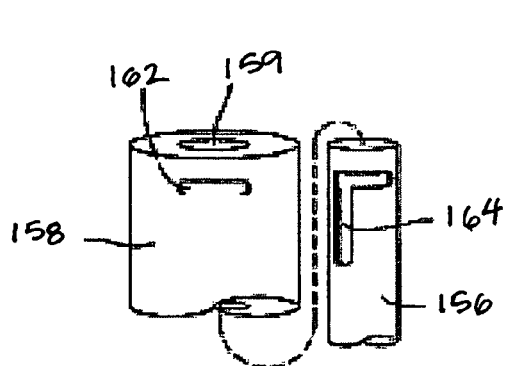
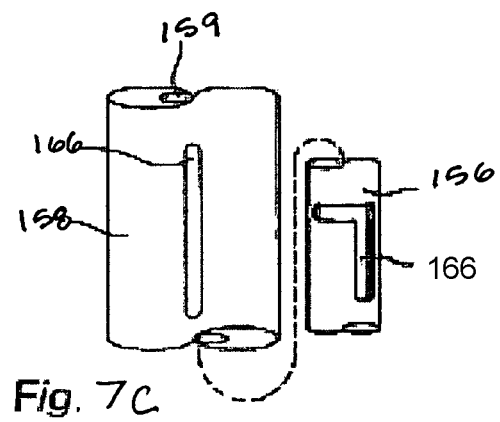
Fig. 7A
Fig. 7B
Fig. 7C

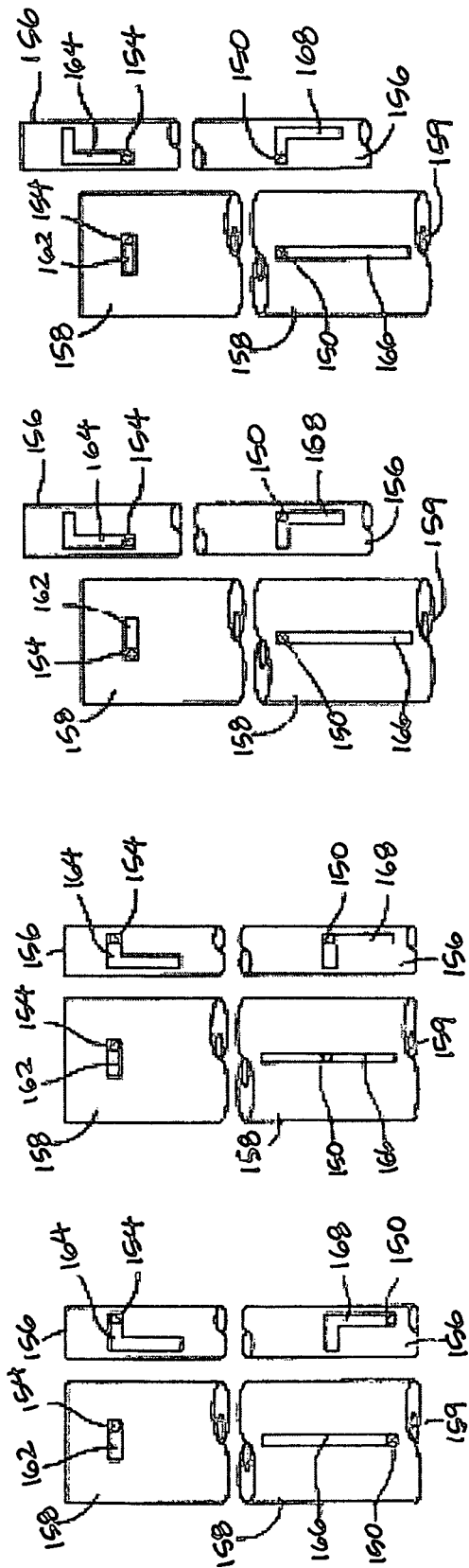

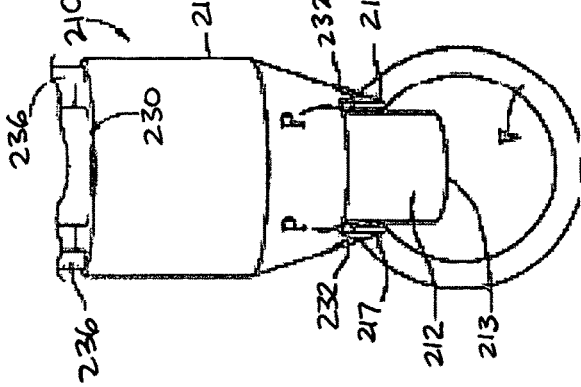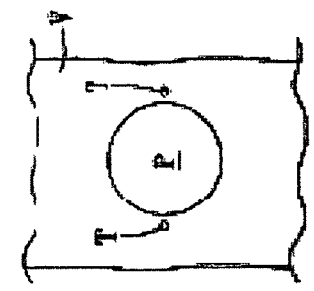
Fig. 16A    Fig. 16B
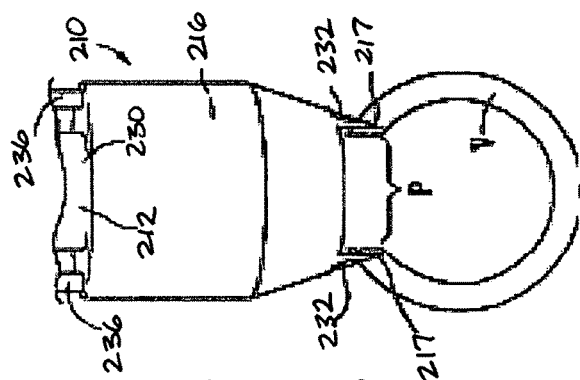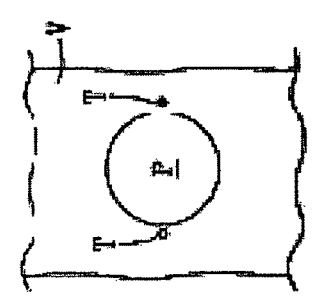
Fig. 17A    Fig. 17B
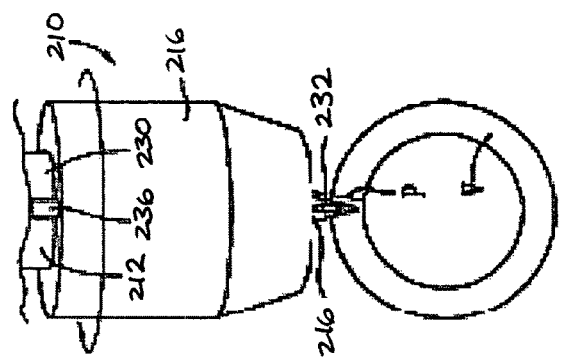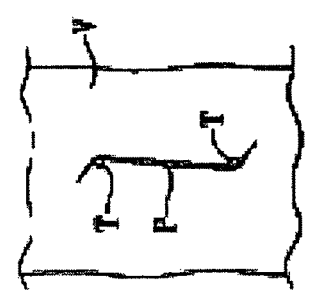
Fig. 18A    Fig. 18B
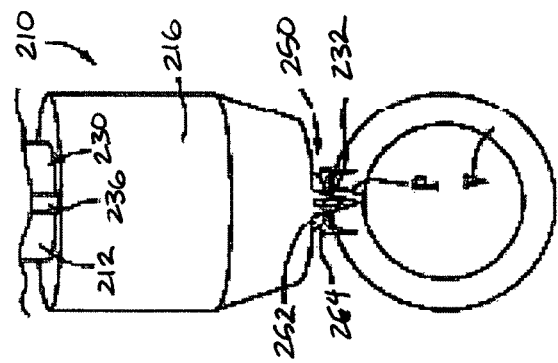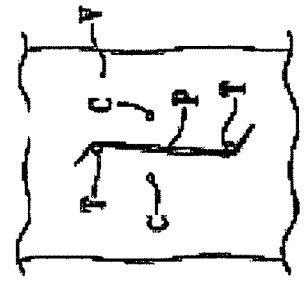
Fig. 19A    Fig. 19B

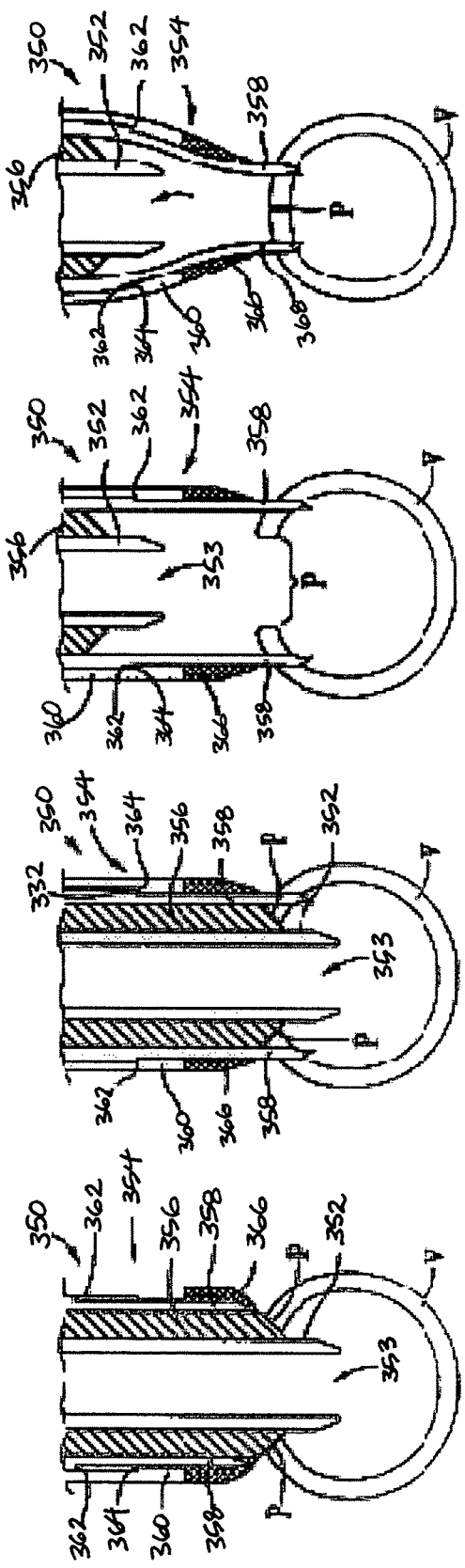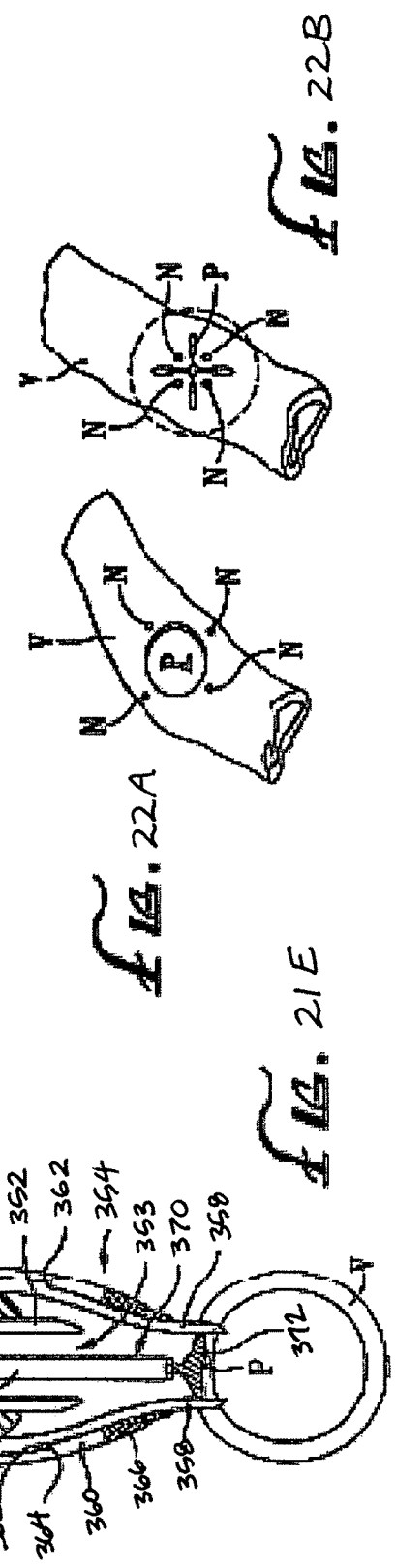

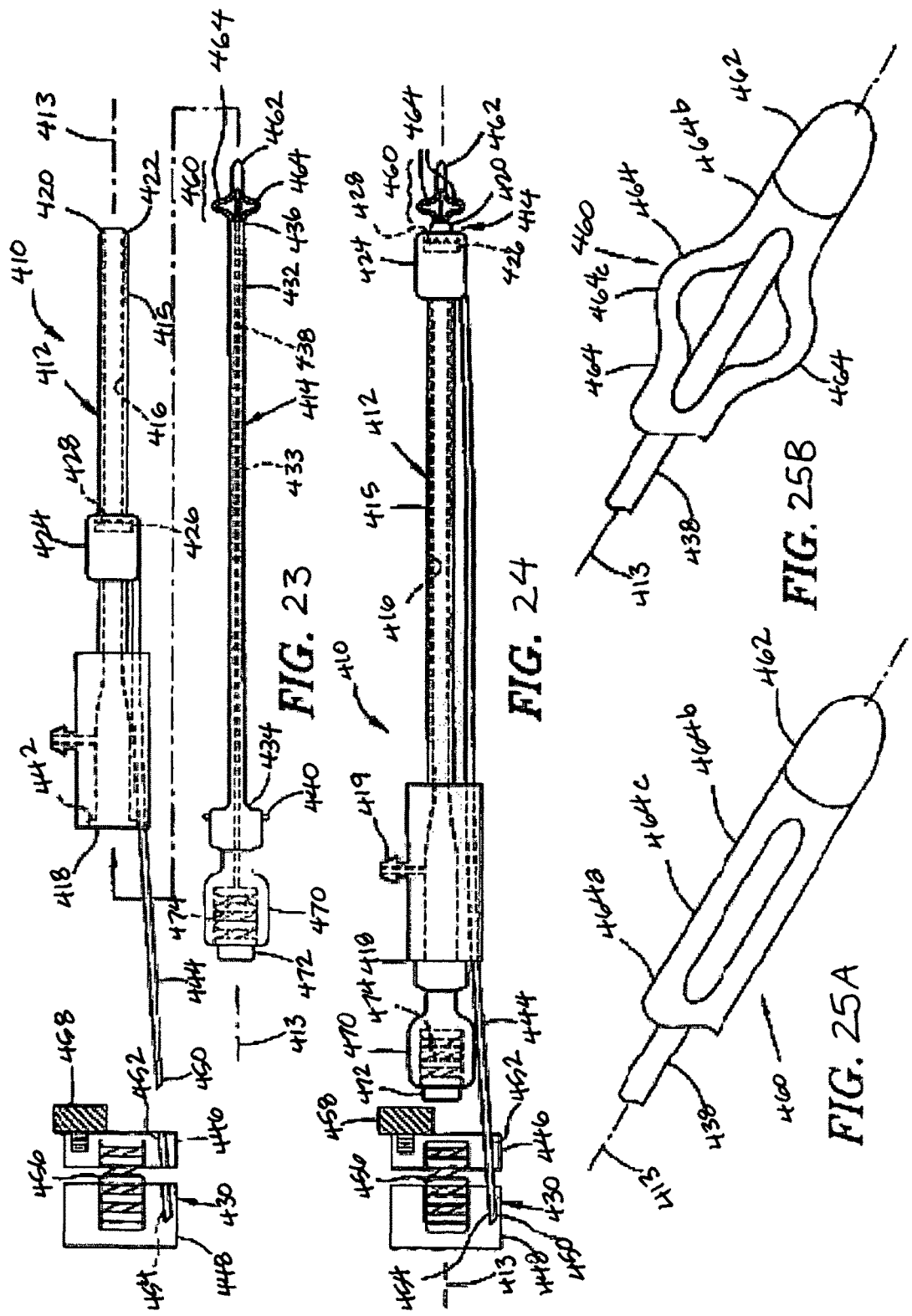

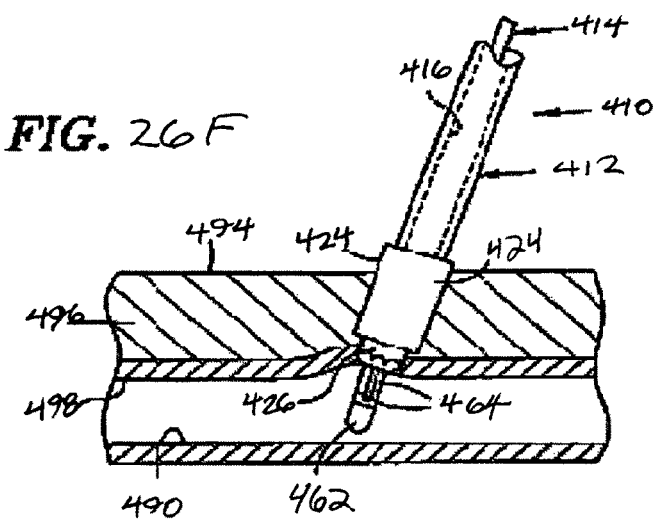
FIG. 26F
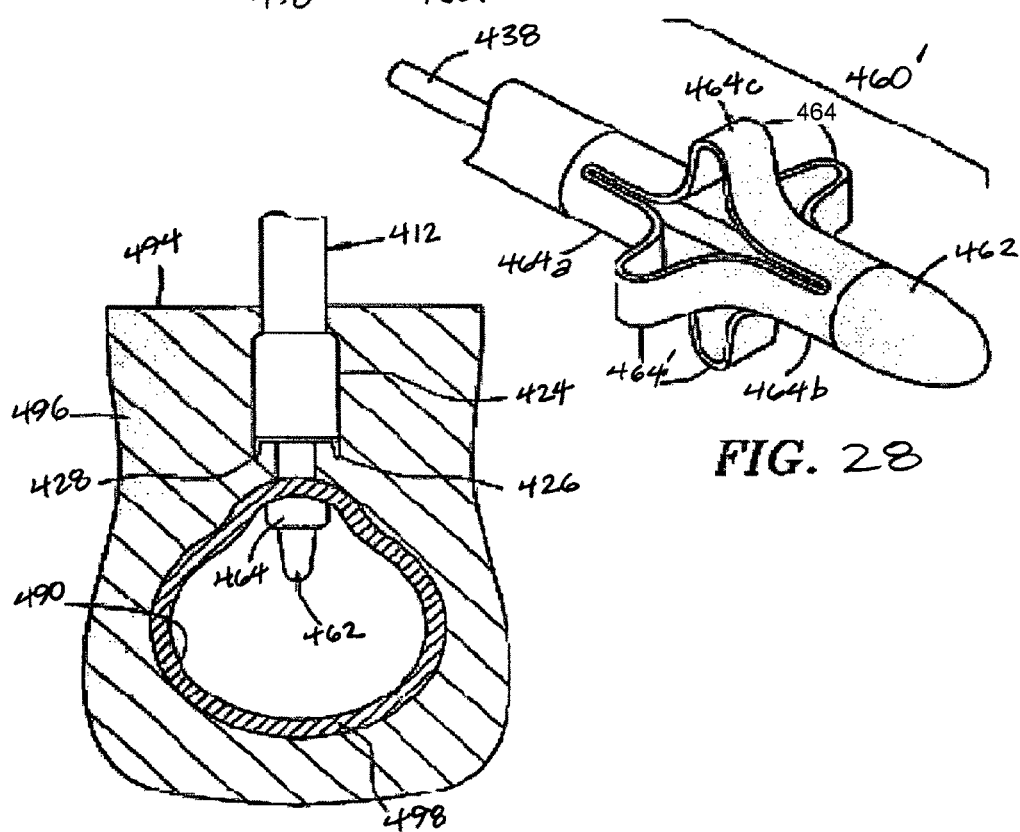
FIG. 28
FIG. 27

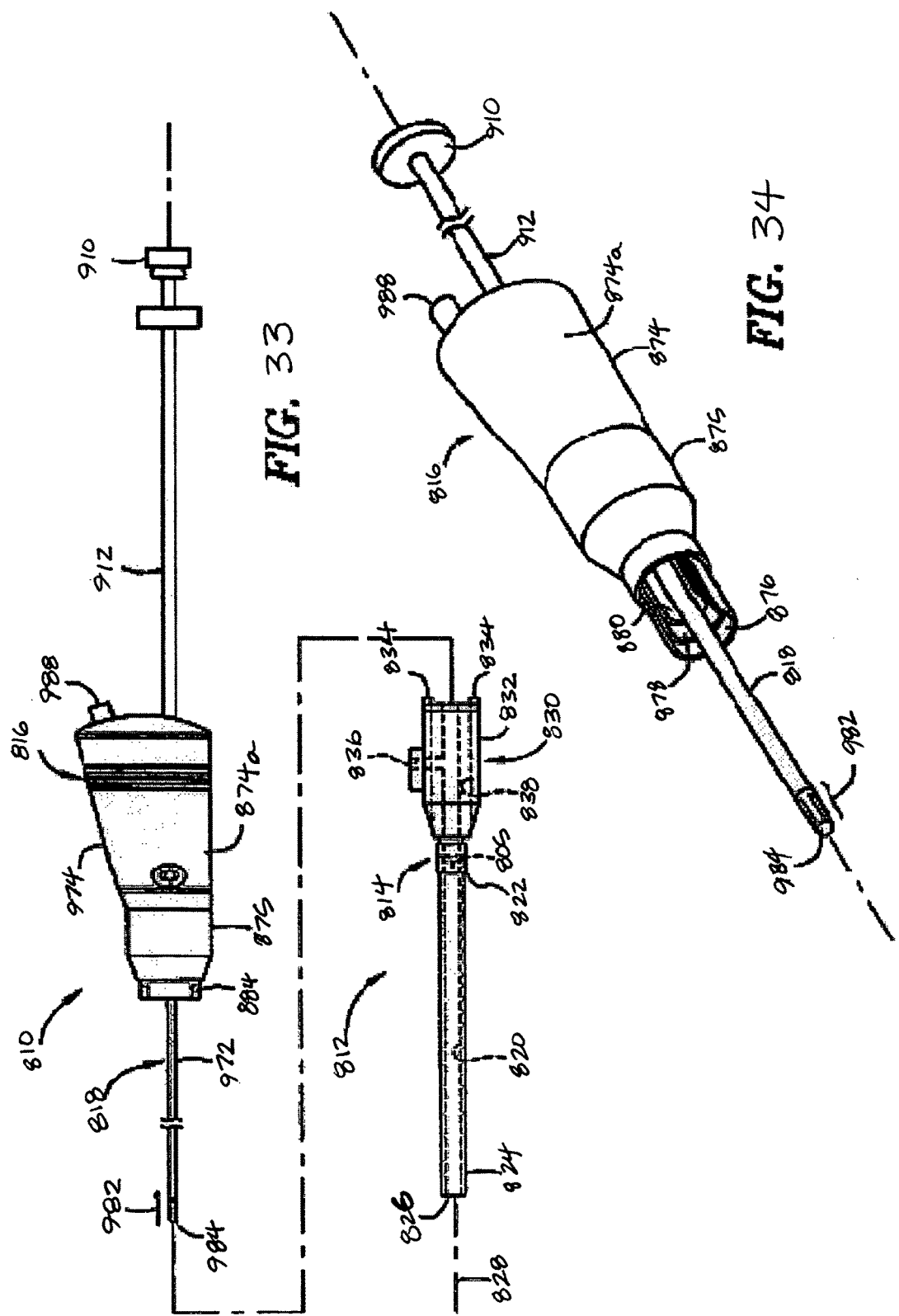

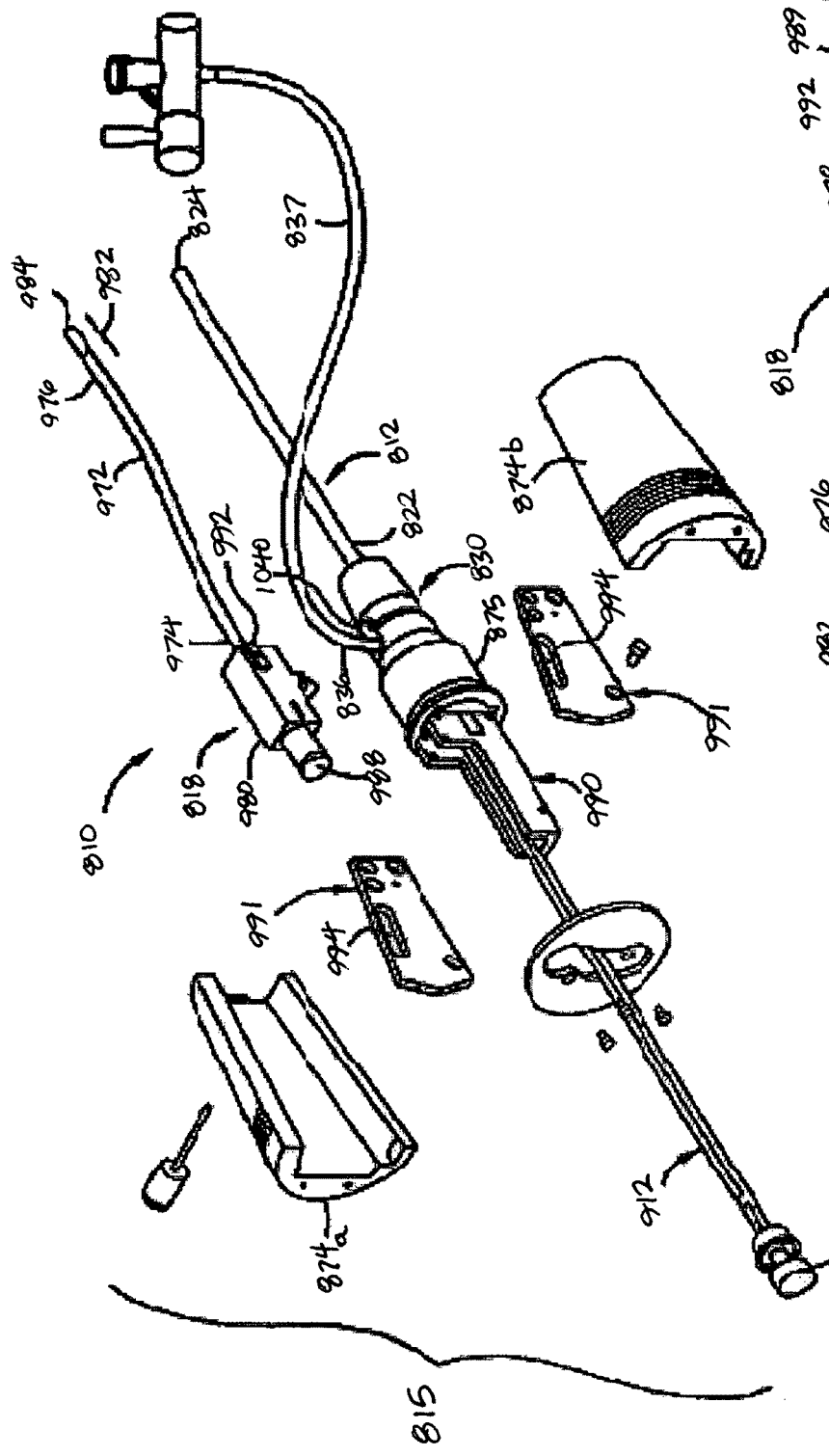
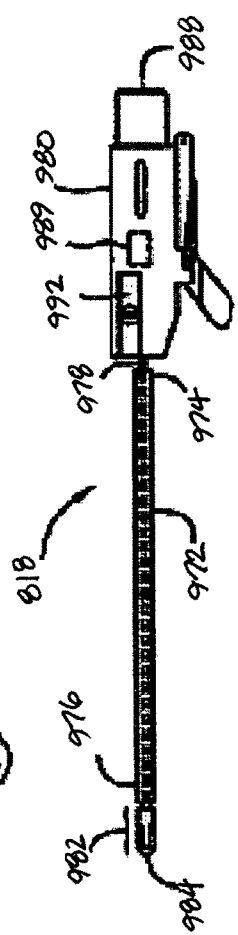
FIG. 35A
FIG. 35B

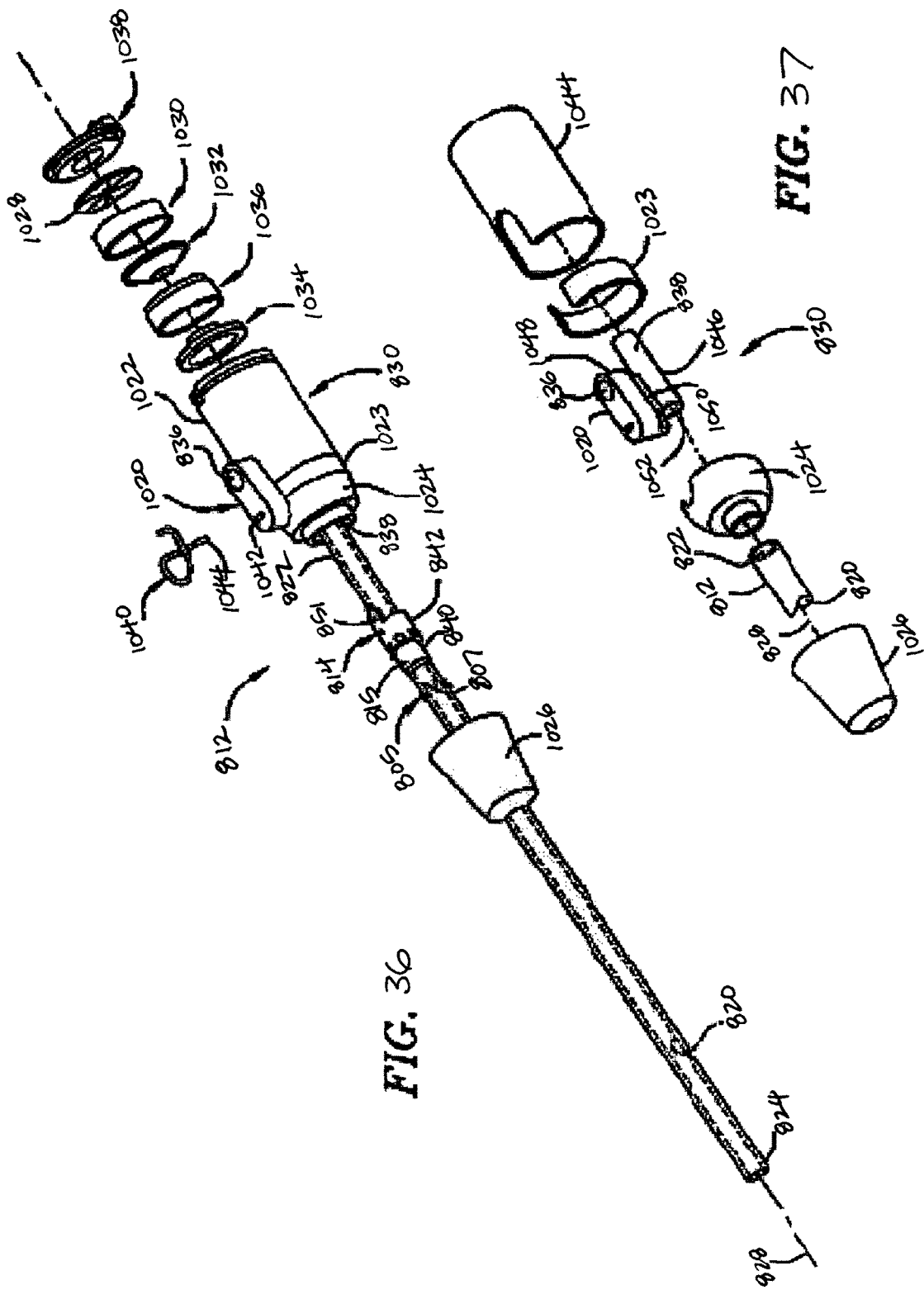

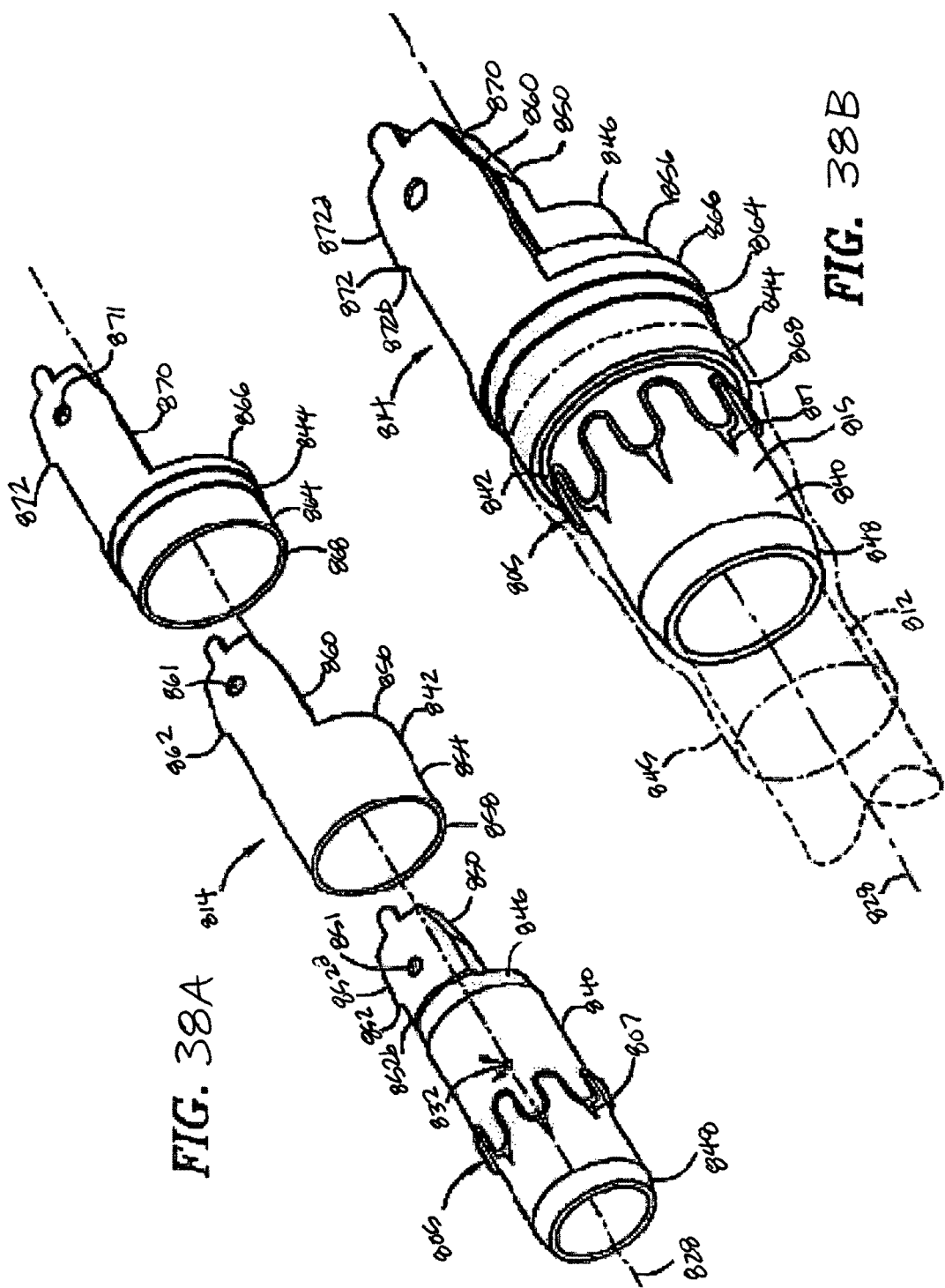

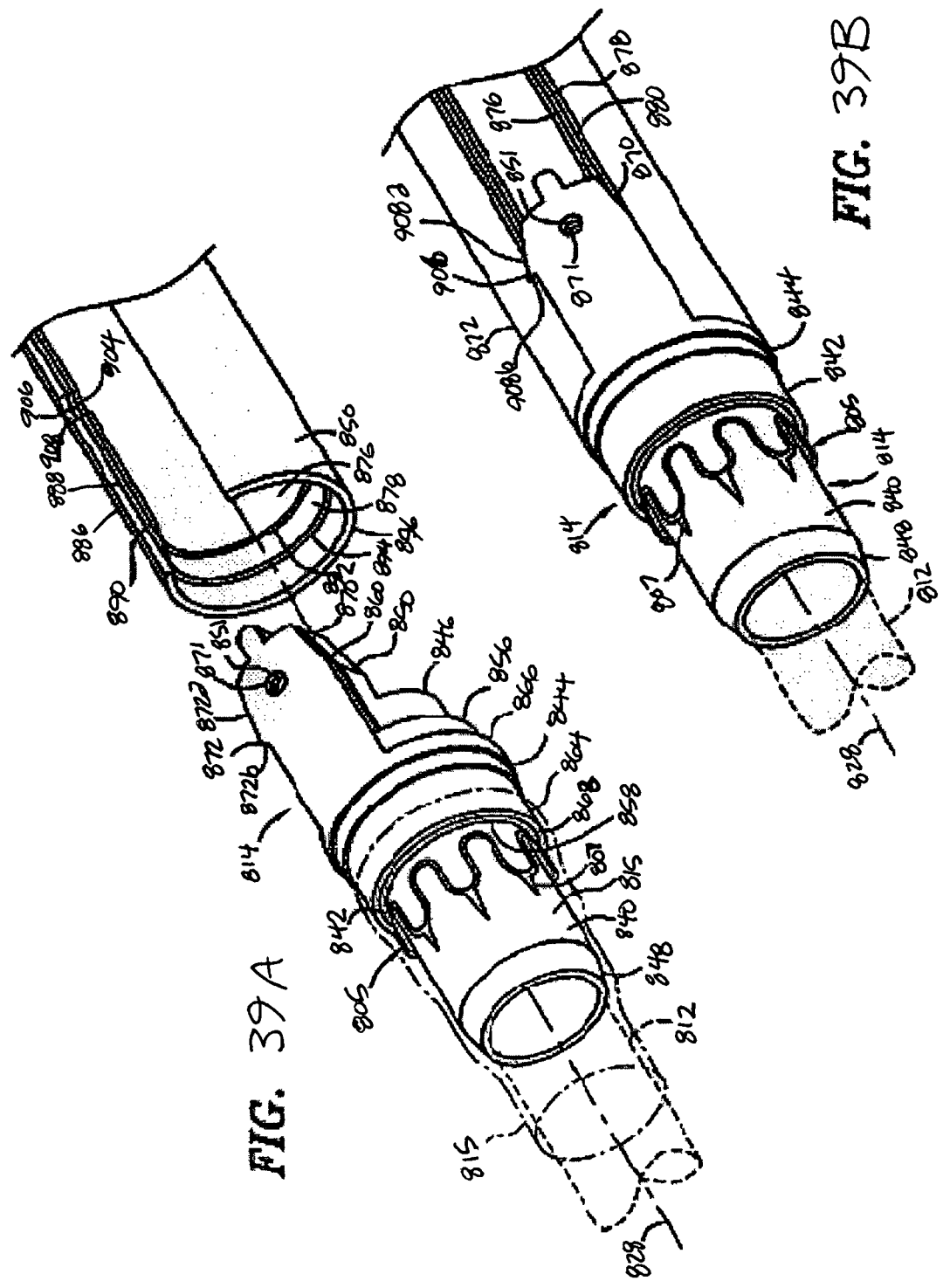

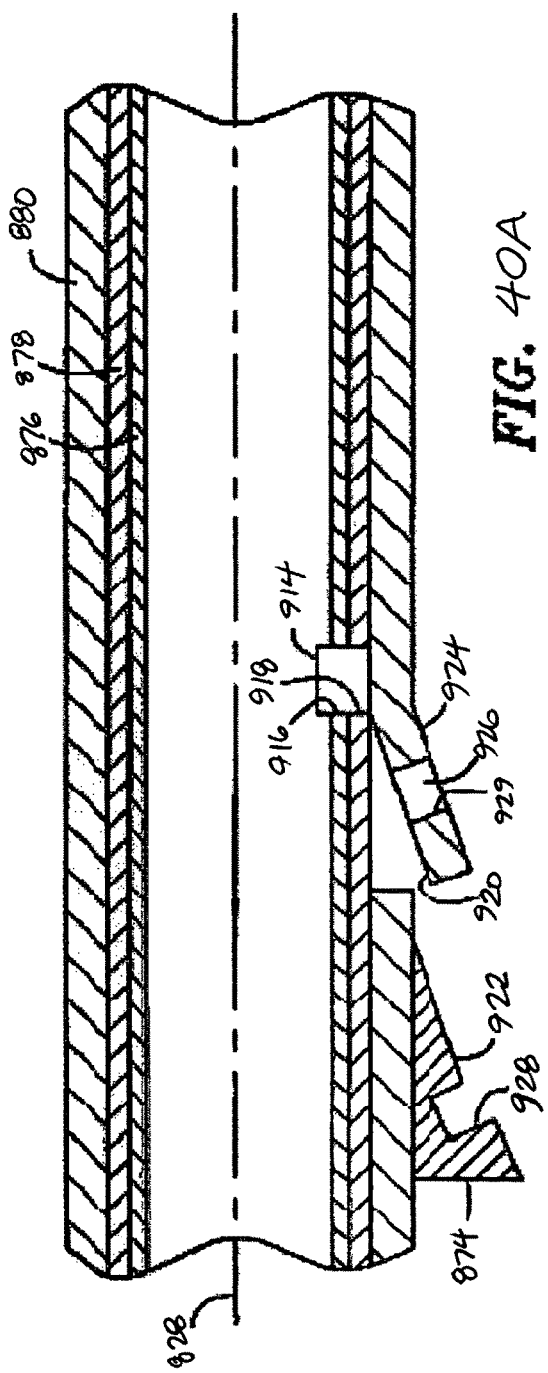
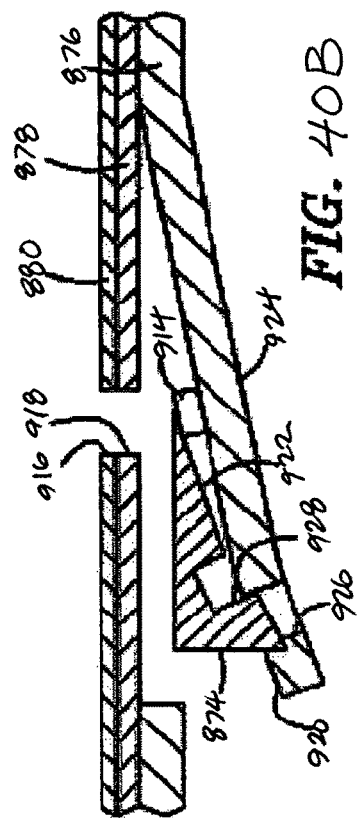
FIG. 40A
FIG. 40B

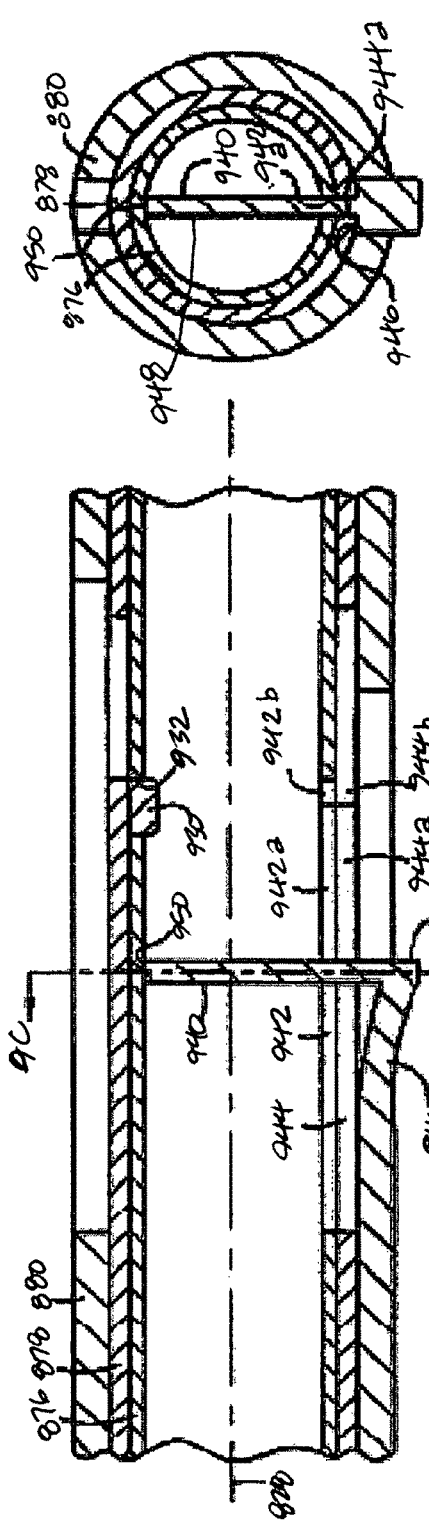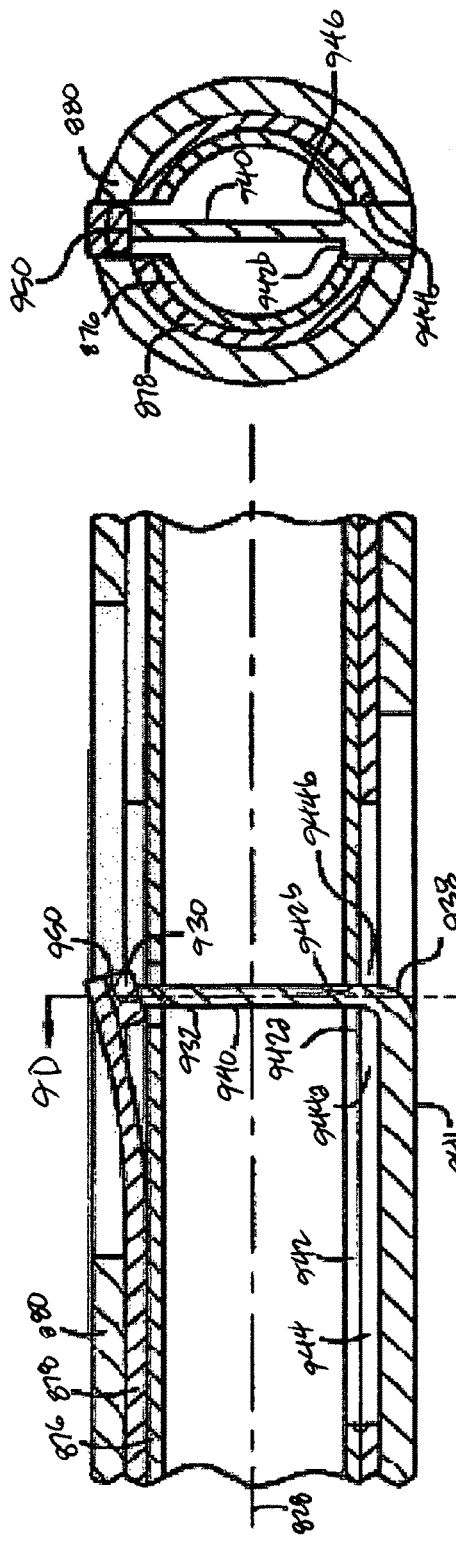

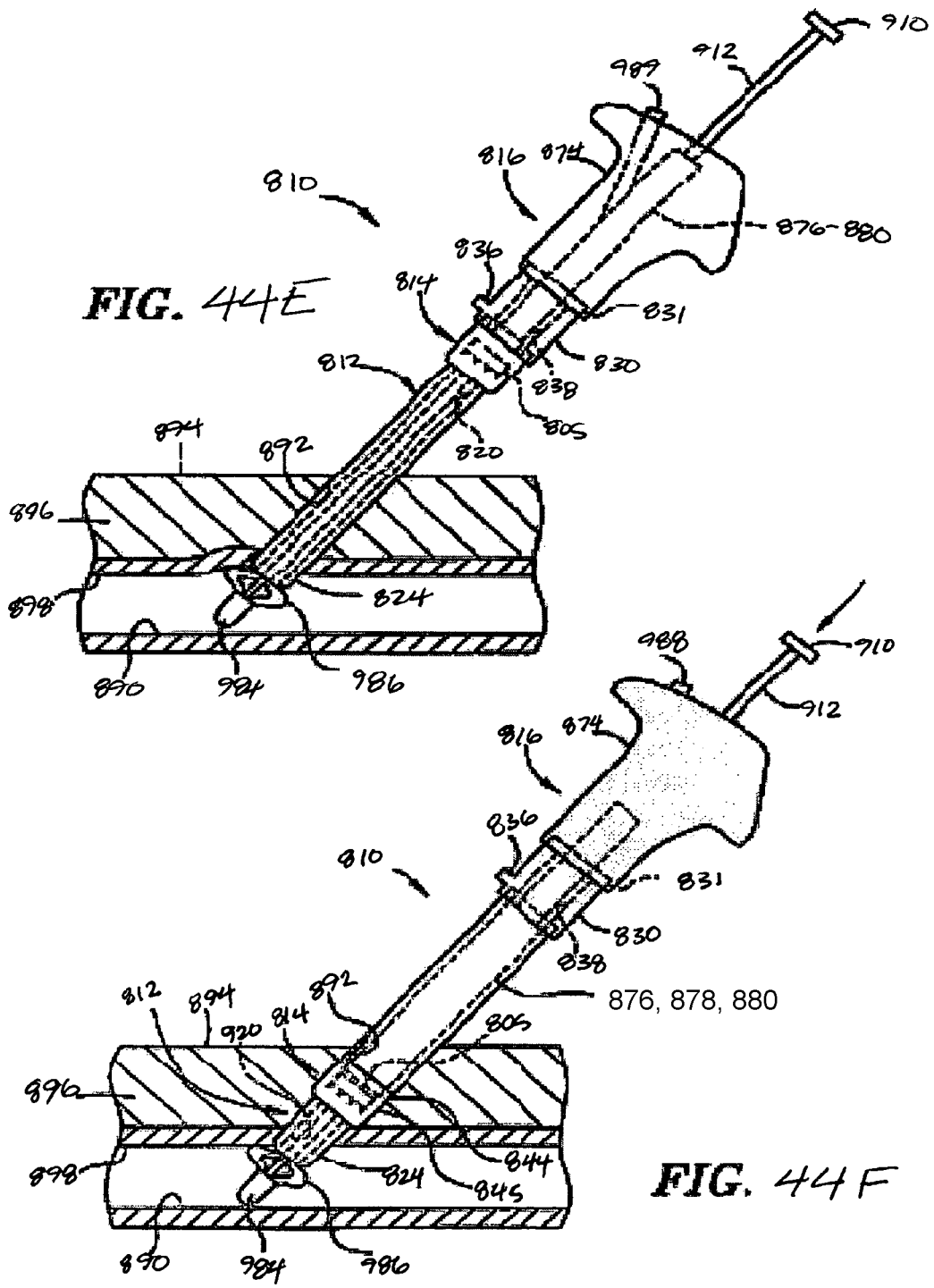

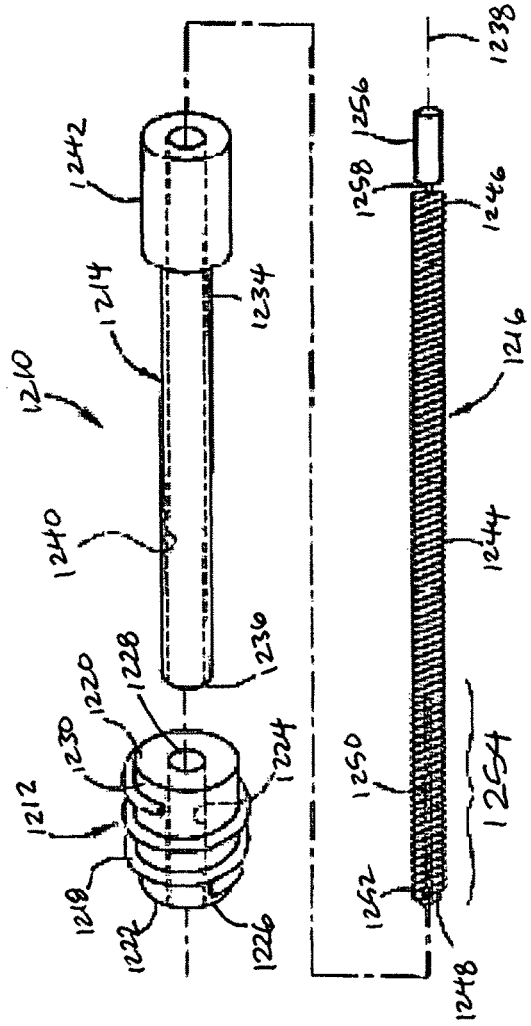
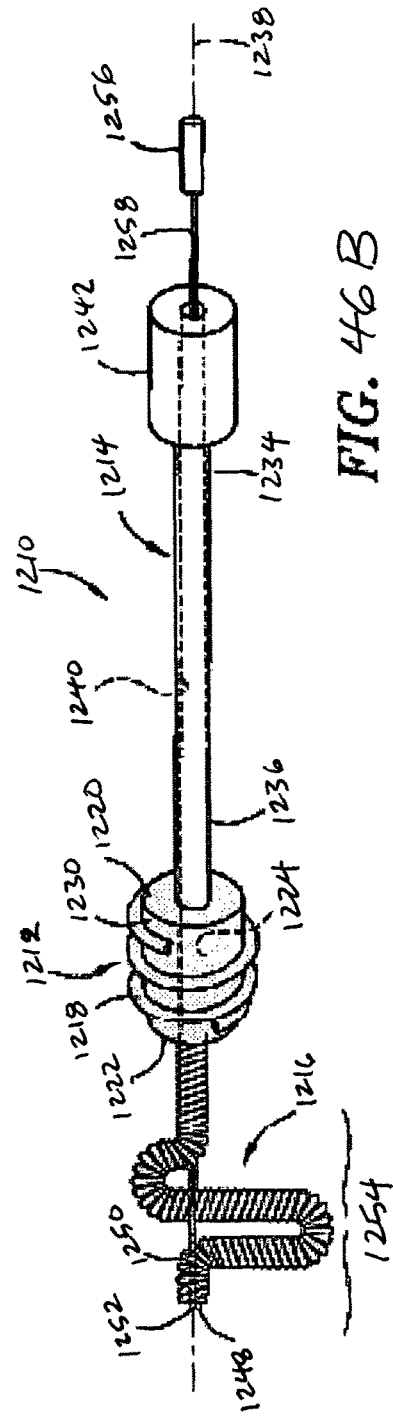
FIG. 46A
FIG. 46B

CLOSURE SYSTEM AND METHODS OF USE

CROSS-REFERENCE TO RELATED APPLICATIONS

This U.S. Patent Application is a continuation-in-part of U.S. application Ser. No. 10/264,306, filed Oct. 3, 2002, now U.S. Pat. No. 7,901,428, which is a continuation of U.S. patent application Ser. No. 09/546,998, filed Apr. 11, 2000, now U.S. Pat. No. 6,461,364, which is a continuation-in-part of U.S. patent application Ser. No. 09/478,179, filed Jan. 5, 2000, now U.S. Pat. No. 6,197,042. Additionally, this U.S. Patent Application is a continuation-in-part of U.S. application Ser. No. 11/198,811, filed Aug. 4, 2005, now U.S. Pat. No. 7,828,817, which is a continuation of U.S. patent application Ser. No. 10/081,723, filed Feb. 21, 2002, now U.S. Pat. No. 6,942,674, which is a continuation-in-part of U.S. patent application Ser. No. 09/732,835, filed Dec. 7, 2000, now U.S. Pat. No. 6,780,197, which is a continuation-in-part of U.S. patent application Ser. No. 09/610,238, filed Jul. 5, 2000, now U.S. Pat. No. 6,391,048, which is a continuation-in-part of U.S. patent application Ser. No. 09/478,179, filed Jan. 5, 2000, now U.S. Pat. No. 6,197,042. Also, this U.S. Patent Application is a continuation-in-part of U.S. application Ser. No. 10/006,400, filed Nov. 30, 2001, now U.S. Pat. No. 7,842,068, which is a continuation-in-part of U.S. patent application Ser. No. 09/732,835, filed Dec. 7, 2000, now U.S. Pat. No. 6,780,197, which is a continuation-in-part of U.S. patent application Ser. No. 09/610,238, filed Jul. 5, 2000, now U.S. Pat. No. 6,391,048, which is a continuation-in-part of U.S. patent application Ser. No. 09/478,179, filed Jan. 5, 2000, now U.S. Pat. No. 6,197,042. This U.S. Patent Application is also a continuation-in-part of U.S. patent application Ser. No. 10/147,774, filed May 17, 2002, now U.S. Pat. No. 7,931,669, which is a continuation-in-part of U.S. patent application Ser. No. 09/610,238, filed Jul. 5, 2000, now U.S. Pat. No. 6,391,048, which is a continuation-in-part of U.S. patent application Ser. No. 09/478,179, filed Jan. 5, 2000, now U.S. Pat. No. 6,197,042. All foregoing patents and applications are incorporated herein by reference.

BACKGROUND OF THE INVENTION

1. The Field of the Invention

The present invention relates to apparatus and methods for sealing an iatrogenic puncture in a vessel or other body lumen formed in conjunction with a diagnostic or therapeutic treatment. More particularly, the present invention provides apparatus comprising an introducer sheath including a puncture site closure device comprising an expandable clip with elastic memory. Also, the present invention provides apparatus comprising an introducer sheath including a puncture site closure device comprising a bioabsorbable clip. Further, the present invention includes an apparatus and methods for positioning such a device relative to the body lumen before delivery

2. The Relevant Technology

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurser's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al., describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel. Moreover, the agents used to occlude the puncture site are animal-derived, typically collagen-based. Thus, a risk of adverse immunoresponse exists.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, such devices employing resilient clips or staples have been developed. U.S. Pat. No. 5,478,354 to Tovey et al. describes the use of resilient clips in conjunction with a trocar to close abdominal puncture wounds. U.S. Pat. No. 5,810,846 to Vimich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft, having a distal end formed with one or more opposed pairs of resilient grasping prongs, that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site. Both of the devices described in the foregoing patents have the drawback that a separate device must be deployed through the introducer sheath to close the puncture site, thus prolonging the procedure. Moreover, both devices require relatively complex apparatus and involve time consuming manipulation to achieve hemostasis.

The use of back bleed indication as a positioning technique within a vascular puncture is known. For example, U.S. Pat. No. 4,317,445 to Robinson describes a flashback chamber for providing visual indication of venous entry of a cannula. However, that device does not discuss vascular wound closure. U.S. Pat. No. 5,676,689 to Kensey et al., which claims priority from the U.S. Pat. No. 5,222,974 discussed above, uses a vessel location device to simplify positioning of the biodegradable plug. The vessel locator enables blood from the vessel to flow there through so that the position of the vessel may be determined. However, the Kensey system only proffers one closure device, and that device is complex and raises concerns about biocompatibility. It also requires the closure component to be positioned within the puncture, thereby increasing the likelihood of dangerous over-advancement of the plug into the vessel.

The percutaneous puncture closure devices described in the foregoing patents generally have the drawback that they require relatively complex mechanisms and require time consuming manipulation to achieve hemostasis. It therefore would be desirable to provide apparatus and methods suitable for vascular puncture closure that overcome these disadvantages of previously known devices. It also would be desirable to provide apparatus and methods for vascular puncture closure that quickly and effectively achieve hemostasis. It further would be desirable to provide vascular puncture closure apparatus and methods that do not require the introduction of additional apparatus at the completion of the catheterization procedure to achieve closure. It still further would be desirable to provide apparatus and methods suitable for vascular puncture closure that do not introduce animal-derived material into the bloodstream. It still further would be desirable to provide apparatus and methods wherein all foreign materials left in a patient's body are bioabsorbable.

BRIEF SUMMARY OF THE INVENTION

Generally, embodiments of the present invention can include medical devices and methods of using the same for closing an opening in a body tissue. Such methods can include the following: positioning a closure clip in a first closure clip position adjacent to the opening in the body tissue such that a plurality of spikes of the closure clip are inserted into the tissue at a location outward from a central axis of the opening; and positioning the closure clip in a second closure clip position such that the plurality of spikes are pulled inward toward the central axis of the opening so as to pull the tissue between the opening and each of the spikes together and close the opening. Additionally, the closure clip can be released from a distal end of a closure clip applicator when adjacent to the opening in the tissue. This can be facilitated when the closure clip applicator is positioned adjacent to the opening in the body tissue by using a sheath such that the sheath guides the positioning of the applicator.

Moreover, the sheath can be positioned relative to the opening in the tissue with a guide before the closure clip applicator is positioned adjacent to the opening. During positioning of the sheath, the guide can have a distal portion that extends through the opening of the body tissue and a proximal portion that can be disposed within a lumen of the sheath. This can allow for the guide to center the sheath at the central axis of the opening, which in turn can facilitate the sheath centering the spikes of the closure clip around the opening of the tissue with respect to the central axis when the closure clip is in the second position.

Another embodiment of a method of closing an opening in a body tissue can include the following: positioning a closure clip applicator adjacent to the opening in the body tissue, the closure clip applicator having a closure clip in a radially expanded position at a distal end of the closure clip applicator; positioning the radially expanded closure clip into a first closure clip position adjacent to the opening in the body tissue such that a plurality of spikes of the closure clip are inserted into the tissue at a location outward from a central axis of the opening; and contracting the radially expanded closure clip to a second closure clip position such that the plurality of spikes are pulled inward toward to central axis of the opening so as to pull the tissue between the opening and each of the spikes together and close the opening. Additionally, the closure clip can be released from a distal end of the closure clip applicator when adjacent to the opening in the tissue. This can be facilitated when the closure clip applicator is positioned adjacent to the opening in the body tissue by using a sheath such that the sheath guides the positioning of the applicator.

Moreover, the sheath can be positioned relative to the opening in the tissue with a guide before the closure clip applicator is positioned adjacent to the opening. During positioning of the sheath, the guide can have a distal portion that extends through the opening of the body tissue and a proximal portion that can be disposed within a lumen of the sheath. This can allow for the guide to center the sheath at the central axis of the opening, which in turn facilitates the sheath centering the spikes of the closure clip around the opening of the tissue with respect to the central axis when the closure clip is in the second position.

Yet another embodiment of a method of closing an opening in a body tissue can include the following: inserting a guide through the opening in the body tissue; using the guide to position a closure clip applicator adjacent to the opening in the body tissue with the guide, the closure clip applicator having a closure clip in a radially expanded position at a distal end of the closure clip applicator; positioning the radially expanded closure clip into a first closure clip position adjacent to the opening in the body tissue such that a plurality of spikes of the closure clip are inserted into the tissue at a location outward from a central axis of the guide; and contracting the radially expanded closure clip to a second closure clip position such that the plurality of spikes are pulled inward toward to central axis of the guide so as to pull the tissue between the opening and each of the spikes together and close the opening. Additionally, the closure clip can be released from the distal end of a closure clip applicator when adjacent to the opening in the tissue. This can be facilitated when the closure clip applicator is positioned adjacent to the opening in the body tissue by using a sheath such that the sheath guides the positioning of the applicator.

Moreover, the sheath can be positioned relative to the opening in the tissue with the guide before the closure clip applicator is positioned adjacent to the opening. During positioning of the sheath, the guide can have a distal portion that extends through the opening of the body tissue and a proximal portion that can be disposed within a lumen of the sheath. This can allow for the guide to center the sheath at the central axis of the opening, which in turn can facilitate the sheath centering the spikes of the closure clip around the opening of the tissue with respect to the central axis when the closure clip is in the second position.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings.

FIGS. 3A-3D are side views of the resilient clip of the present invention shown from different angles in an expanded delivery configuration and in an unstressed deployed configuration.

FIGS. 4A and 4B are isometric views of an alternative embodiment of the resilient surgical clip, constructed in accordance with the present invention and shown, respectively, in an unstressed deployed configuration and in an expanded delivery configuration.

FIGS. 7A-7C are, respectively, a cross-sectional view of a closure component of the vascular device of FIG. 6, an exploded side view of proximal slots of the closure component, and an exploded side view of distal slots.

FIGS. 10A-10B through 13A-13B are side-sectional views of the closure component of FIG. 7A in use at a vascular puncture site, with corresponding side views of the proximal and distal slots of FIGS. 7B and 7C, illustrating a method of sealing the puncture site with the present invention.

FIGS. 16A-16B through 19A-19B are side views of the closure component of FIG. 14 in use at a vascular puncture site, shown in section, with the sealing device of FIG. 15, illustrating a method of sealing the puncture site, and corresponding top views of the vascular puncture site.

FIGS. 21A-21E are side-sectional views of a further alternative embodiment in use at a vascular puncture site, illustrating a method of sealing the puncture site.

FIGS. 22A and 22B are isometric views of a section of vessel including and corresponding to the vascular puncture site of FIGS. 21A-21E, further illustrating the methods of FIGS. 21A-21E.

FIG. 23 is a side view of an apparatus for delivering a closure element, including an introducer sheath, a locator, and an actuator assembly, in accordance with the present invention.

FIG. 24 is a side view of the apparatus of FIG. 23, with the locator disposed within the sheath, and a housing on the sheath advanced to a delivery position.

FIGS. 25A and 25B are perspective views of the distal end of the apparatus of FIGS. 23 and 24, showing positioning elements on the locator in collapsed and expanded configurations, respectively.

FIGS. 26A-26F are cross-sectional views of a blood vessel, showing a method for delivering a closure device into a passage communicating with the vessel.

FIG. 27 is a cross-sectional view of the blood vessel of FIG. 26D, showing the positioning elements engaging a wall of the vessel.

FIG. 28 is a perspective view of an alternate embodiment of a distal portion of the locator with the positioning elements disposed in their expanded configuration.

FIG. 33 is an exploded side view of a first preferred embodiment of an apparatus for delivering a closure element, including an introducer sheath, and an actuator assembly, in accordance with the present invention.

FIG. 34 is a perspective view of the actuator assembly for the apparatus of FIG. 33.

FIG. 35A is an exploded perspective view of the apparatus of FIG. 33.

FIG. 35B is a side of view of an obturator assembly for the actuator assembly of FIGS. 33-34A.

FIG. 36 is a partially exploded perspective view of the introducer sheath shown in FIGS. 33 and 35A.

FIG. 37 is an exploded perspective view of a hub assembly of the introducer sheath shown in FIG. 36.

FIG. 38A is an exploded perspective view of a carrier assembly, including a carrier member, a pusher member, and an anchor member, for use with the apparatus of FIGS. 33-37.

FIG. 38B is a perspective view of the carrier assembly of FIG. 38A, with the carrier, pusher, and anchor members assembled substantially coaxially with respect to one another.

FIGS. 39A and 39B are perspective views of the carrier assembly of FIGS. 38A and 38B aligned with and attached to a distal end of the actuator assembly of FIG. 33, respectively.

FIGS. 40A and 40B are cross-sectional details of telescoping tubular members of the actuator assembly of FIGS. 33-35B, showing cooperating detents for releasably coupling an outer tubular member to inner and intermediate tubular members.

FIGS. 41A-41D are cross-sectional details of the telescoping tubular members of FIGS. 40A and 40B, showing cooperating detents for releasably coupling the inner and intermediate tubular members.

FIGS. 44A-44H are cross-sectional views of a blood vessel, showing a method for delivering a clip into an interstitial region of a passage communicating with the vessel.

FIG. 46A is an exploded perspective view of an apparatus for delivering, a closure device, including the locator device of FIGS. 45A and 45B.

FIG. 46B is a perspective view of the apparatus of FIG. 46A after assembly, and with the locator device deployed.

DETAILED DESCRIPTION OF THE PREFERRED EMBODIMENTS

Figure 2:
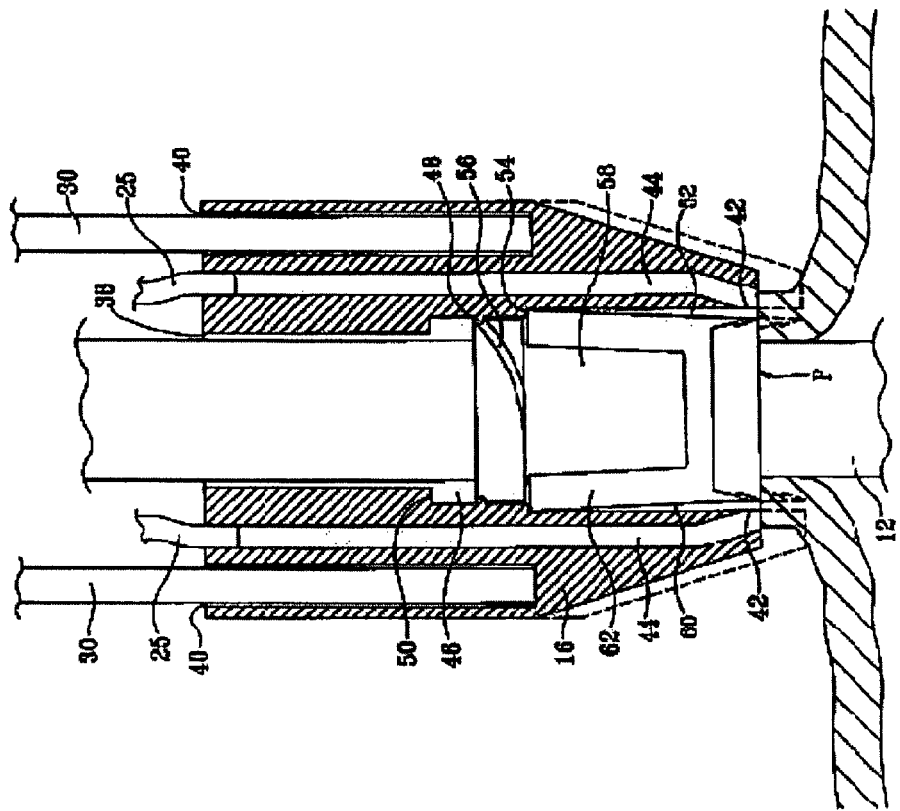
FIG. 2 is a cross sectional view of the closure component of the vascular device of FIG. 1.

Generally, the present invention can provide vascular puncture closure apparatus and methods that overcome disadvantages of previously known devices. Also, the invention can provide apparatus and methods suitable for vascular puncture closure that quickly and effectively achieve hemostasis. Additionally, the invention can provide apparatus and methods for vascular puncture closure that do not require the introduction of additional apparatus at the completion of the catheterization procedure to achieve closure. Further, the invention can provide vascular puncture closure apparatus and methods that do not introduce animal-derived material into the bloodstream. Furthermore, the invention can provide apparatus and methods wherein all foreign materials left in a patient's body are bioabsorbable. Moreover, the invention can provide vascular puncture closure apparatus and methods that are safe, lower cost, and easy to use.

I. Closure Systems

Generally, the present invention can include a medical instrument for wound closure. As such, the invention can include a vascular introducer sheath having an integrated wound closure component. The closure component consists of a resilient spring clip disposed on and advanceable over the exterior of the introducer sheath in an expanded delivery configuration until opposite sides of the clip pierce a vessel on opposite sides of a puncture site. The introducer sheath is then withdrawn, enabling the spring clip to contract to its unstressed deployed configuration, thereby drawing opposite sides of the puncture together and closing the wound. Means also are provided for confirming when the spring clip has engaged the vessel wall, thereby indicating to the surgeon that the clip may be deployed and the introducer sheath may be withdrawn. Alternative embodiments of the spring clip also are provided.

Additionally, the closure component can consist of a bioabsorbable and deformable clip with a bioabsorbable fastener and is disposed on and advanceable over the exterior of the introducer sheath in an expanded delivery configuration until opposite sides of the clip pierce a vessel on opposite sides of a puncture site. The clip is then mechanically deformed with the fastener into a deployed configuration, thereby drawing opposite sides of the puncture together and closing the wound. Means also are provided for confirming when the bioabsorbable clip has engaged the vessel wall to indicate to the surgeon that the clip may be deployed and the introducer sheath may be withdrawn.

In a preferred embodiment, the bioabsorbable clip resembles an inverted "Y" with pointed ends that puncture the vessel to be closed. The fastener comprises a bioabsorbable locking collar that may be advanced down the length of the clip to bring the pointed ends together.

In another embodiment, the bioabsorbable clip comprises a hoop with pointed legs extending therefrom. The hoop has two points of reduced thickness spaced 180 degrees apart on the circumference of the hoop. The fastener comprises a bioabsorbable conical wedge that is pushed down into the hoop to force opposing sides of the hoop towards one another and bring the pointed legs together.

In another embodiment, the present invention includes an integrated vascular device comprising a sheath having a puncture closure component and puncture sealant. The closure component is disposed on and advanceable over the exterior of the sheath, which may, for example, comprise an introducer sheath, a trocar, or a catheter. The closure component may comprise any of a variety of apparatus suited to close a vascular puncture. Once the closure component has been actuated to close the puncture, sealant is introduced to the exterior surface of the closed puncture, preferably through the sheath's interior lumen, where the sealant seals the puncture closed. The sheath with closure component is then removed from the patient.

In a preferred embodiment constructed in accordance with the present invention, the closure component comprises a twist closure device. The device pierces tissue surrounding the vascular puncture and then is rotated to close the wound. In an alternative embodiment, the closure component comprises needles and an elastic segment surrounding the needles. The needles pierce the puncture with the elastic segment expanded. The segment is then allowed to resiliently contract to an unstressed configuration of smaller diameter, thereby drawing the needles together and closing the wound.

In a still further alternative embodiment, the needles, or prongs, are elastically deformed to an expanded diameter, in which they pierce the tissue adjacent to puncture. The needles then are allowed to resiliently contract to an unstressed configuration of smaller diameter, thereby closing the wound.

Sealant then may be introduced, preferably through the interior lumen of the sheath, to seal the puncture closed. The sealant may comprise any of a variety of sealants, per se known, including adhesives, sutures, and clips, all of which are preferably bioabsorbable. Alternatively, the closure component may further comprise the sealant, wherein the closure component is left in place within the vessel until hemostasis naturally occurs, or wherein the closure component comprises a monopolar electrode or opposed bipolar electrodes that cauterize the wound with RF current. In addition to cauterization, RF energy generates heat that beneficially causes shrinkage of the vascular tissue, thereby assisting closure of the wound. Thermal energy from electrical induction, infrared light, ultrasonic vibration, microwave or laser irradiation, and other means may also be used to seal the puncture.

In one embodiment, an apparatus is provided for delivering a closure element into engagement with tissue adjacent an opening into a body lumen. The apparatus includes a sheath including a lumen extending between its proximal and distal ends, and a locator member disposed within the sheath, the locator member having a distal portion extending distally beyond the distal end of the sheath. One or more positioning elements are provided on the distal portion of the locator member, the positioning elements being selectively expandable between a substantially axial collapsed configuration and a substantially transverse expanded configuration. Preferably, the positioning elements are a plurality, e.g. two or more, equally spaced, substantially flexible splines or wings configured for expanding substantially transversely to a longitudinal axis of the sheath. Each spline may have a first fixed end and a second movable end, the second end being axially movable towards the first end to cause an intermediate region of the spline to expand radially outward, thereby defining the radially expanded configuration. Alternatively, the splines may include a plurality of substantially rigid or semi-rigid elements that are hinged such that the splines may be expanded to the expanded configuration.

An actuator may be coupled to the locator member, the actuator configured for controllably expanding the positioning elements from the collapsed configuration to the expanded configuration. The actuator may include a control such that the positioning elements may be selectively expanded to one of a plurality of expanded sizes, e.g., to accommodate insertion into vessels of various sizes.

A housing may be axially slidably disposed on an exterior of the sheath, the housing configured for releasably holding a closure element, the housing being actuable for advancing the closure element distally to deploy the closure element. In a preferred embodiment, the locator actuator may be configured for automatically collapsing the positioning elements to the collapsed configuration upon advancement of the housing to prevent engagement between the closure element and the positioning elements. The housing may be substantially permanently but slidably disposed on the sheath. Alternatively, the housing may be provided separate from the sheath, e.g., with the closure element pre-loaded therein. The housing may be directed over the sheath, e.g., over the proximal end of the sheath, at any time before delivery of the closure element.

In another embodiment, a method is provided for delivering a closure element into a passage communicating with an opening in a wall of a body lumen. An introducer sheath is positioned through a patient's skin towards the body lumen via the passage, the sheath including a lumen extending between its proximal and distal ends. One or more instruments may be introduced through the lumen of the sheath into the body lumen. A diagnostic or therapeutic procedure may be performed using the one or more instruments at a location accessed via the body lumen.

In a preferred embodiment, the body lumen is a blood vessel, such as a peripheral vessel, e.g., the femoral or carotid artery. The procedure may be any of a variety of endovascular procedures, such as angioplasty, atherectomy, stent delivery, delivery of a therapeutic agent, and tissue ablation. Upon completion of the procedure, the devices may be removed from the sheath. A locator may be inserted along or through the sheath until a distal portion of the locator extends beyond the distal end of the sheath and into the body lumen. One or more positioning elements on the distal portion of the locator may be expanded from a collapsed configuration to an expanded configuration. The sheath and locator may then be manipulated with respect to the body lumen until the positioning elements in their expanded configuration contact the wall of the body lumen, thereby providing a tactile indication of a location of the distal end of the sheath. A closure element may then be delivered via the sheath into the passage. The sheath and locator may be withdrawn from the body lumen and opening, leaving the closure element to substantially close the opening.

In one embodiment, an apparatus is provided for delivering a closure element or other annular-shaped device into an opening through tissue, e.g., for engaging tissue adjacent to the opening to close and/or seal the opening. The apparatus includes an elongate member including proximal and distal ends, such as an introducer sheath that includes a lumen for advancing one or more devices into a body lumen during a procedure.

A carrier assembly is slidable on the elongate member, the carrier assembly including an inner carrier member, a middle pusher member, and, optionally, an outer skin, nested together. Each member may have an annular shape, and may include a connector on its proximal end. The pusher member may be disposed about the carrier member to define a space distal to the pusher member along an outer surface of the carrier member. The outer skin has a length, whereby the outer skin may extend over the space and/or contact an outer surface of the elongate member. In a preferred embodiment, the outer skin extends a short distance beyond a distal end of the carrier member, such that the outer skin is slidable along the elongate member. An annular-shaped element, e.g., a clip or other closure device, may be received on the carrier member within the space, the annular-shaped element being deployable from the space upon distal movement of the pusher member relative to the carrier member.

In addition, the apparatus may include an actuator assembly including a housing and inner, intermediate, and outer actuator members that telescope relative to the housing and/or to each other. The housing may be connectable to the proximal end of the elongate member, e.g., to a hub on the proximal end by cooperating connectors on the hub and the housing. Each actuator member may include a connector on its distal end for engaging a respective member of the carrier assembly, thereby coupling movement of the carrier, pusher, and sheath members to the inner, intermediate, and outer actuator members, respectively. If the outer skin is eliminated from the carrier assembly, the outer actuator member may be eliminated from the actuator assembly.

In a preferred embodiment, the actuator assembly includes a control member that is coupled to one or more of the actuator members, preferably, but not necessarily, the intermediate actuator member. The inner, intermediate, and outer actuator members may include cooperating detents for coupling distal movement of the inner, intermediate, and outer actuator members together in a predetermined manner as the control member is directed distally.

For example, a first set of cooperating detents may be provided that initially couples the inner, intermediate, and outer actuator members together, and releases the outer actuator member upon attaining a first distal position. The inner and intermediate actuator members may be directed distally further, consequently permitting the carrier and/or pusher members to be directed distally relative to the outer skin. In an exemplary embodiment, the first set of cooperating detents may include a first detent on the outer tubular member and first pockets in the inner and intermediate tubular members for receiving the first detent therein. Cooperating ramps may be provided on the outer tubular member that are configured for disengaging the first detent from the first pockets upon attaining the first distal position, thereby allowing the inner and intermediate tubular members to be directed distally beyond the first distal position.

In addition, the cooperating detents may include a second set of cooperating detents on the inner and intermediate actuator members for coupling movement of the inner and intermediate actuator members together to a second distal position distal to the first distal position. For example, the intermediate actuator member may include a second detent, and the inner actuator member may include a second pocket for receiving the second detent therein. The housing or the outer actuator member may include a spring element for disengaging the second detent from the second pocket upon attaining the second distal position. For example, the spring element may include a beam extending from the outer tubular member through slots in the inner and intermediate tubular members, the beam being received in the second pocket upon attaining the second distal position, thereby disengaging the second detent and allowing further distal movement of the intermediate member while substantially simultaneously coupling the inner and outer tubular members together.

The intermediate actuator member may be advanced distally beyond the second distal position by directing the control member further distally, thereby directing the pusher member distally with respect to the carrier member to deploy the annular-shaped element from the space.

In addition, the actuator assembly may also include an obturator or locator member that may be part of the actuator assembly or may be connected to the actuator assembly. A distal portion of the locator member may extend distally beyond the actuator members. In addition, the locator member has sufficient length such that the distal portion may extend beyond the distal end of the elongate member when the actuator assembly is connected to the elongate member. One or more positioning elements on the distal portion of the locator member may be movable from a collapsed configuration towards a transversely expanded configuration. A locking mechanism on the locator member and/or actuator assembly may releasably retain the positioning elements in the expanded configuration.

In a preferred embodiment, the locator member is substantially permanently attached to the actuator assembly such that the distal portion extends through and beyond the inner actuator member. Alternatively, the actuator assembly may include a tubular portion or recess communicating via an interior of the inner actuator member with a lumen of the elongate member. In this embodiment, the locator member may be inserted into the tubular portion until the positioning elements are disposed beyond the distal end of the elongate member. One of the inner, intermediate, and outer actuator members may include a third detent for engaging a release mechanism for disengaging the locking mechanism on the locator member. Thus, the positioning elements may be collapsed to the collapsed configuration upon advancing one of the inner, intermediate, and/or outer actuator members, preferably the intermediate actuator member, to its final distal position.

In one embodiment, a closure element is associated with the elongate member for sealing the passage. In a preferred embodiment, the closure element is a plug member disposed on the distal end of the elongate member. The plug member may include a thread pattern on its outer surface, and may include a distal port communicating with a passage therethrough that, in turn, communicates with the lumen in the handle device. A sealing member may be provided in the passage for substantially sealing the passage from fluid flow therethrough. The plug member is preferably releasably attached to the distal end of the elongate member, e.g., by one or more connectors on the distal end of the elongate member and/or on the plug member. Alternatively, the closure element may be a clip that is deployable from the elongate member, e.g., from a housing slidably disposed on the elongate member. A locator member is provided that may be inserted through the lumen, the locator member having a distal portion that extends distally beyond the distal end of the elongate member when the locator member is fully inserted into the lumen. If the closure element is a plug member, the distal portion also extends beyond the plug member, e.g., through the passage therein. The locator member includes an elongate deflectable element including a proximal end and a distal end, and a control element coupled to the distal end of the deflectable element. The control element is movable proximally for causing an intermediate portion of the deflectable element, e.g., the distal portion of the locator member, to buckle substantially transversely with respect to the longitudinal axis. In a preferred embodiment, the deflectable element is a helically wound wire and the control member is a tether extending along at least the intermediate portion of the helically wound wire. The tether may extend within the helically wound wire and/or along an outer surface of at least a portion of the helically wound wire. Preferably, the intermediate portion of the deflectable element has a cross-section in its buckled configuration that is larger than a cross-section of the lumen, thereby preventing the deflectable element from being withdrawn into the plug member and/or elongate member once activated.

In another embodiment, a method is provided for sealing a passage communicating with a body lumen using an apparatus, such as that described above. The apparatus generally includes an elongate member including proximal and distal ends, and a closure element deployable from the distal end of the elongate member.

A locator member is coupled to the elongate member such that a distal portion of the locator member extends beyond the distal end of the tubular member. For example, if the elongate member is an introducer sheath or other tubular member including a lumen, the locator member may be inserted into the lumen. The distal end of the elongate member is advanced through a patient's skin towards the body lumen via the passage until the distal portion of the locator member is located within the body lumen. For example, if the closure element is a plug member, the elongate member may rotated to thread the plug member into the passage towards the body lumen.

A deflectable element on the distal portion of the locator member is buckled from an axial collapsed configuration to a transverse expanded configuration. The elongate member is manipulated such that the buckled distal portion engages or otherwise contacts a proximal wall of the body lumen, thereby providing a tactile indication of the location of the distal end of the elongate member relative to the body lumen.

The closure device is then deployed from the distal end of the elongate member within the passage. The elongate member and the locator member are then withdrawn from the passage, leaving the closure element to substantially seal the opening. Preferably, the deflectable element of the locator member includes a helically wound wire, and a tether or other control member coupled to a distal end of the helically wound wire. The tether may be subjected to tension, e.g., directed proximally, to buckle the helically wound wire substantially transversely, thereby defining the transverse configuration.

In a preferred embodiment, the closure element is a plug member releasably coupled to the distal end of the elongate member and including an external thread pattern. If the elongate member is a tubular member, the plug member may include a distal port communicating with the lumen in the tubular member, such that the locator member may be inserted into the tubular member until the distal portion extends through the distal port of the plug member. The distal portion is inserted into the passage until the plug member enters the passage, whereupon the plug member is threaded into the passage until the distal portion of the locator member enters the body lumen. The distal portion may be activated, as described above, and used to provide tactile feedback to position the plug member. For example, the plug member may be at least partially unthreaded before the plug member is deployed within the passage.

In an alternative embodiment, the apparatus may be used in conjunction with an introducer sheath or other tubular member already in place within the passage, e.g., that is used to access the body lumen during a procedure. The locator member may be inserted through the tubular member until the distal portion of the locator member is located within the body lumen. The deflectable element on the distal portion of the locator member may be buckled from an axial collapsed configuration to a transverse expanded configuration. The locator member may be manipulated, e.g., pulled proximally, such that the buckled distal portion engages or otherwise contacts a proximal wall of the body lumen, thereby providing a tactile indication that the distal portion is disposed within the body lumen and/or limiting further proximal movement of the locator member.

A plug member (or other closure device) may then be advanced over the locator member into the passage. For example, the plug member, disposed on the distal end of an elongate member, may be threaded through the tissue along the passage over the locator member. Preferably, the locator member is inserted through the distal port of the plug member and/or through the lumen of the elongate member as the plug member is advanced. Once the plug member attains a desired location within the passage, the plug member may be released from the distal end of the elongate member within the passage. The distal portion of the locator member may be returned to its axial configuration, and the elongate member and the locator member may be withdrawn from the passage, leaving the plug member to substantially seal the opening To facilitate positioning of the plug member, the locator member may include one or more markers, e.g., disposed on a proximal portion, that may have a predetermined relation with the distal portion of the locator member. For example, the proximal portion of the locator member may include a marker band located a predetermined distance from the distal portion. The elongate member may include a window for observing the marker when the plug member reaches a predetermined location relative the distal portion, e.g., a predetermined distance proximal to the distal portion. Alternatively, the locator member and the elongate member may include cooperate tactile elements, e.g., tabs and pockets, that engage one another when the plug member reaches a predetermined location. The plug member may then be released at the predetermined location, and then the elongate member and locator member may be removed.

Thus, the various embodiment sof the presnt invention that include an integrated vascular introducer sheath with closure component of the present invention overcome disadvantages associated with previously known methods and apparatus for sealing a vascular puncture by providing a quick, simple, safe, lower cost, effective, and easy-to-use solution to wound closure. A closure device and system constructed in accordance with the present invention provide vascular introduction and wound closure in a single device, eliminating the time and manipulation required to insert a separate closure device at the completion of a procedure. Various embodiments of such a closure device and system are described in more detail below.

II. First Closure System Embodiment

Figure 1:
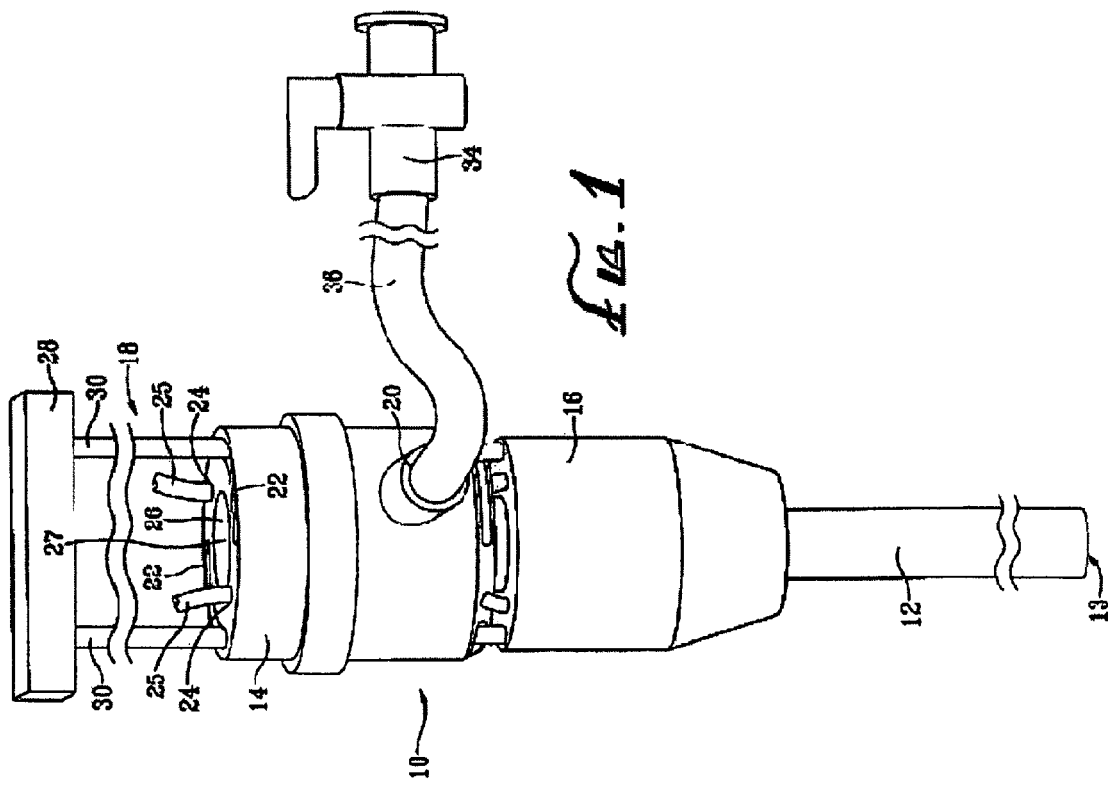
FIG. 1 is a side view of a vascular device constructed in accordance with the present invention.

Referring to FIG. 1, vascular device 10 comprises introducer sheath 12 coupled to hub 14, clip housing 16, and clip actuator 18. Introducer sheath 12 comprises a material typically used for vascular introducer sheaths, such as polyethylene or nylon, and includes central lumen 13 through which other devices may be introduced in the vasculature, for example, to perform a diagnostic or interventional procedure such as angiography, angioplasty or stenting. Hub 14 is mounted to the proximal end of introducer sheath 12 and includes side port 20, arc-shaped lumens 22, back bleed lumens 24, back bleed tubes 25, and device port 26. Device port 26 communicates with central lumen 13 of introducer sheath 12, and has self-sealing elastomeric membrane 27 disposed across it. Self-sealing membrane 27, which may comprise, e.g., latex or a biocompatible synthetic rubber, permits interventional devices to be introduced through device port 25 while preventing blood loss through central lumen 13. Side port 20 of hub 14 is in communication with central lumen 13, and is connected to hemostatic port 34 via biocompatible tubing 36.

Clip housing 16 includes an annular-shaped chamber that holds a elastically deformable clip. In accordance with the principles of the present invention, clip housing is slidably disposed on the exterior of introducer sheath 12 and is movable from a stowed position, adjacent hub 14, to a distal clip deployment position, where the spring clip is urged into engagement with tissue surrounding vascular puncture.

Clip actuator 18 comprises plunger 28 and rods 30, which are configured to slidably pass through arc-shaped lumens 22 of hub 14. The distal ends of rods 30 are mounted in clip housing 16, so that movement of plunger 28 causes corresponding proximal or distal movement of clip housing 16. As described in detail hereinafter, when plunger 28 is moved to its proximal-most position, clip housing is disposed adjacent to hub 14 and provides adequate clearance for interventional devices to be inserted device port 25 and central lumen 13 into the patient's vasculature. When moved to its distal-most position, plunger 28 causes rods 30 to urge clip housing 16 distally.

Referring now also to FIG. 2, the closure component of vascular device 10 is described in greater detail. Clip housing 16 comprises bore 38 that slidably receives introducer sheath 12, bores 40 in which rods 30 are mounted, and back bleed indicator ports 42. Back bleed indicator ports 42 are coupled to back bleed tubes 25 via lumens 44. Housing 16 further comprises threaded bore 46 with male thread 48 and proximal ledge 50, and clip bore 52 with proximal ledge 54. Threaded bore 46 engages female thread 56 of clip expander 58. Clip expander 58 is slidably disposed on introducer sheath 12, and together with the portion of clip housing 16 surrounding the spring clip 62 forms annular chamber 60.

Spring clip 62 is stored in its expanded delivery configuration in annular chamber 60 so that it slidably passes over clip expander 58 until it abuts proximal ledge 54 of clip bore 52. In a delivery configuration of vascular device 10, the length of annular chamber 60, as measured from the distal end of clip expander 58 to proximal ledge 54, extends within the distal end of clip housing 16 for a sufficient distance to cover the length of clip 62. In this manner, clip housing 16 prevents snagging spring clip 62 from snagging on tissue during advancement of clip housing 16 to its deployed position, as described hereinbelow.

Rods 30 pass through arc-shaped lumens 22 of hub 14 and mounted in bores 40 of clip housing 16. Distal advancement of rods 30 causes clip housing 16, expander 58, and spring clip 62 to advance distally a corresponding distance relative to introducer sheath 12. When plunger 28 is moved to its distal-most position, rods 30 may be rotated within arc-shaped lumens 22 to rotate and advance clip housing 16 relative to clip expander 58. This motion causes clip housing 16 to advance distally along female thread 56 of clip expander 58 until the proximal end of the clip expander contacts proximal ledge 50 of threaded bore 46. Further rotation of rods 30 causes proximal ledge 54 to urge a tissue-engaging portion of spring clip 62 distally off of clip expander 58. With clip housing 16 positioned at a vascular puncture site P, rotation of rods 30 causes the tissue-engaging portion, illustratively spikes, to pierce the vessel wall, as seen in dotted profile in FIG. 2.

In alternative embodiments, plunger 28 and rods 30 may be removably coupled to clip housing 16, to permit unobstructed access to device port 26. In this embodiment, rods 30 may include teeth that may be rotated to fixedly engage bores 40 in clip housing 16.

As discussed hereinabove, back bleed indicator ports 42 are coupled to tubes 25 via blood lumens 44 that extend through clip housing 16. Back bleed tubes 25 are slidably disposed through back bleed lumens 24 of hub 14. When the distal end of clip housing 16 is advanced distally against the vessel wall at puncture P, blood enters blood indicator ports 42 and exits tubes 25, providing visual confirmation to the surgeon that the distal end of clip housing 16 is positioned adjacent to the vessel wall. Back bleed tubes 25 thus enable the surgeon to determine when clip housing 16 has been advanced sufficiently to permit clip deployment, while reducing the risk that the clip is either deployed short of the puncture site or extended into the vessel.

Still referring to FIG. 1, in conjunction with clip deployment, a bioglue or tissue sealant may be delivered through hemostatic port 34, tubing 36, port 20 and central lumen 13 of introducer sheath 12 to vascular puncture P to further help seal the vessel after deployment of clip 62. Alternatively, the bioglue or tissue sealant may be delivered through the back bleed path described above.

Referring now to FIGS. 3A-3D, an illustrative spring clip 62 constructed in accordance with the principles of the present invention is described in greater detail. FIG. 3B is a side view of the clip of FIG. 3A rotated 90 degrees, wherein clip 62 is in an expanded delivery configuration. Clip 62 comprises an annular device having upper members 70 joined to lower members 72 by legs 74 to form lumen 80. Outer spikes 76 and inner spikes 78 are connected to lower members 72, and act as elongated tissue-engaging members. Clip 62 is elastically expanded by advancing introducer sheath 12 or clip expander 58 through lumen 80.

Upon removal of the introducer sheath, spring clip 62 resiliently returns to its unstressed deployed configuration, illustrated in FIGS. 3C and 3D, where FIG. 3C corresponds to the view of FIG. 3A and FIG. 3D corresponds to the view of FIG. 3B. When removed from the exterior of introducer sheath 12, spring clip 62 resumes its deployed shape, in which the opposing sides of the clip come together until lower members 72 contact one another, and outer spikes 76 cross inner spikes 78. As depicted in FIG. 3A, clip 62 also may optionally comprise engagement means 77 to securely engage the vessel being closed. Engagement means 77 may, for example, comprise barbs or hooks.

Clip 62 is preferably fabricated from a superelastic material, such as a nickel-titanium alloy, but may comprise any material with sufficient resilience to elastically expand for delivery over sheath 12 and fit within annular chamber 60 of clip housing 16. Clip 62 also may be fabricated from a bioabsorbable material or a combination bioabsorbable and elastically expandable material.

FIGS. 4A and 4B illustrate an alternative embodiment of the resilient spring clip of the present invention, wherein clip 90 comprises hoop 92 and opposing spikes 94. In FIG. 4A, clip 90 is depicted in the unstressed, deployed configuration, in which opposing spikes 94 contact one another, whereas in FIG. 4B clip 90 is depicted in the expanded, delivery configuration, in which opposing spikes 94 are separated by gap 96. Clip 90 is elastically expanded in a manner similar to clip 62 by advancement over introducer sheath 12, and preferably also is fabricated from the materials described hereinabove.

Figure 5A:
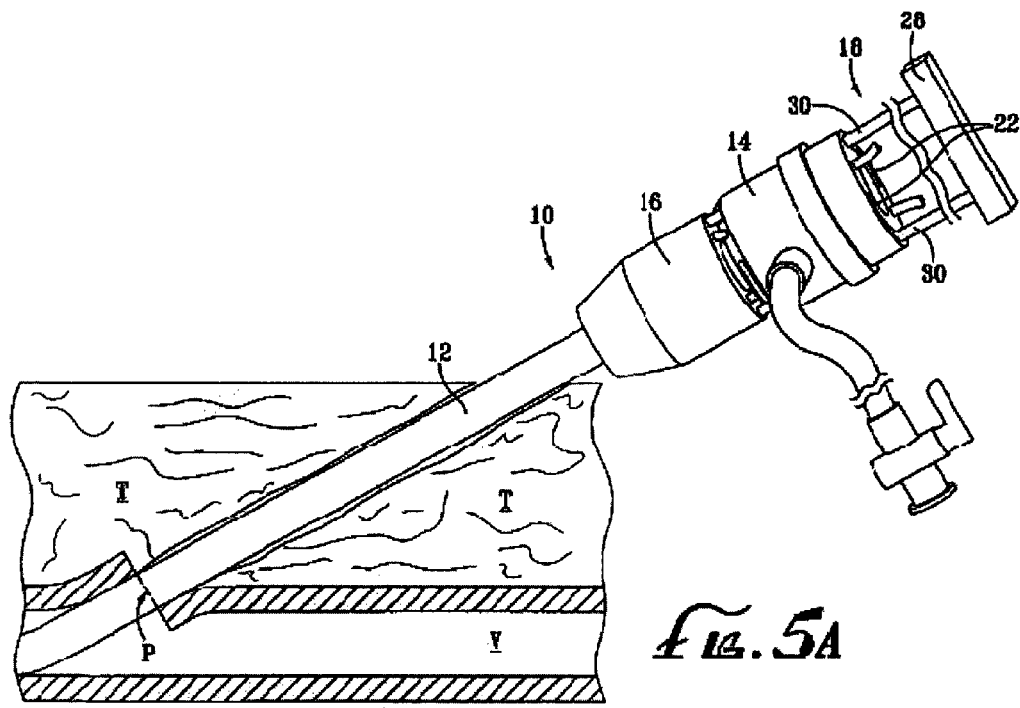
FIGS. 5A-5F are side-sectional views of a vascular puncture site, illustrating a method of sealing the puncture site with the integrated vascular device of FIG. 1.

Referring now to FIGS. 5A-5F, in conjunction with FIGS. 1-3, methods of using vascular device 10 are described. In FIG. 5A, introducer sheath 12 has been advanced through skin, fat, and muscle tissue T into vessel V, through vascular puncture P, which is formed in accordance with well-known techniques. With plunger 28 and rods 30 in the proximal-most, fully retracted position, an interventional procedure then is performed by introducing one or more interventional devices, e.g. angioplasty balloons, stent delivery systems, atherectomy devices, etc., through device port 26 and lumen 13 of introducer sheath 12 in accordance with well-known techniques. Side port 20 may be used to infuse fluids, e.g., contrast agents or medications, into the vessel through introducer sheath 12 during the interventional procedure.

Upon completion of the procedure, vascular device may be advantageously used to close vascular puncture P. At this point, clip actuator 18, housing 16, clip expander 58, and clip 62 are disposed in the proximal-most position adjacent to hub 14, as depicted in FIG. 5A.

Figure 5B:
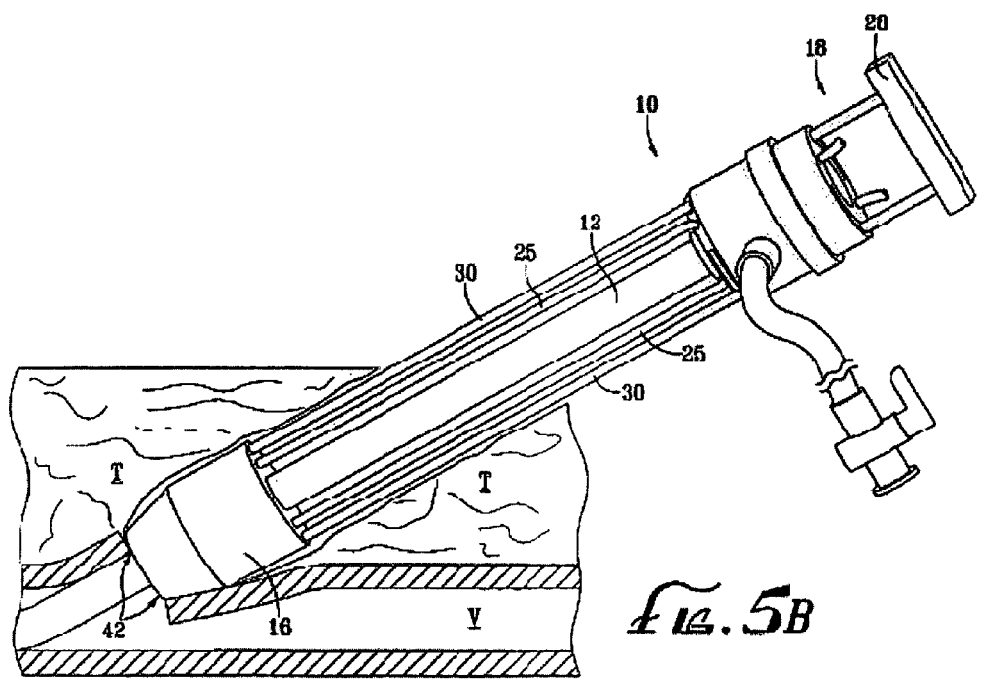

As illustrated in FIG. 5B, clip actuator 18 then is advanced by urging plunger 28 in the distal direction, thus causing rods 30 to slide through arc-shaped lumens 22 of hub 14 and advance clip housing 16. Continued distal advancement of plunger 28 causes the distal end of clip housing 16 to abut against the exterior of the vessel, so that back bleed indicator ports 42 of clip housing 16 directly communicate with the puncture wound. The presence of pressure in the vessel higher than atmospheric pressure causes blood to pass through indicator ports 42, blood lumens 44, and exit through the proximal ends of tubes 25, thus confirming that clip housing 16 is positioned at the puncture site and should not be advanced further.

Figure 5C:
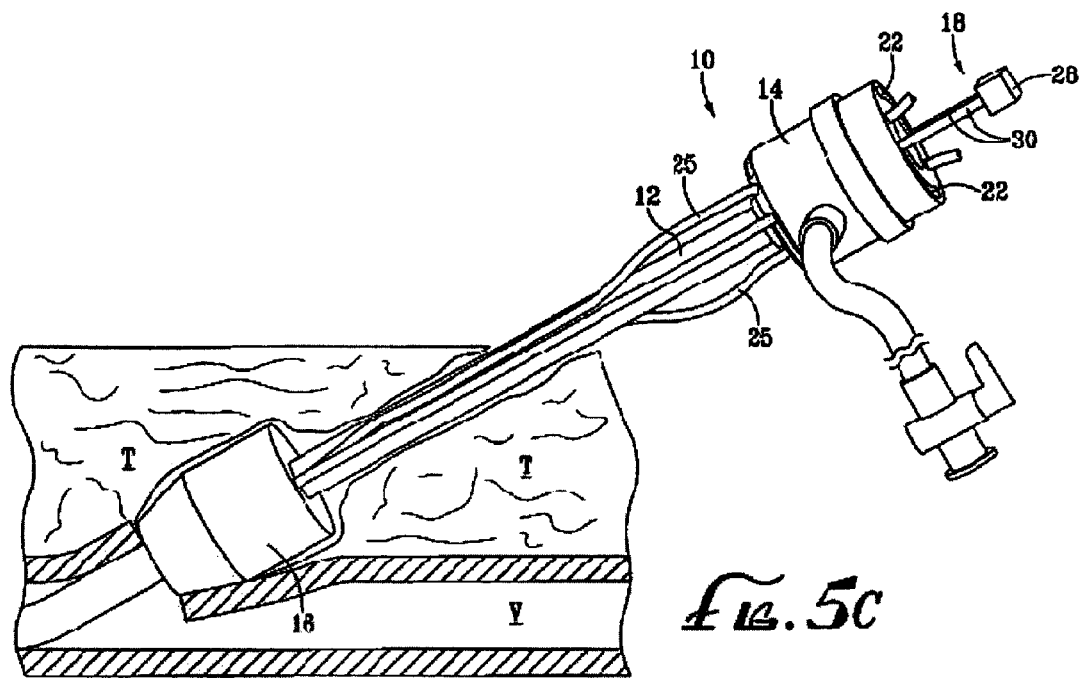

In FIG. 5C, with clip housing 16 held immobile, clip actuator 18 is rotated clockwise within arc-shaped lumens 22 so that rods 30 rotate and advance clip housing 16 with respect to clip expander 58 (see FIG. 2). Specifically, ledge 54 of housing 16 contacts the proximal end of clip 62 and drives the clip distally so that its tissue-engaging members, spikes 76 and 78, contact and pierce the wall of vessel V at points around the puncture site, as discussed hereinabove with respect to FIG. 2.

Figure 5D:
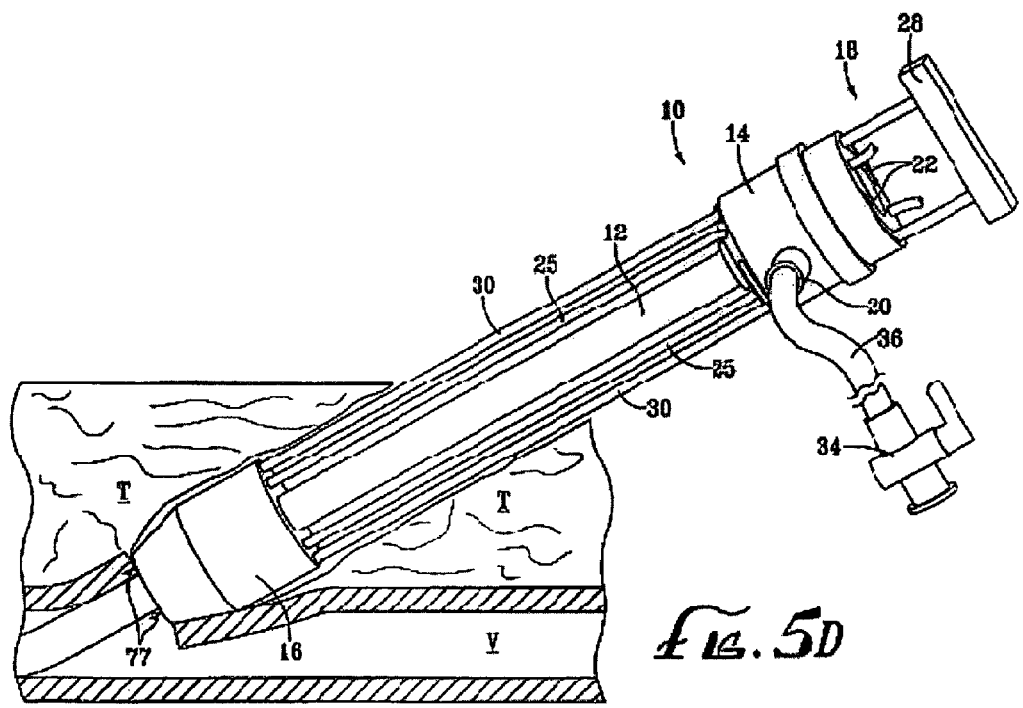

Once the spikes have pierced the vessel wall, clip actuator 18 is rotated counterclockwise within arc-shaped lumens 22 to retract clip housing 16, via threaded bore 46, along clip expander 58. The tissue-engaging members of clip 62 retain the clip within the wall of vessel V while the housing retracts, as shown in FIG. 5D.

Figure 5E:
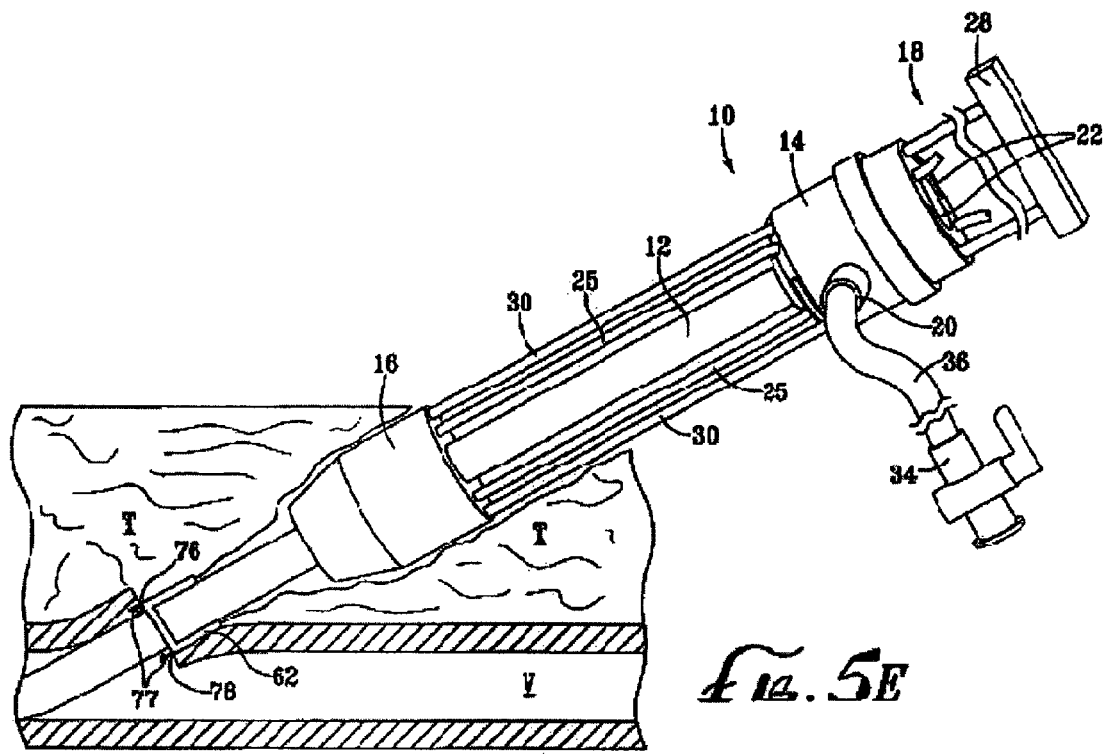

In FIG. 5E, with clip 62 engaged with the vessel wall, clip housing 16 and clip expander 58 are withdrawn proximally by proximally withdrawing actuator 18, thereby causing clip 62 to slide off of clip expander 58. In FIG. 5E, spike 78 is embedded in tissue not shown, because that tissue lies within the plane of the cross section.

Figure 5F:
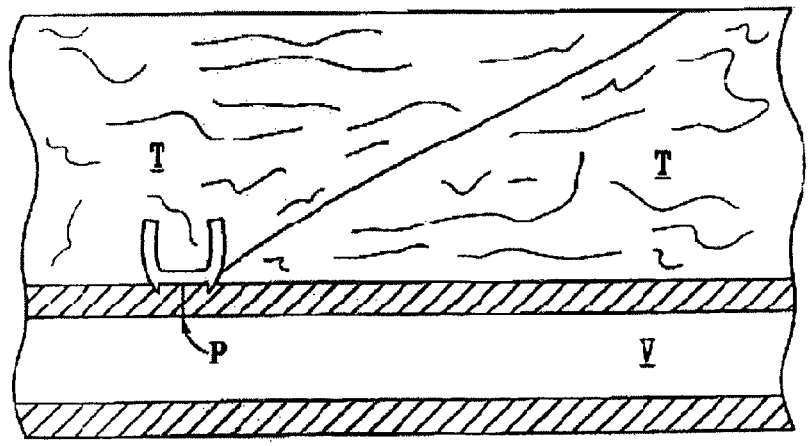

Vascular device 10 then is withdrawn from the vessel wall. Once introducer sheath 12 is removed from lumen 80 of clip 62, the clip rotates relative to the vessel wall, as shown in FIG. 5F, and returns to its unstressed, deployed configuration, thus drawing opposite sides of puncture P together to seal the puncture. At this point, a suitable biocompatible bioglue or tissue sealant optionally may be injected into the puncture tract, as discussed hereinabove, through device port 26 or side port, to aid in sealing vascular puncture P. Alternatively, the bioglue or tissue sealant may be delivered through the back bleed path described above.

Although preferred illustrative embodiments of the present invention are described above, it will be evident to one skilled in the art that various changes and modifications may be made without departing from the invention. For example, with minor modifications, vascular device 10 may be configured to carry spring clip 90 of FIG. 4, or any of a variety of alternative expandable resilient clips. It is intended in the appended claims to cover all such changes and modifications that fall within the true spirit and scope of the invention. Accordingly, additional embodiments are described below.

III. Second Closure System Embodiment

Figure 6:
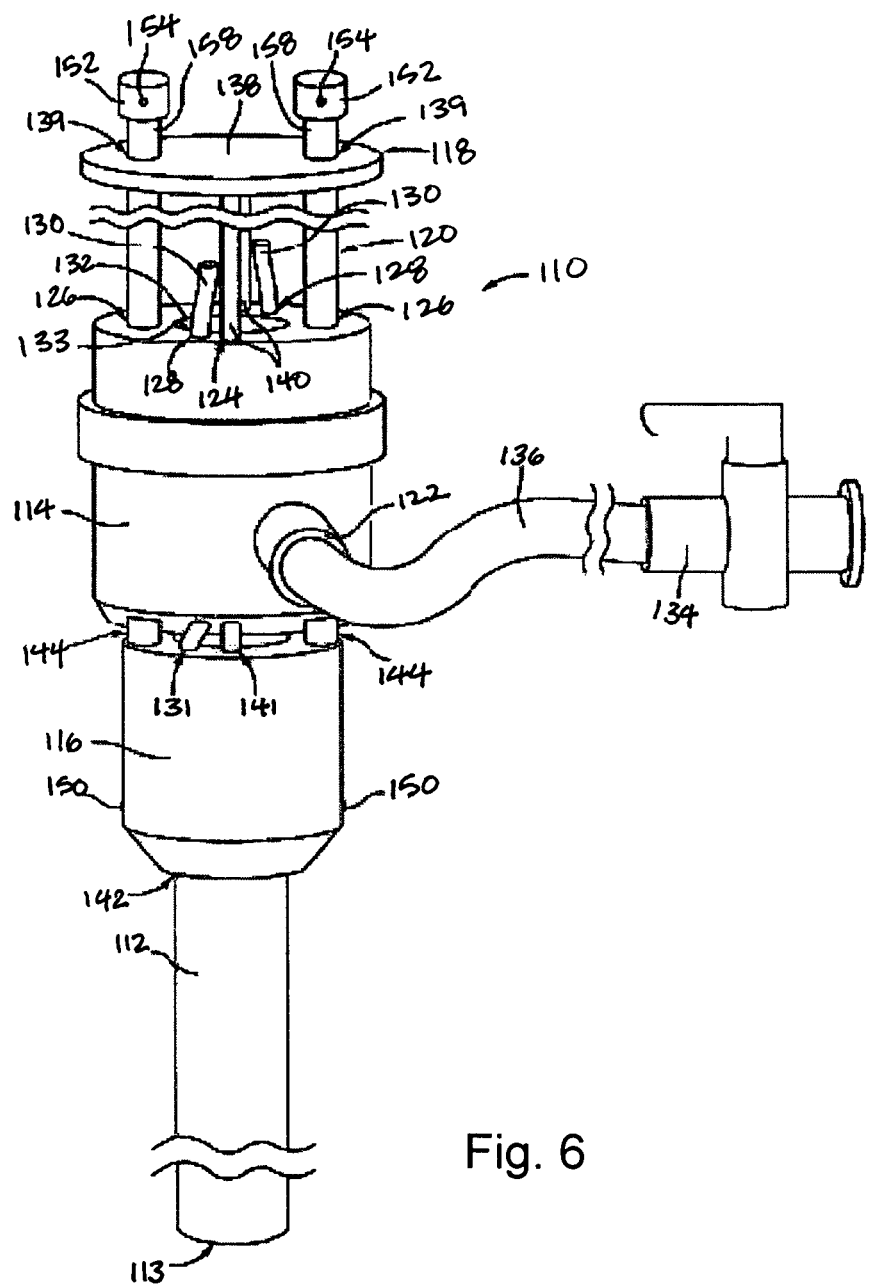
FIG. 6 is a side view of an integrated vascular device constructed in accordance with the present invention.

Referring to FIG. 6, a first embodiment of apparatus of a second operating environment the present invention is described. Vascular device 110 comprises introducer sheath 112 coupled to hub 114, clip housing 116 and clip actuator 118. A closure component 120, as described in detail hereinbelow, is disposed in clip housing 116.

Introducer sheath 112 comprises a material typically used for vascular introducer sheaths, such as polyethylene or nylon, and includes central lumen 113 through which other interventional devices may be introduced into the vasculature, for example, to perform a diagnostic or interventional procedure such as angiography, angioplasty, or stenting.

Hub 114 is mounted to the proximal end of introducer sheath 112 and includes side port 122, actuator lumens 124, closure lumens 126, back bleed lumens 128, back bleed tubes 130, and device port 132. Device port 132 communicates with central lumen 113 of introducer sheath 112, and has self-sealing elastomeric membrane 133 disposed across it. Self-sealing membrane 133, which may comprise, e.g., latex or a biocompatible synthetic rubber, permits interventional devices to be introduced through device port 132, while preventing blood loss through central lumen 113. Side port 122 of hub 114 is also in communication with central lumen 113, and is connected to hemostatic port 134 via biocompatible tubing 136.

Clip housing 116 includes two lumens, as described hereinbelow, that each hold a bioabsorbable, deformable clip. In accordance with the principles of the present invention, clip housing 116 is slidably disposed on the exterior of introducer sheath 112 and is movable from a stowed position, adjacent hub 114, to a distal clip deployment position, where the bioabsorbable clip is urged into engagement with tissue surrounding a vascular puncture. Clip housing 116 prevents the clips from snagging on tissue during advancement of clip housing 116.

Clip actuator 118 comprises plunger 138 and rods 140, which are configured to slidably pass through actuator lumens 124 of hub 114. Plunger 138 further includes openings 139. The distal ends of rods 140 are mounted in clip housing 116, so that movement of plunger 138 causes corresponding proximal or distal movement of clip housing 116. As described in detail hereinafter, when plunger 138 is moved to its proximal-most position, clip housing 116 is disposed adjacent to hub 114 and provides adequate clearance for interventional devices to be inserted through device port 132 and central lumen 113 into the patient's vasculature. When moved to its distal-most position, plunger 138 causes rods 140 to urge clip housing 116 distally.

Referring now to FIGS. 6 and 7A-7C, closure component 120 of vascular device 110 is described in greater detail. Clip housing 116 comprises lumen 142 that slidably receives introducer sheath 112, rod bores (not shown) in which rods 140 are mounted, clip lumens 144 in which bioabsorbable clips 146 are housed and advanced to a puncture site, pin holes 148 for rigidly receiving distal pins 150, and back bleed indicator ports (not shown, out of the plane of the cross-section of FIG. 7A) that are coupled to back bleed tubes 130 via blood lumens 131.

Closure component 120 further comprises caps 152 with pin holes (not shown, out of the plane of the cross-section of FIG. 7A) configured to receive proximal pins 154, clip holders 156 attached to bioabsorbable clips 146, and locking collar drivers 158 configured to advance fasteners 160. Locking collar drivers 158 are slidably received within lumens 139 of plunger 138, closure lumens 126 of hub 114, and clip lumens 144 of clip housing 116. Drivers 158 further comprise lumens 159 and square clip bores 147, in which clip holders 156 and clips 146, respectively, are slidably received. Bores 147 are of square cross section.

As illustrated in FIG. 7B, locking collar drivers 158 comprise proximal driver slots 162 that communicate with lumens 159, while clip holders 156 comprise proximal holder slots 164. Proximal pins 154, mounted in caps 152, pass through and are slidably received within slots 162 and 164. As seen in FIG. 7C, locking collar drivers 158 further comprise distal driver slots 166 that communicate with lumens 159, while clip holders 156 further comprise distal holder slots 168. Distal pins 150, mounted in clip housing 116, pass through and are slidably received within slots 166 and 168.

As discussed hereinabove, back bleed indicator ports (not shown) are coupled to back bleed tubes 130 via blood lumens 131 that extend through clip housing 1116. Back bleed tubes 130 are slidably disposed through back bleed lumens 128 of hub 114. When the distal end of clip housing 116 is advanced distally against a vessel wall at a vascular puncture, blood enters the back bleed indicator ports and exits through tubes 130, providing visual confirmation to an operator that the distal end of clip housing 116 is positioned adjacent to the vessel wall. Back bleed tubes 130 thus enable the operator to determine when clip housing 116 has been sufficiently advanced to permit clip deployment, while reducing the risk that the clip is either deployed short of the puncture site or extended into the vessel.

In conjunction with clip deployment, a bioglue or tissue sealant may be delivered through hemostatic port 134, biocompatible tubing 136, side port 122 and central lumen 113 of introducer sheath 112 to the vascular puncture to further help seal the vessel after deployment of clips 146. Alternatively, the bioglue or tissue sealant may be delivered through device port 132 or through the back bleed path described above.

Figure 8A:
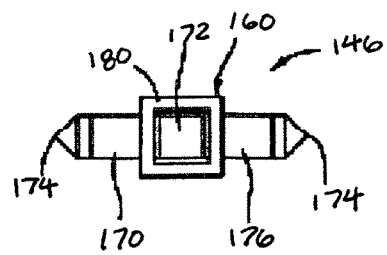
FIGS. 8A-8C are, respectively, views of a bioabsorbable clip and fastener of the present invention shown in top view in a delivery configuration, in side view in the delivery configuration, and in side view in a deployed configuration.
Figure 8B:
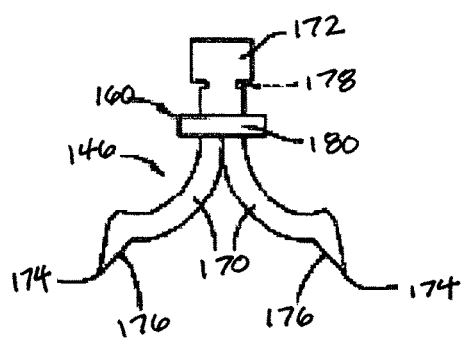
Figure 8C:
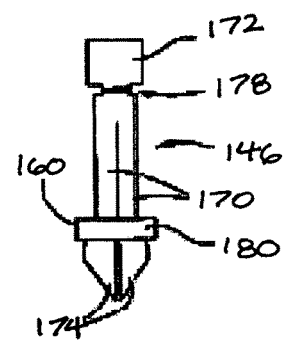

With reference now to FIGS. 8A-8C, bioabsorbable clip 146 and fastener 160 are described in greater detail. FIG. 8A shows clip 146 in the delivery configuration. Clip 146 comprises curved legs 170 and proximal end 172. Legs 170 distally terminate at spikes 174 with optional engagement means 176, and proximally terminate at narrowed region 178. Engagement means 176 may comprise, for example, barbs or hooks. As seen in FIG. 7A, proximal end 172 attaches to clip holder 156 by, for example, adhesive, and is slidably received by square clip bore 147 of locking collar driver 158. As with bore 147, clip 146 is of substantially square cross section.

Fastener 160 comprises bioabsorbable locking collar 180, which is slidably received on the exterior of clip 146. As seen in FIG. 8B, locking collar 180 may be distally advanced down the exterior of clip 146 to deform the clip to its deployed configuration, wherein curved legs 170 and spikes 174 are drawn together. Clip 146 may then be separated from clip holder 156 by rotating-proximal end 172 with respect to legs 170, causing the clip to snap into two pieces at narrowed region 178, for the reasons described hereinafter. Clip 146 and locking collar 180 preferably are fabricated from bioabsorbable materials, such as polyglycolic acid.

Figure 9A:
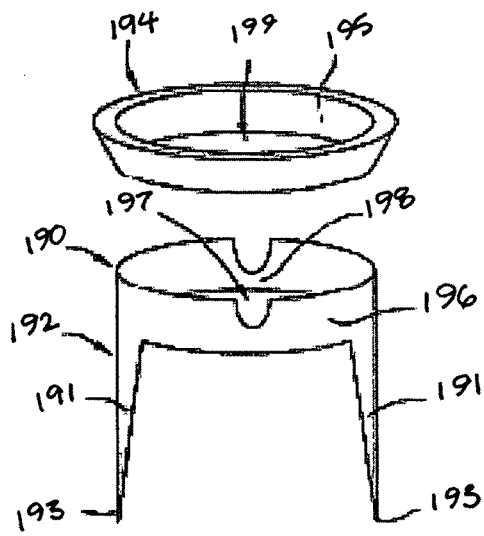
FIGS. 9A and 9B are isometric views of an alternative embodiment of the bioabsorbable surgical clip and fastener, constructed in accordance with the present invention and shown, respectively, in a delivery configuration and in a deployed configuration.
Figure 9B:
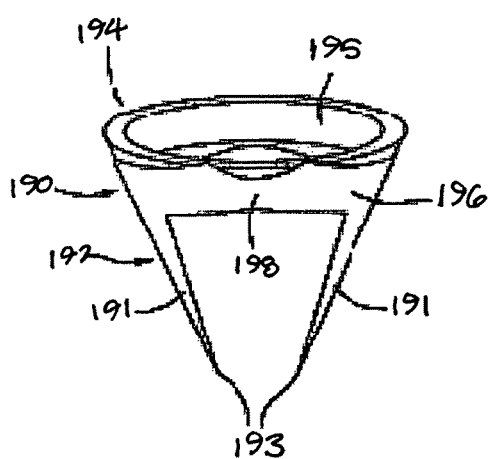

Referring to FIGS. 9A-9B, an alternative embodiment of the closure component of the present invention is described. Closure component 190 comprises bioabsorbable clip 192 and fastener 194. Clip 192 comprises proximal hoop 196 with narrowed regions 198, and legs 191 terminating in spikes 193. Fastener 194 comprises bioabsorbable wedge 195. Wedge 195 has a diameter substantially equal to the diameter of hoop 196 at its distal end, the diameter tapering to a maximum diameter at the proximal end of wedge 195. Clip 192 therefore may be deformed from the delivery configuration of FIG. 9A to the deployed configuration of FIG. 9B, wherein legs 191 and spikes 193 are drawn together, by advancing wedge 195 into hoop 196 to deform clip 192 at narrowed regions 198. Lumen 197 extends through hoop 198 of clip 192, while lumen 199 extends through wedge 196. Clip 192 and wedge 196 therefore are configured for delivery over the exterior of an introducer sheath. The clip and wedge preferably are fabricated from bioabsorbable materials.

With reference to FIGS. 10A-10B through 13A-13B, methods of using vascular device 110 are described in connection with FIGS. 6-9B. Introducer sheath 112 is advanced through skin, fat, and muscle tissue into vessel V, through vascular puncture P, which is formed in accordance with well-known techniques. Vascular device 110 is used in the same manner as a standard introducer sheath, with instruments being advanced into the vessel via lumen 113. Specifically, with plunger 128 and rods 140 in the proximal-most, fully retracted position, an interventional procedure then is performed by introducing one or more interventional devices, e.g. angioplasty balloons, stent delivery systems, atherectomy devices, etc., through device port 132 and lumen 113 of introducer sheath 112 in accordance with well-known techniques. Side port 122 may be used to infuse fluids, e.g., contrast agents or medications, into the vessel through introducer sheath 112 during the interventional procedure.

Upon completion of the procedure, vascular device 110 advantageously may be used to close vascular puncture P. At this point, clip actuator 118, clip housing 116, and closure component 120 with clips 146, are disposed in the proximal-most position adjacent to hub 114.

Clip actuator 118 then is advanced by urging plunger 138 in the distal direction, thus causing rods 140 to slide through actuator lumens 124 of hub 114 and advance clip housing 116. Distal pins 150, mounted in housing 116, abut distal slots 166 and 168 of drivers 158 and holders 156, respectively. Thus, distal advancement of clip housing 116 also distally advances closure component 120. Continued distal advancement of plunger 138 causes the distal end of clip housing 116 to abut against the exterior of the vessel, so that the back bleed indicator ports (not shown) of clip housing 116 directly communicate with the puncture wound. The presence of pressure in the vessel higher than atmospheric pressure causes blood to pass through the indicator ports, through blood lumens 131, and exit through the proximal ends of tubes 130, thus confirming that clip housing 116 is positioned at the puncture site and should not be advanced further.

FIG. 10B illustrates closure component 120 via sectional views through clip housing 116 along planes parallel to introducer sheath 112. FIG. 10A shows the locations of proximal pins 154 within proximal slots 162 and 164, and the locations of distal pins 150 within distal slots 166 and 168, corresponding to the relative longitudinal positions of clip holders 156 and locking collar drivers 158 depicted in FIG. 10B. Pin locations are shown via side views of clip holders 156 and locking collar drivers 158 at the relevant locations.

As seen in FIGS. 10A and 10B, with clip housing 116 positioned at puncture site P, proximal pins 154, mounted in caps 152, are positioned at the extreme right of proximal driver slots 162 and of the circumferential portions of proximal holder slots 164. Distal pins 150 are located at the distal end of distal driver slots 166 and of the longitudinal portions of distal holder slots 168.

In FIGS. 11A and 11B, with clip housing 116 held immobile, force is applied to caps 152 to distally advance clips 146 with respect to housing 116. Specifically, proximal pins 154 abut and apply force against proximal slots 162 and 164, which advances drivers 158 and clip holders 156, as well as attached clips 146 and locking collars 180. Distal pins 150 move freely within distal slots 166 and the longitudinal portions of distal slots 168. Distal advancement of clips 146 continues until pins 150 abut against the proximal end of the longitudinal portions of distal holder slots 168 of clip holders 156. Drivers 158 likewise are restrained by their connection to clip holders 156 via proximal pins 154. The tissue-engaging members, spikes 174 and engagement means 176, of clips 146 contact and pierce the wall of vessel V on opposite sides of the puncture site P.

As seen in FIGS. 12A and 12B, once the spikes have pierced the vessel wall, locking collar drivers 158 are advanced distally while clip housing 116 and clip holders 156 remain stationary, thereby distally advancing locking collars 180 down the exteriors of clips 146 to draw legs 170 and spikes 174 together to close puncture P. Engagement means 176 serve to retain the clips within the vessel wall during healing.

To achieve this advancement of drivers 158 with respect to clip holders 156, caps 152 are rotated clockwise, as viewed from above, until proximal pins 154 abut against the extreme left of proximal slots 162 and 164, thereby aligning the pins with the longitudinal portions of proximal holder slots 164. Then, force is once again applied to caps 152 to advance drivers 158 and deform clips 146 to their deployed configurations. Specifically, proximal pins 154 abut and apply force to proximal driver slots 162, thereby distally advancing drivers 158. Pins 154 move freely within the longitudinal portions of proximal holder slots 164 until they abut against the distal ends of slots 164. Likewise, distal driver slots 166 move freely until distal pins 150 abut the proximal ends of slots 166. In FIG. 12A, when proximal pins 154 abut slots 164 and distal pins 150 abut slots 166, locking collars 180 have been driven down the exteriors of clips 146, thereby deforming the clips to draw legs 170 together and close the puncture site.

In FIGS. 13A and 13B, with clips 146 deformed to seal puncture P, clip holders 156 are detached from clips 146 by snapping the clips free at narrowed regions 178. At this point, or prior to detachment, a suitable biocompatible bioglue or tissue sealant optionally may be injected into the puncture tract, as discussed hereinabove, through device port 132 or side port 122, to aid in sealing vascular puncture P. Alternatively, the bioglue or tissue sealant may be delivered through the back bleed path described above. Vascular device 110 then is withdrawn from the vessel wall, completing the procedure.

Clips 146 are detached from clip holders 156 by rotating caps 152 counterclockwise, as viewed from above. Proximal pins 154 of caps 152 move freely within proximal driver slots 162, but abut against the distal end of the longitudinal portions of proximal holder slots 164 and cause clip holders 156 to rotate with respect to collar drivers 158. Distal pins 150 of clip housing 116 move freely within the circumferential portions of distal holder slots 168 during rotation of clip holders 156. Meanwhile, drivers 158 are restrained from rotation by distal pins 150, which abut against distal driver slots 166. Bioabsorbable clips 146 do not rotate because the square cross section of square clip bores 147 of drivers 158 matches the substantially square cross section of clips 146; thus, since drivers 158 are restrained from rotation, so are clips 146. Non-square cross sections for clips 146 and bores 147, capable of performing the restraining function, will be apparent to those of skill in the art and fall within the scope of the present invention.

Since clips 146 are restrained while clip holders 156 rotate, and since proximal ends 172 of clips 146 are attached to clip holders 156, counterclockwise rotation of caps 152 causes clips 146 to snap at their weakest points: narrowed regions 178. Vascular device 110 may then be removed from the patient to complete the procedure.

Although preferred illustrative embodiments of the present invention are described above, it will be evident to one skilled in the art that various changes and modifications may be made without departing from the invention. For example, with minor modifications, vascular device 110 may be configured to carry closure component 190 of FIG. 10A, or any of a variety of alternative bioabsorbable and deformable clips. Proximal pins 154 may be formed integrally with caps 152, and distal pins 150 may be formed integrally with clip housing 116. Any number of clips 146 may be used to close the vascular puncture. It is intended in the appended claims to cover all such changes and modifications that fall within the true spirit and scope of the invention.

IV. Third Closure System Embodiment

Figure 14:
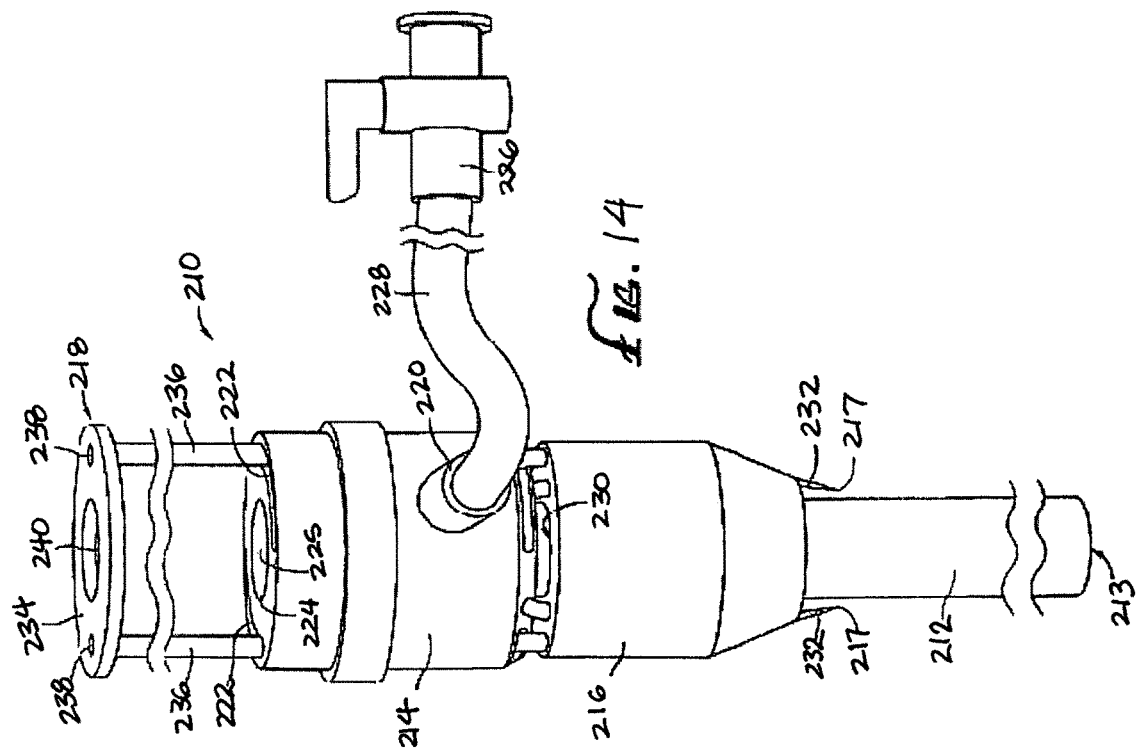
FIG. 14 is a side view of a preferred embodiment of an integrated vascular device constructed in accordance with the present invention.

Referring to FIG. 14, a first embodiment of an apparatus of the third operating environment in accordance with present invention is described. Vascular device 210 comprises sheath 212 coupled to hub 214, closure component 216, and closure actuator 218.

Sheath 212, which may, for example, comprise an introducer sheath, a trocar, or a catheter, includes central lumen 213 through which other devices may be introduced into the vasculature, for example, to perform a diagnostic or interventional procedure such as angiography, angioplasty, or stenting, or to seal a puncture site.

Hub 214 is mounted on the proximal end of sheath 212 and includes side port 220, arc lumens 222, and device port 224. Device port 224 communicates with central lumen 213 of sheath 212, and has self-sealing elastomeric membrane 225 disposed across it. Self-sealing membrane 225, which may comprise, for example, latex or a biocompatible synthetic rubber, permits interventional devices to be introduced through device port 224, while preventing blood loss through central lumen 213. Side port 220 of hub 214 is also in communication with central lumen 213, and is connected to hemostatic port 226 via biocompatible tubing 228.

In accordance with the principles of the present invention, closure component 216 comprises lumen 230 that receives sheath 212. Component 216 is slidably disposed on the exterior of sheath 212 and is movable from a stowed position, adjacent hub 214, to a distal deployment position, where tines 217 of component 216 are urged into engagement with tissue surrounding a vascular puncture. Closure component 216 comprises at least two sharpened tips, or tines 217. Tines 217 preferably comprise back bleed ports 232. Closure component 216 is rotatable within arc-lumens 222 about the longitudinal axis of sheath 212, so that, with tines 217 engaging tissue surrounding the vascular puncture, component 216 closes the puncture.

Closure actuator 218 comprises plunger 234 and tubes 236, which are configured to slidably pass through arc lumens 222 of hub 214. The proximal ends of tubes 236 are coupled to back bleed bores 238 of plunger 234. The distal ends of tubes 236 are mounted, either permanently or detachably, in closure component 216, so that movement of plunger 234 causes corresponding proximal or distal movement of closure component 216. Likewise, rotation of plunger 234 causes corresponding rotation of tubes 236 within arc lumens 222, which, in turn, rotates closure component 216 about the longitudinal axis of sheath 212.

Plunger 234 further comprises device bore 240, coaxially aligned with device port 224, and through which interventional devices or puncture sealants may be passed. As described in detail hereinafter, when plunger 234 is moved to its proximal-most position, closure component 216 is disposed adjacent to hub 214 and preferably provides adequate clearance for interventional devices to be inserted through device port 224 and central lumen 213 into the patient's vasculature. When moved to its distal-most position, plunger 234 causes tubes 236 to urge closure component 216 distally. Interventional devices or sealants then may be introduced through device bore 240, device port 224, and central lumen 213 into the vasculature.

Back bleed bores 238 of plunger 232 are in communication with back bleed lumens (not shown) within tubes 236. The back bleed lumens of tubes 236 are in communication with back bleed ports 232 of tines 217, thereby establishing a complete back bleed path through ports 232, the lumens (not shown) of tubes 236, and bores 238. When tines 217 of closure component 216 pierce a vessel wall surrounding a vascular puncture, blood enters back bleed ports 232 and exits through back bleed bores 238, providing visual confirmation to a surgeon that tines 217 are positioned within the vessel wall. The back bleed path thus enables the surgeon to determine when closure component 216 has been sufficiently advanced to permit rotation of component 216 to close the puncture, while reducing the risk that component 216 is either short of the puncture site or is extended into the vessel.

In conjunction with closure of the puncture site caused by rotation of component 216, a puncture sealant may be introduced to the puncture site to seal the site closed. The sealant may, for example, comprise an adhesive, such as a bioglue, tissue sealant, or clotting agent, delivered through hemostatic port 226, biocompatible tubing 228, side port 220 and central lumen 213 of introducer sheath 212 to the vascular puncture to further help seal the vessel after puncture closure with closure component 216. Alternatively, the adhesive may be delivered through device port 224 or through the back bleed path described above. Instead of adhesives, the closure component may further comprise the sealant, wherein the closure component is left in place within the vessel until hemostasis naturally occurs. The sealant may also comprise sutures delivered through central lumen 213. Additionally, the sealant may comprise thermal energy application from, for example, electrical induction, infrared light, ultrasonic vibration, microwave or laser irradiation, and other means.

Figure 15:
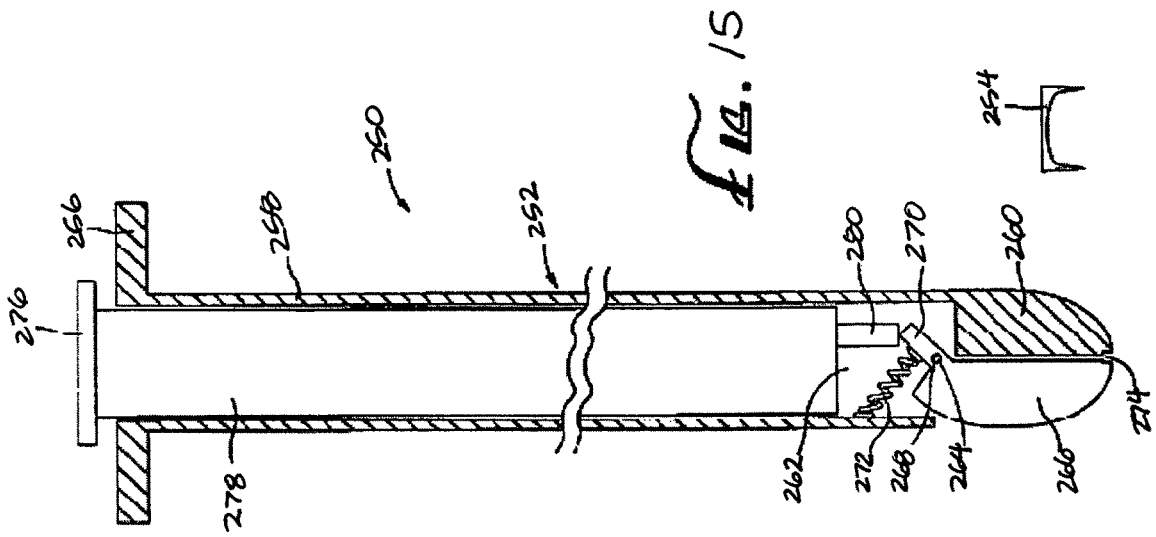
FIG. 15 is a side-sectional view of a sealing device for use with the vascular device of FIG. 14.

With reference to FIG. 15, an alternative puncture sealing device in accordance with the present invention is described. Sealing device 250 comprises delivery device 252 and clip 254. Delivery device 252 comprises proximal end 256 attached to tube 258. Tube 258 terminates at first jaw 260 at its distal end and further comprises lumen 262 and pin 264. Pin 264 extends into lumen 262 from an interior surface of tube 258 and is disposed perpendicular to the longitudinal axis of tube 258.

Delivery device 252 further comprises second jaw 266 having female connector 268 coupled to pin 264, so that second jaw 266 pivots about pin 264. Second jaw 266 further comprises moment arm 270. Tension spring 272 is coupled to moment arm 270 and to the interior surface of tube 258 in a manner that biases second jaw 266 against first jaw 260.

First jaw 260 and second jaw 266 preferably form channel 274 when biased against one another. Channel 274 is configured to receive clip 254. The biasing force applied by tension spring 272 holds clip 254 within channel 274, so that the clip may be advanced into tissue surrounding a vascular puncture that has had its edges approximated by closure component 216.

Delivery device 252 still further comprises plunger 276 coupled to pushrod 278 having release arm 280. Pushrod 278 is received within lumen 262 of tube 258, so that release arm 280 engages moment arm 270.

Distal advancement of pushrod 278, via application of force to plunger 276, causes release arm 280 to urge moment arm 270 distally. This motion overcomes the biasing force applied by tension spring 272 and causes second jaw 266 to pivot about pin 264. Second jaw 266 thus no longer contacts first jaw 260, and clip 254 is released from channel 274. Tube 258, first jaw 260, second jaw 266, and clip 254 of sealing device 250 preferably are sized for introduction into a patient's vasculature through device bore 240, device port 224, and lumen 213 of vascular device 210.

Referring to FIGS. 16A-16B through 19A-19B in conjunction with FIGS. 14 and 15, a method of using vascular device 210 with sealing device 250 is described. Sheath 212 is advanced through skin, fat, and muscle tissue into vessel V, through the vessel wall tissue surrounding vascular puncture P. With plunger 234 and tubes 236 of actuator 218 in the proximal-most, fully retracted position, an interventional procedure is performed by introducing one or more interventional devices, e.g. angioplasty balloons, stent delivery systems, atherectomy devices, etc., through device port 224 and lumen 213 of sheath 212, in accordance with well-known techniques. Side port 220 may be used to infuse fluids, e.g., contrast agents or medications, into the vessel through sheath 212 during the interventional procedure.

Upon completion of the procedure, vascular device 210 may be advantageously used to close vascular puncture P. At this point, closure actuator 218 and closure component 216 are disposed in the proximal-most position, with component 216 adjacent to hub 214. Closure actuator 218 is advanced by urging plunger 234 in the distal direction, thus causing tubes 236 to slide through arc lumens 222 of hub 214 and advance closure component 216.

As seen in FIG. 16A, continued distal advancement of plunger 234 causes tines 217 at the distal end of closure component 216 to pierce tissue surrounding puncture P, so that the back bleed ports 232 of tines 217 directly communicate with the puncture wound. Tine punctures T in FIG. 16B represent the points at which tines 217 enter vessel V. The presence of pressure in the vessel higher than atmospheric pressure causes blood to pass through back bleed ports 232, through the back bleed lumens (not shown) of tubes 236, and exit through the proximal ends of back bleed bores 238, thus confirming that tines 217 have engaged tissue around the puncture site and should not be advanced further.

In FIG. 17A, sheath 212 is removed from puncture P to facilitate closure of LuHP the puncture. Closure actuator 218 is held stationary while hub 214 is withdrawn proximally, thereby withdrawing sheath 212 proximally from puncture P. The puncture remains open, as seen in FIG. 17B. With sheath 212 no longer within puncture P, closure actuator 218 is rotated within arc lumens 222 to rotate closure component 216. Rotation of closure component 216 causes tines 217 to rotate and urge the puncture closed, as seen in FIGS. 18A and 18B.

Upon closure of puncture P, a sealant is introduced to seal the wound closed. The sealant may, for example, comprise an adhesive, such as a bioglue, tissue sealant, or clotting agent, it may comprise a suture, it may comprise thermal energy application, or it may comprise leaving the closure component in place within vessel V until hemostasis naturally occurs. Alternatively, the sealing device may comprise a clip, as described hereinafter.

FIGS. 18A and 19A show apparatus 210 used in conjunction with sealing device 250 of FIG. 15. With clip 254 disposed in channel 274 of delivery device 252, the delivery device is delivered to vessel V through device bore 240 of closure actuator 218, device port 224 of hub 214, and central lumen 213 of sheath 212. Clip 254 punctures the vessel at tissue surrounding closed puncture P, creating clip punctures C and sealing the puncture. Pushrod 278 of delivery device 252 is then actuated to separate second jaw 266 from first jaw 260 to release clip 254 from delivery device 252. Apparatus 210 and delivery device 252 are removed from the patient to complete the procedure. Clip 254 maintains closure until hemostasis occurs and is preferably bioabsorbable so that no foreign materials are permanently implanted in the patient's body. Additional clips may also be implanted, as required.

Figures 20A, 20B, 20C:
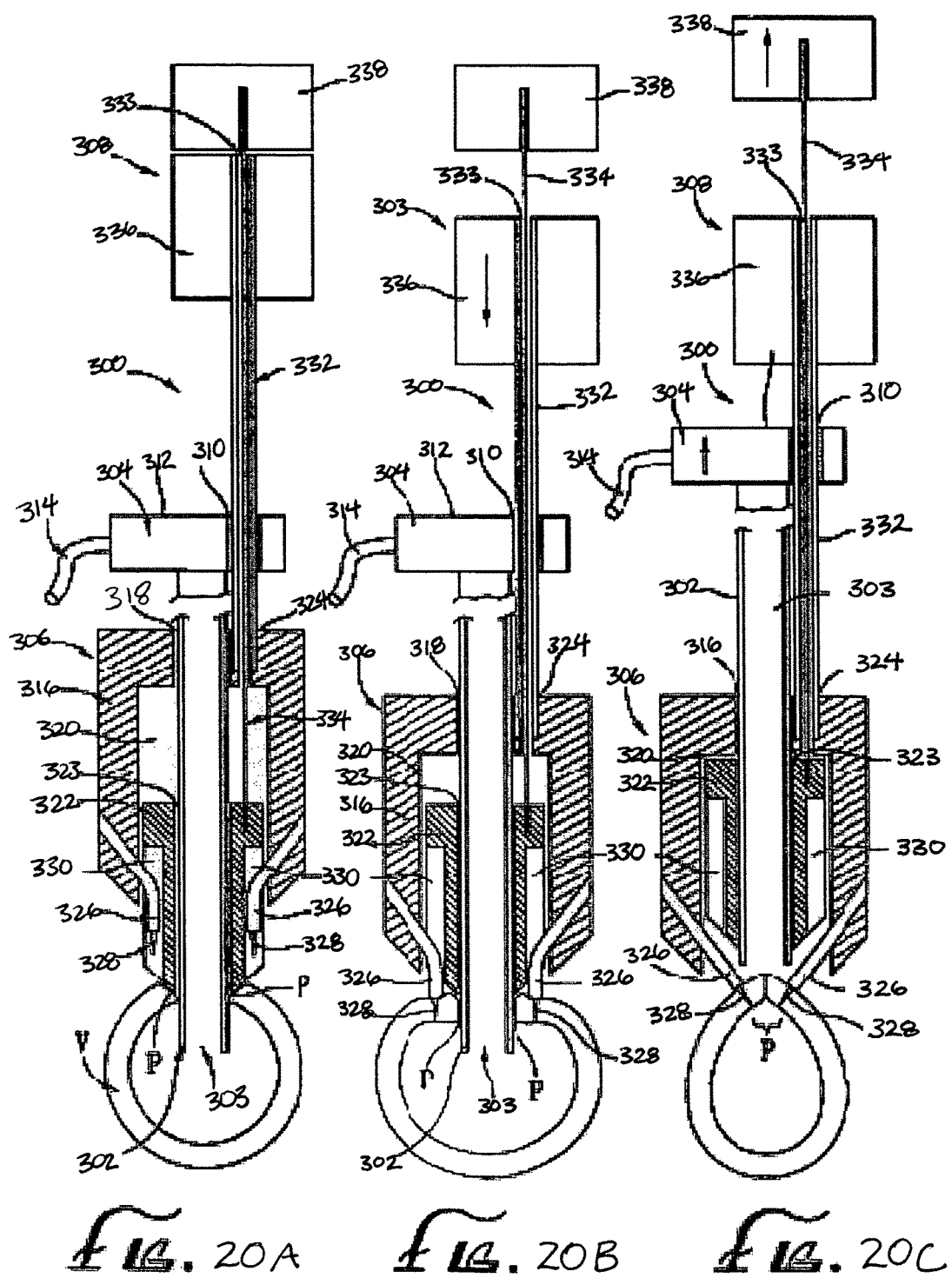
FIGS. 20A-20C are side-sectional views of an alternative embodiment of an integrated vascular device of the present invention in use at a vascular puncture site, illustrating a method of sealing the puncture site.

With reference now to FIGS. 20A-20C, an alternative integrated vascular device in accordance with the present invention is described. Apparatus 300 comprises sheath 302 coupled to hub 304, closure component 306, and closure actuator 308.

The sheath 302 may, for example, comprise an introducer sheath, a trocar, or a catheter, and includes central lumen 303 through which other devices may be introduced into the vasculature, for example, to perform a diagnostic or interventional procedure such as angiography, angioplasty, or stenting, or to seal a puncture site. Hub 304 comprises bore 310, which slidably receives actuator 308, and device port 312, which is in communication with central lumen 303 of sheath 302 and permits introduction of interventional devices while preventing blood loss through central lumen 303. Hub 304 further comprises side port 314.

Closure component 306 comprises outer housing 316 having lumen 318 configured to slidably receive sheath 302, bore 320 for slidably receiving inner housing 322, lumen 324 adapted to receive closure actuator 308, and needles or prongs 326 with sharpened tips 328. Inner housing 322 has lumen 323 adapted to receive sheath 302 and channels 330 adapted to receive prongs 326. Component 306 comprises at least two prongs 326, and preferably comprises four.

Closure actuator 308 comprises actuation tube 332 having lumen 333, actuation rod 334 disposed within actuation tube 332, first plunger 336 coupled to the proximal end of tube 332, and second plunger 338 coupled to the proximal end of rod 334. The distal end of tube 332 is affixed, either permanently or detachably, in lumen 324 to outer housing 316 of closure component 306, while the distal end of rod 334 is coupled to inner housing 322.

To perform an interventional procedure through central lumen 303 of sheath 302, the sheath is advanced through skin, fat, and muscle tissue into vessel V, through vascular puncture P, in accordance with well-known techniques. With closure component 306 in the proximal-most, fully retracted position adjacent hub 304, the interventional procedure then is performed by introducing one or more interventional devices, e.g. angioplasty balloons, stent delivery systems, atherectomy devices, etc., through device port 312 and lumen 303 of sheath 302, again in accordance with well-known techniques. Side port 314 may be used to infuse fluids, e.g., contrast agents or medications, into the vessel through sheath 302 during the interventional procedure.

Upon completion of the procedure, apparatus 300 advantageously may be used to close the vessel. Closure component 306 is advanced distally by urging plungers 336 and 338 distally. Inner housing 322 is only partially received within bore 320 of outer housing 316 so that prongs 326 are elastically deformed and received within channels 330. As shown in FIG. 20A, closure component 306 is advanced until inner housing 322 abuts against the vessel V, as may be determined, for example, with a back bleed indicator (not shown).

In FIG. 20B, first plunger 336 is urged distally to distally advance actuation tube 332 and outer housing 316, while second plunger 338 and sheath 302 are held stationary. Advancement of outer housing 316 advances sharpened tips 328 of prongs 126 into tissue surrounding puncture P.

In FIG. 20C, sheath 302 and second plunger 338 are retracted proximally to draw sheath 302 out of vessel V and to draw inner housing 322 completely within bore 320 of outer housing 316. Proximally retracting inner housing 322 via actuation rod 334 and second plunger 338 removes prongs 326 of outer housing 316 from channels 330 of the inner housing. The prongs resiliently contract to a lower stress configuration, thereby drawing opposing sides of puncture P together and closing the wound. A sealant may then be introduced to the closed puncture to seal the site closed, as discussed hereinabove. Alternatively, the sealing device may comprise RF current, supplied by an generator (not shown), applied across opposed tips 328, which act as bipolar electrodes.

Referring to FIGS. 21A-21E, as well as FIGS. 22A and 22B, a still further alternative embodiment of apparatus of the present invention is described. FIGS. 21A-21E depict the closure component of an integrated vascular device in use at vascular puncture P within vessel V. Apparatus 350 comprises sheath 352 coupled to a hub (not shown), closure component 354, and a closure actuator (not shown). Various closure actuators for use with closure component 354 will be apparent to those of skill in the art from the foregoing embodiments.

Sheath 352 may, for example, comprise an introducer sheath, a trocar, or a catheter, and includes central lumen 353 through which other devices may be introduced into the vasculature, for example, to perform a diagnostic or interventional procedure such as angiography, angioplasty, or stenting, or to seal a puncture site. Closure component 354 comprises spacer 356, needles 358, and needle cover 360. Spacer 356 is coaxially and slidably disposed about the exterior of sheath 352, and preferably has an annular diameter of about 1 mm to ensure that needles 358 engage the tissue surrounding puncture P rather than enter the puncture, so that the needles are able to draw the wound closed, as described hereinbelow. Needles 358 are disposed between spacer 356 and cover 360 during advancement to puncture P. Needles 358 comprise ledges 362, which act as positive stops to prevent excessive advancement of the needles with respect to cover 360, which comprises corresponding annular ledge 364. Cover 360 further comprises elastic segment 366, configured to elastically deform needles 358. Closure component 354 comprises at least two needles 358, and preferably comprises four. Needles 358 may further comprise retaining means (not shown), such as barbs or hooks, to assist in gripping tissue.

As shown in FIG. 21A, sheath 352 may be advanced through skin, fat, and muscle tissue into vessel V, through vascular puncture P, in accordance with well-known techniques. With closure component 354 in a proximal-most, fully retracted position adjacent the hub, an interventional procedure is performed through central lumen 353 of sheath 352 by introducing one or more interventional devices through the lumen into the patient's vasculature. Closure component 354 then is advanced via the closure actuator until it abuts against vessel V, as may be determined, for example, with a back bleed indicator, such as described for the foregoing embodiments. Cover 360 protects needles 358 and prevents snagging of tissue as closure component 354 is distally advanced down sheath 352 and through skin, fat, and muscle tissue. Spacer 356 retains needles 358 in a position away from the edge of puncture P.

In FIG. 21B, needles 358 are distally advanced with respect to needle cover 360 until ledge 362 abuts ledge 364. Needles 358 deflect elastic segment 366 of cover 360 outward and pierce tissue surrounding puncture P. FIG. 22A depicts, in isometric view, the segment of vessel V surrounding puncture P. With a needle arrangement comprising four needles 358, the needles create needle punctures N surrounding vascular puncture P. Sheath 352 and spacer 356 then are retracted proximally and removed from vessel V, as shown in FIG. 21C. As depicted in FIGS. 21C and 21D, elastic segment 366 of needle cover 360 resiliently contracts, thereby drawing needles 358 together and approximating the edges of the wound.

A sealant, such as a bioglue, tissue sealant, or clotting agent, then may be introduced to the puncture site to seal the wound closed. Alternatively, closure component 354 may be maintained in position until hemostasis occurs naturally, or sutures may be introduced through central lumen 353. In addition, or in the alternative, RF energy may be applied across needles 358 or a clip, such as clip 254 of sealing device 250 of FIG. 15, may be applied. Thermal energy from electrical induction, infrared light, ultrasonic vibration, microwave or laser irradiation, and other means may also be used to seal the puncture.

Illustratively, FIG. 21E depicts sealing device 370, comprising adhesive 372, being delivered through central lumen 353 within delivery sheath 374. After sufficient time for adhesive 372 to set, apparatus 350 is removed from vessel V.

V. Fourth Closure System Embodiment

Turning now to FIGS. 23-24, which show a first preferred embodiment of an apparatus 410 for providing access into a blood vessel or other body lumen from an incision, puncture, or other passage (not shown in FIGS. 23 and 24), and/or for delivering a closure element, such as clip 426 (shown in phantom), for closing the passage. Generally, the apparatus 410 includes an introducer sheath 412, a housing 424 slidably disposed on the sheath 412, a locator member 414 insertable into the sheath 412, and an housing actuator assembly 430.

The sheath 412 includes a substantially flexible or semi-rigid tubular body 415 including a lumen 416 extending between its proximal and distal ends 418, 420. The distal end 420 has a size and shape to facilitate insertion into a blood vessel, e.g., having a tapered tip 422 for facilitating substantially atraumatic introduction through the passage and at least partially into the vessel. The lumen 416 has a size for accommodating insertion of one or more devices therethrough, such as a catheter, guidewire, and the like (not shown). The sheath 412 also preferably includes a seal (not shown), such as a hemostatic valve, within the lumen 416 at or near the proximal end 418 that provides a fluid-tight seal, yet accommodates insertion of one or more devices, such as the locator 414, into the lumen 416 without fluid passing proximally from the sheath 412.

Optionally, the sheath 412 may include a side port 419 that communicates with the lumen 416, for example, to allow the infusion of fluids into the lumen 416, through the sheath 412. Alternatively, or in addition, the side port 419 may be used to provide a "bleed back" indicator, such as that disclosed in U.S. Pat. No. 6,626,918, entitled "Apparatus and Methods for Positioning a Vascular Sheath," which is assigned to the assignee of the present invention. The disclosure of this patent and any references cited therein are expressly incorporated herein.

A housing 424 is slidably disposed on an exterior of the sheath 412, the housing 424 configured for releasably holding the closure element 426. The housing 424 may include an ejector or other mechanism (not shown) for deploying the closure element 426 from the housing 424. In a preferred embodiment, the closure element 426 is an annular-shaped clip, including one or more barbs 428 for engaging the tissue around the puncture adjacent to the wall of the vessel. Preferably, the clip 426 is configured for drawing the tissue around the puncture at the wall of the vessel substantially closed and/or for enhancing hemostasis within the puncture. Exemplary embodiments of a housing and closure element for use with an apparatus in accordance with the present invention are disclosed U.S. Pat. Nos. 6,197,042, 6,461,364, and 6,391,048, which are expressly incorporated herein by reference.

The housing 424 is actuable from the proximal end 418 of the sheath 412 (FIG. 23), for example, by housing actuator assembly 430, for advancing the closure element 426 distally during deployment. The housing 424 may be substantially permanently but slidably disposed on the sheath 412. In this embodiment, the housing actuator assembly 430 may be substantially permanently attached to the proximal end 418 of the sheath 412. The housing 424 may be coupled to the housing actuator assembly 430 such that the housing 424 may be directed axially along the exterior of the sheath.

Alternatively, the housing 424 may be provided separate from the sheath 412 (not shown), e.g., with the closure element 426 preloaded therein. In this embodiment, the housing actuator assembly 430 may also be provided separate from the sheath 412, as shown, either coupled to or separate from the housing 424. Any time before delivering the closure element 426, the housing 424 may be directed over the sheath 412, e.g., by inserting the proximal end 418 of the sheath 412. The housing actuator assembly 430 may be attached to the proximal end 418 of the sheath 412, e.g., by cooperating connectors (not shown). The housing 424 may be coupled to the housing actuator assembly 430, if not already attached, thereby preparing the housing 424 for use.

In a preferred embodiment shown in FIGS. 23 and 24, the housing actuator assembly 430 includes first and second actuator members 446, 448 that are generally movable with respect to one another. The first actuator member 446 may be connected to the proximal end 418 of the sheath 412, for example, by rods (not shown) such that the first member 446 is substantially fixed with respect to the sheath 412. A rod, cable, or other control wire 444 is coupled to and extends generally proximally from the housing 424. The control wire 444 may extend along an outer surface of the sheath 412, as shown, or alternatively may extend through a lumen (not shown) in the sheath 412 beyond the proximal end 418.

A loose end 450 of the control wire 444 may be coupled to the second actuator member 448. For example, the housing actuator assembly 430 may be advanced over the control wire 444 such that the loose end 450 passes through aperture 452 in the first member 446 and is received in a mating pocket 454 in the second member 448, as best seen in FIG. 24. The loose end 450 may be frictionally engaged within the pocket 454 or, alternatively, the loose end 450 and pocket 454 may include cooperating detents (not shown) for securing the control wire 444 to the second actuator member 448.

The second actuator member 448 may be movable with respect to the first actuator member 446 by one or more rods or rails (not shown) extending therebetween. Thus, the second actuator member 448 may be movable from a first or proximal position (not shown), located a first distance from the first actuator member 446, distally to a second or distal position (shown in FIG. 24), located a second closer distance from the first actuator member 446. When the housing actuator assembly 430 is attached to the sheath 412 with the control wire 444 coupled to the second actuator member 448, the housing 424 may be directed from a proximal position (e.g., shown in FIG. 23) to a distal or delivery position (e.g., shown in FIG. 24) when the second actuator member 448 is moved from its proximal position to its distal position.

In a preferred embodiment, the second actuator member 448 is biased to its distal position, for example, by spring 456 or other biasing element. The second actuator member 448 may be locked in its proximal position, for example, by a locking mechanism (not shown), thereby retaining the housing 424 in its proximal position. When it is desired to advance the housing 424, a button, switch, or other activation member (not shown) may be deployed to release the locking mechanism, thereby automatically directing the second actuator member 448 towards the first actuator member 446, and thereby advancing the housing 424 to its distal position, as described further below. The closure element 426 may be automatically ejected from the housing 424 once it reaches the distal position or the closure element 426 may be subsequently ejected by a separate action. It will be appreciated by those skilled in the art that other housing actuator configurations may be provided for advancing the housing 424 with respect to the sheath 412, e.g., to deliver the closure element 426.

The housing actuator assembly 430 may also include an adjustment mechanism, such as threaded bolt or knob 458. For example, the knob 458 may be provided on the first actuator member 446 such that, as the knob 458 is rotated, the first actuator member 446 may be moved axially with respect to the sheath 412. Because the first actuator member 446 may be adjusted distally or proximally with respect to the sheath 412, the distal position of the second actuator member 448 consequently may be adjusted. This, in turn, may facilitate adjusting the distal position of the housing 424, e.g., to compensate for the thickness of a particular wall of a blood vessel when a closure element 426 is delivered to close a puncture in the wall.

Turning to FIGS. 23, 24, 25A, and 25B, the locator member 414 includes a flexible or semi-rigid tubular body or other elongate rail 432 having a proximal end 434 and a distal end 436. An actuator rod or other elongate member 438 is slidably disposed with respect to the rail 432, e.g., within a lumen 433 of tubular body 432. Preferably, the locator member 414 includes an annular ridge 440 or other detent on or near its proximal end 440 that may engage a complementary-shaped pocket 442 or other cooperating detent on the sheath 412. Thus, the locator member 414 may be substantially secured axially with respect to the sheath 412.

As best seen in FIGS. 25A and 25B, a distal portion 460 of the locator member 414 includes a substantially rounded, soft, and/or flexible distal tip 462, possibly including a pigtail (not shown) that may facilitate atraumatic advancement of the distal portion 460 into a blood vessel or other body lumen. The locator member 414 preferably has a length relative to the sheath 412 such that the distal portion 460 extends beyond the distal end 420 of the sheath 412 when the locator member 414 is fully received therein, as shown in FIG. 24.

One or more, and preferably a plurality of, positioning elements 464 are provided on the distal portion 460 that may be selectively expandable between a substantially axial collapsed configuration (shown in FIG. 25A) and a substantially transverse expanded configuration (shown in FIG. 25B). Preferably, the positioning elements 464 are substantially flexible splines configured for expanding substantially transversely with respect to a longitudinal axis 413 of the apparatus 410. In one embodiment, shown in FIGS. 23 and 24, the locator member 414 includes a pair of splines 464 disposed generally opposite one another about the distal portion 460. Alternatively, as shown in FIG. 28, the locator member 414 may include four splines 464 that are substantially equally spaced about the distal portion 460. The locator member 414 may include more or fewer splines without deviating from the scope of the present invention.

Optionally, the splines 464 may include radiopaque markers (not shown) or may be at least partially formed from radiopaque material to facilitate observation of the splines 464 using fluoroscopy or other imaging systems. In addition, the housing 424 may include a radiopaque marker, e.g., at its distal end (not shown) and/or the closure element 426 may include a radiopaque marker or may be made from radiopaque material. This may facilitate monitoring the relative location of the closure element 426 to the splines 464, as described further below.

Returning to FIGS. 25A and 25B, each spline 464 preferably has a first fixed (e.g., proximal) end 464a and a second movable (e.g., distal) end 464b. The second end 464b may be axially movable towards the first end 464a to cause an intermediate region 464c of the spline 464 to expand transversely outward, thereby defining the substantially transverse expanded configuration. In a preferred embodiment, actuator rod 438 extends through the distal portion 460 and is coupled to the second end 464b of the splines 464 and/or to distal tip 462 of the locator member 414. The rod 438 may be moved axially, e.g., proximally, with respect to the rail 432 to selectively expand the splines 464 between their collapsed configuration and their expanded configuration.

A locator actuator 470 may be coupled to the locator member 414, the locator actuator 470 configured for selectively expanding the splines 464 from their collapsed configuration to their expanded configuration. For example, the locator actuator 470 may include a switch 472 that may be depressed or rotated to retract or move the rod 438 proximally, thereby expanding or deploying the splines 464. The locator actuator 470 preferably includes a lock (not shown) for securing the rod 438 in a proximal position and thereby locking the splines 464 in their expanded configuration. The lock may be released, for example, by depressing the switch 472. The locator actuator 470 may include a spring 474 or other biasing mechanism for biasing the rod 438 distally, e.g., to return the splines 464 to their collapsed configuration when the lock is released. For example, as described further below, the lock may be released upon activation of the housing actuator assembly 430, e.g., when the second actuator member 448 moves towards its distal position.

Turning to FIGS. 26A-26F, the apparatus 410 may be used to provide access into a blood vessel or other body lumen 490. Preferably, the apparatus 410 may be used to deliver a closure device, such as clip 426, to close and/or seal an incision, puncture, or other passage 492 that extends from a patient's skin 494 through intervening tissue 496, and a wall 498 of the vessel 490.

Figure 26A:
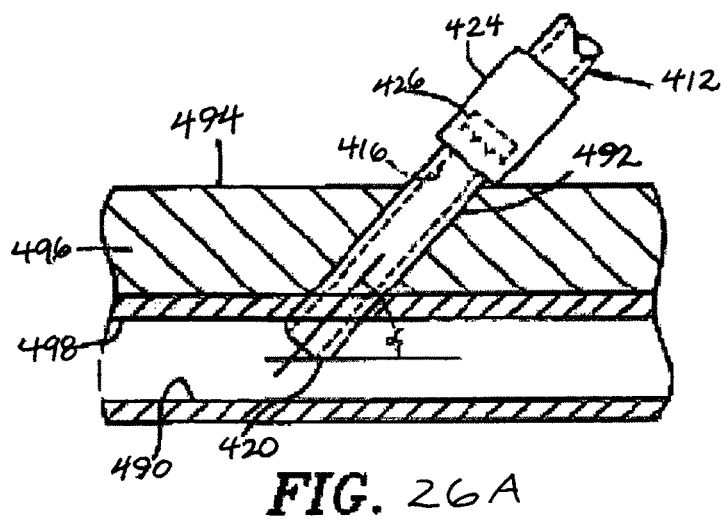
Figure 26B:
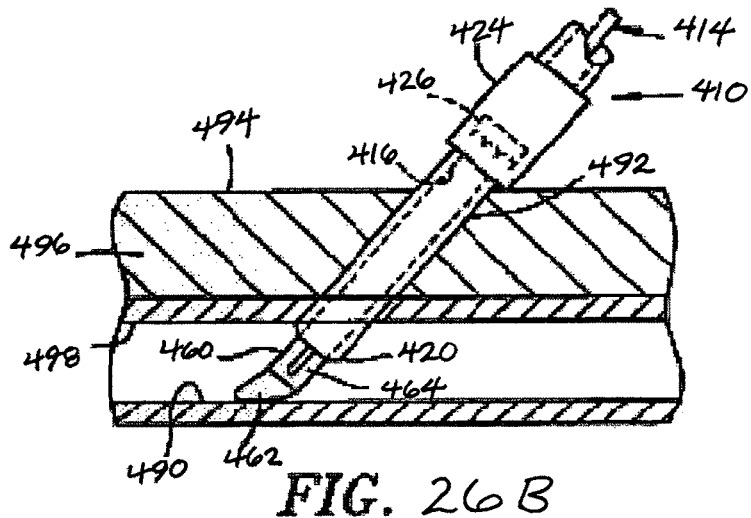

As shown in FIGS. 26A-26B, the sheath 412, without the locator member 414 therein, may be inserted or otherwise positioned within the blood vessel 490, i.e., through the passage 492. The sheath 412 is preferably provided with the housing 424 in its proximal position, without the housing actuator assembly (not shown) attached. Alternatively, the housing actuator assembly may be provided attached to the sheath 412 as long as the lumen 416 may be accessed. In a further alternative, the sheath 412 may be provided without the housing 424 thereon. The sheath 412 may be advanced over a guide wire or other rail (not shown) previously positioned through the passage 492 into the blood vessel 490 using a conventional procedure. Preferably, the blood vessel 490 is a peripheral vessel, such as a femoral or carotid artery, although other body lumens may be accessed using the sheath 412, as will be appreciated by those skilled in the art.

The passage 492, and consequently the sheath 412, may be oriented at a substantially acute angle alpha ("α") with respect to the vessel 490, thereby facilitating introduction of devices through the lumen 416 of the sheath 412 into the vessel 490 with minimal risk of damage to the vessel 490. One or more devices, such as a guide wire, a catheter, and the like (not shown), may be inserted through the sheath 412 and advanced to a desired location within the patient's body. For example, the devices may be used to perform a therapeutic or diagnostic procedure, such as angioplasty, atherectomy, stent implantation, and the like, within the patient's vasculature.

After the procedure is complete, the device(s) may be removed from the sheath 412, and the locator member 414 may be inserted through the hemostatic valve (not shown) into the lumen 416. If the housing 424 is not already provided on the sheath 412, the housing 424 and/or the housing actuator assembly (not shown) may be advanced over or otherwise attached to the proximal end of the sheath 412, preferably before the locator member 414 is inserted into the sheath 412.

As shown in FIG. 26B, when the locator member 414 is fully inserted within the sheath 412, the distal portion 460 extends beyond the distal end 420 of the sheath 412. In an alternative embodiment, the locator member 414 may be attached to an exterior surface (not shown) of the sheath 412, for example, along a track, e.g., cooperating slots, grooves, and the like (not shown) in the sheath 412 and locator member 414. The distal tip 462 preferably is substantially soft and/or flexible such that the distal portion 460 substantially atraumatically enters the vessel 490. In this fully inserted position, cooperating detents (not shown) may be engaged to substantially secure the locator member 414 axially with respect to the sheath 412. The housing actuator assembly (not shown) may be attached to the sheath 412, e.g., by attaching a control wire (not shown) from the housing 424 to the actuator assembly, as described above.

Alternatively, the sheath 412 may include a side port (not shown) at or near its distal end 420 and a bleed back lumen (also not shown) that extends from the side port to the proximal end of the sheath 412. Before or after insertion of the locator member 414, the sheath 412 may be manipulated until "bleed back" (i.e., blood entering the side port and passing proximally through the lumen due to exposure of the side port to blood pressure within the vessel) indicates a desired position for the distal end 420 of the sheath 412. For example, the sheath 412 may be partially withdrawn from the vessel 490 before the locator member 414 is inserted into the sheath 412 to minimize contact between the vessel wall 498 and the distal portion 460 of the locator member 414 during insertion of the locator member 414 into the sheath 412.

Figure 26C:
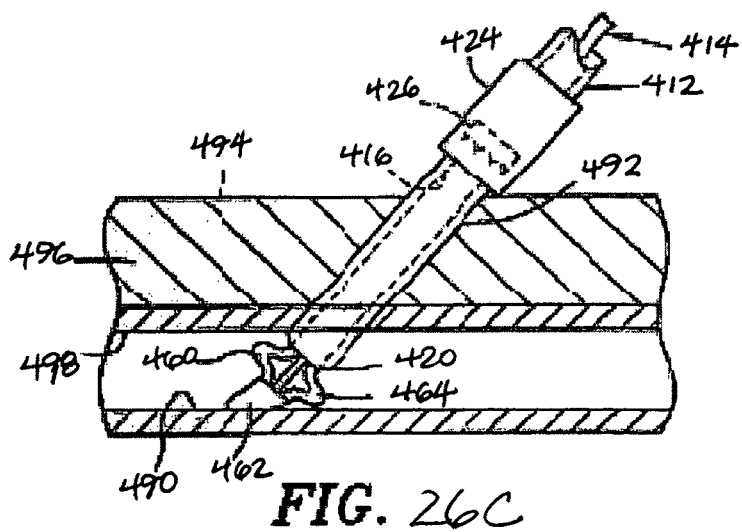
Figure 26D:
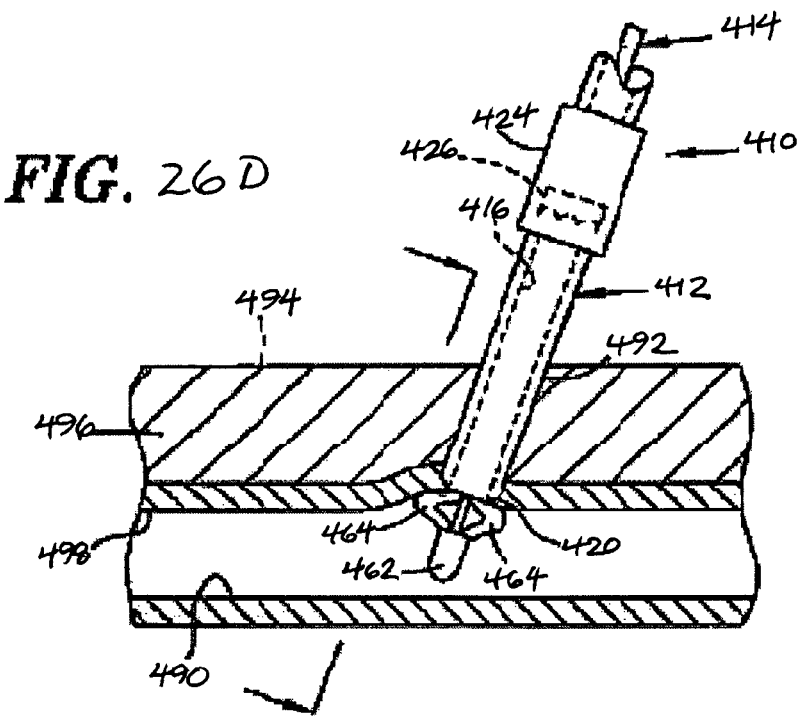

As shown in FIG. 26C, the splines 464 may then be directed to their expanded configuration, for example, by activating a switch on the proximal end (not shown) of the locator member 414. The sheath 412 and locator member 414 may then be moved in conjunction with one another, and preferably are together partially withdrawn from the vessel 490, until the splines 464 contact the wall 498 of the vessel 490, as shown in FIG. 26D. Thus, the splines 464 may provide a tactile indication of the position of the sheath 412 with respect to the wall 498 of the vessel 490. In addition, the splines 464 may assist in "presenting" the wall 498 of the vessel 490, e.g., for receiving a closure element, such as clip 426.

Figure 26E:
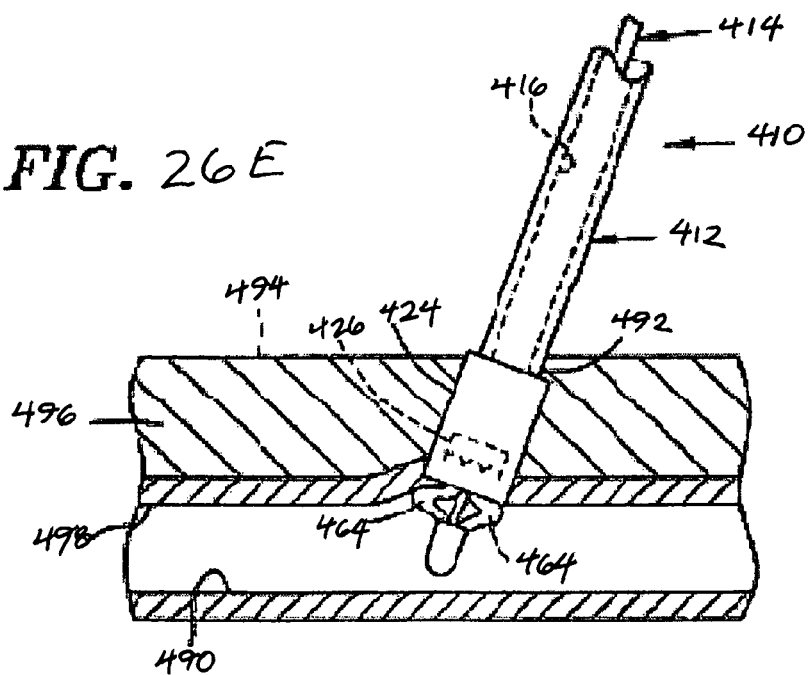

Turning to FIG. 26E, with the sheath 412 properly positioned, the housing 424 may then be actuated, for example, to advance the housing 424 distally into the passage 492 to deliver the clip 426. Preferably, movement of the housing 424 with respect to the distal end 420 of the sheath 412 is limited, e.g., by the housing actuator assembly (not shown), as described above. Preferably, the housing 424 may only be advanced a fixed distance such that the clip 426 substantially engages the wall 498 of the blood vessel, e.g., until the barbs 428 penetrate but do not pass completely through the wall 498. Thus, with the splines 464 fixed with respect to the distal end 420 of the sheath 412 and the distal position of the housing 424 fixed, the clip 426 may be advanced a predetermined distance into the passage 492 that is ascertainable and predictable. This predetermined distance may facilitate proper deployment of the clip 426 with respect to the wall 498 of the vessel 490, e.g., to prevent advancement of the clip 426 too far, i.e., into the vessel 490.

Alternatively, or in addition, the splines 464 include radiopaque markers, such that fluoroscopy and the like may be used to monitor and position the distal portion 460 of the locator member 414. The housing 424 and/or closure element 426 may also include radiopaque markers such that a relative position of the closure element 426 with respect to the splines 464, and consequently to the wall 498 of the vessel 490, may be ascertained before the closure element 426 is deployed from the housing 424.

In a preferred method, the splines 464 automatically return to their collapsed configuration when the closure element 426 is deployed from the housing 424 or when the housing 424 reaches its distal position, as shown in FIG. 26F. For example, the housing actuator assembly (not shown) may contact the locator actuator (also not shown) when the housing actuator assembly is used to advance the housing 424 to its distal position, thereby releasing the locator actuator. This enhancement may avoid any risk of contact between the clip 426 and the splines 464, e.g., which otherwise may risk driving the barbs 428 of the clip 426 through the wall 498 of the vessel 490 and into the splines 464. Alternatively, or in addition, the distal portion 460 of the locator member 414 may be automatically retracted, e.g., into the sheath 412, when the closure element 426 is deployed or the housing 424 is advanced.

Once the clip 426 is successfully deployed within the passage 492, i.e., into the wall 498 of the vessel 490, the apparatus 410 may be withdrawn from the passage 492. If the splines 464 of the locator member 414 are not automatically collapsed during advancement of the housing 424, the splines 464 may first be affirmatively collapsed, e.g., by depressing the locator actuator (not shown). The entire apparatus 410 may then be removed in one step, or alternatively, the locator member 414 may first be withdrawn from the sheath 412 before withdrawing the sheath 412, thereby leaving the clip 426 in place to close and/or seal the passage 492.

Figure 29A:
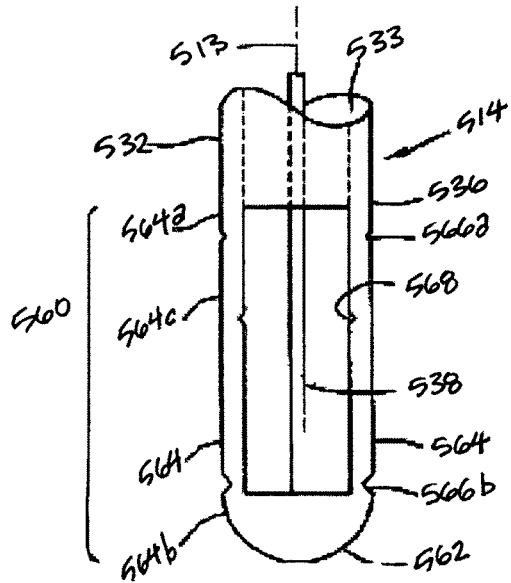
FIGS. 29A and 29B are side views of another embodiment of a distal portion of a locator with positioning elements disposed in collapsed and expanded configurations, respectively.
Figure 29B:
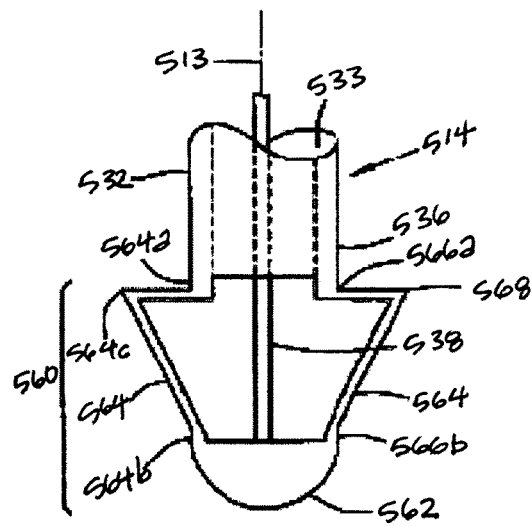

Turning to FIGS. 29A and 29B, another embodiment of a distal portion 560 of a locator member 514 is shown that may be used to position a sheath (not shown) before delivering a closure element (also not shown), similar to the embodiment described above. The locator member 514 includes a flexible or semi-rigid tubular body 532 having a proximal end (not shown) and a distal end 536. An actuator wire or rod 538 is slidably disposed with respect to the body 532, e.g., within a lumen 533 of body 532. The locator member 514 may include a detent (not shown) on or near its proximal end for securing the locator member 514 to a sheath (not shown).

The locator member 514 includes a distal portion 560 that terminates in a substantially rounded, soft, and/or flexible distal tip 562, possibly including a pigtail (not shown) that may facilitate atraumatic advancement of the distal portion 560 into a blood vessel or other body lumen. The locator member 514 preferably has a length relative to the sheath such that the distal portion 560 extends beyond a distal end of the sheath when the locator member 514 is fully received in the sheath, similar to the embodiment described above.

A plurality of splines 564 are provided on the distal portion 560 that may be selectively expandable between a substantially collapsed configuration (shown in FIG. 29A) and a substantially transverse expanded configuration (shown in FIG. 29B). Preferably, the splines 564 are substantially rigid or semi-rigid elements that include hinged regions 566a, 566b and 568 that facilitate expansion substantially transversely with respect to a longitudinal axis 513 of the locator member 514. In one embodiment, each spline 564 is a single piece that includes a plurality of living hinges 566a, 566b and 568. Alternatively, each spline 564 may include multiple segments that are connected by pins or other hinges (not shown). In a preferred embodiment, the distal portion 560 includes four equally spaced splines 564, although the locator member 514 may include more or fewer spines without deviating from the scope of the present invention. Optionally, the splines 564 may include radiopaque markers (not shown), similar to the embodiment described above.

Each spline 564 preferably has a first fixed end 564a and a second movable end 564b. The second end 564b may be axially movable towards the first end 564a to cause an intermediate region 564c of the spline 564 to expand transversely outward, thereby defining the substantially transverse expanded configuration. In a preferred embodiment, the actuator rod 538 extends through the distal portion 560 and is coupled to the second end 564b of the splines 564 and/or to distal tip 562 of the locator member 514. The rod 538 may be moved axially with respect to the body 532 to selectively expand the splines 564 between the collapsed and expanded configurations.

Figure 30A:
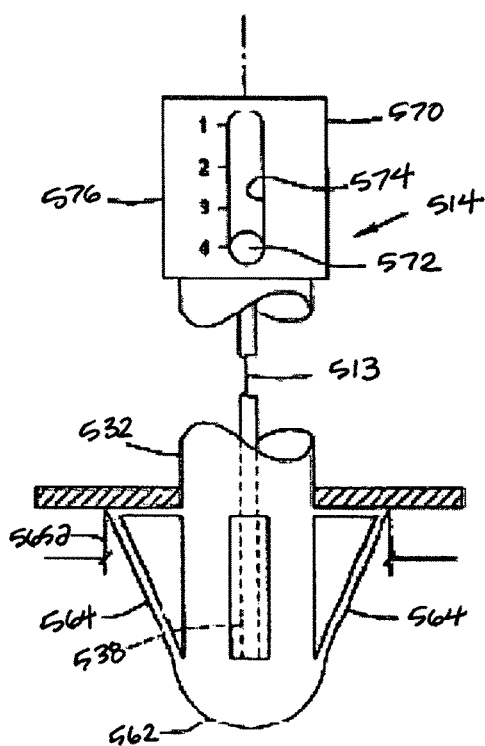
FIGS. 30A and 30B are side views of the locator of FIGS. 29A and 29B, including a control on the locator for adjusting the expansion of the positioning elements.

Turning to FIG. 30A, a locator actuator 570 may be coupled to the control rod 538 and a proximal end 532 of the locator member 514. The locator actuator 570 is configured for directing the control rod 538 axially to selectively expand the splines 564, similar to the embodiment described above.

In addition, the locator actuator 570 may allow the splines 564 to be expanded to one of a plurality of expanded configurations. For example, the locator actuator 570 may include an internal member (not shown), coupled to the control rod 538, that is slidable within an actuator body 576. A button 572 extending from the internal member is slidable in an axial slot 574 in the actuator body 576 for controlling movement of the control rod 538. The button 572 may be moved, thereby moving the control rod 538 and consequently moving the splines 564. For example, as shown in FIG. 30A, the button 572 may be moved to a position (for example, indicated as "4") thereby expanding the splines 564 to an expanded diameter 565a. If desired, the button 572 may be moved to other available positions to reduce the expanded diameter, for example to the diameter 565b shown in FIG. 30B. This control of the expanded diameter of the splines 564 may be useful to allow the splines 564 to be deployed within body lumens of different sizes. Thus, the splines 564 may be expanded to a desired size corresponding to the size of the vessel into which the locator 514 is introduced, thereby minimizing the risk of damage to the vessel due to over expansion of the splines 564.

Figure 30B:
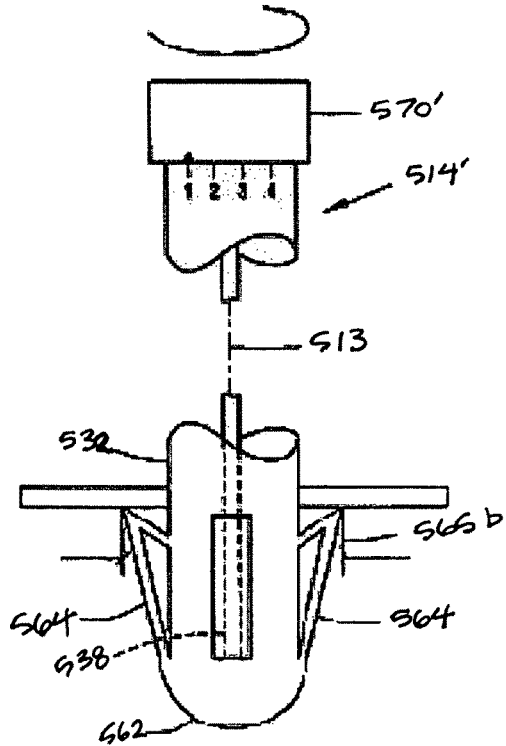

In an alternative embodiment, shown in FIG. 30B, the locator actuator 570' may include a rotatable dial that controls expansion of the splines 564, similar to the linear actuator 570 shown in FIG. 30A. In addition, the locator actuator 570, 570' may include demarcations indicating a size (not shown), e.g., a diameter of the expanded splines and/or the size of the body lumen corresponding to the size of the lumen into which the locator 514 is to be introduced.

Figure 31:
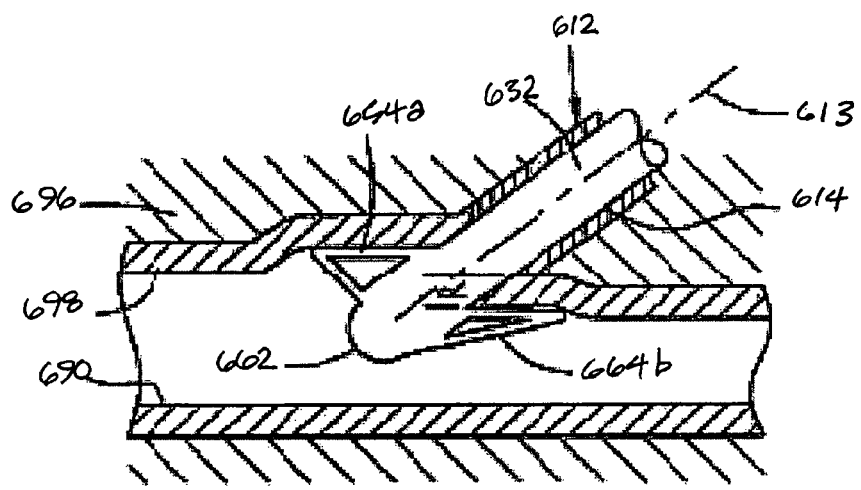
FIG. 31 is a cross-section view of a distal portion of an alternative embodiment of an apparatus for delivering a closure element, in accordance with the present invention.

In a further alternative, shown in FIG. 31, a locator member 614 may be provided that includes splines 664a, 664b that may be selectively expanded to different angles. A locator actuator (not shown) may allow controlled expansion of the splines 664a, 664b to desired angles with respect to the longitudinal axis 613 of the locator member. For example, a cable or other control wire (not shown) may be extend from the locator actuator to each of the splines 664a, 664b, e.g., through a lumen (not shown) in the locator body 632. Each cable may be directed axially to selectively expand or collapse the spline 664a, 664b connected to the respective cable.

For example, a spline 664b on the posterior side of the locator member 614 (away from the surface of the patient's skin) may be expanded towards the proximal end of the locator member 614 at an acute angle alpha, i.e., corresponding substantially to the angle of the passage through the patient's skin to the vessel 690, e.g., about thirty or forty five degrees. In contrast, the spline 664a on the anterior side of the locator member 614 (i.e. towards the surface of the patient's skin) may be expanded away from the proximal end of the locator member 614 at an oblique angle of one hundred eighty degrees less "alpha." Thus, the splines 664a, 664b may be expanded to predetermined angles that facilitate better contact with the wall of the vessel, e.g., to better "present" the vessel wall during deployment of a closure element.

Figure 32:
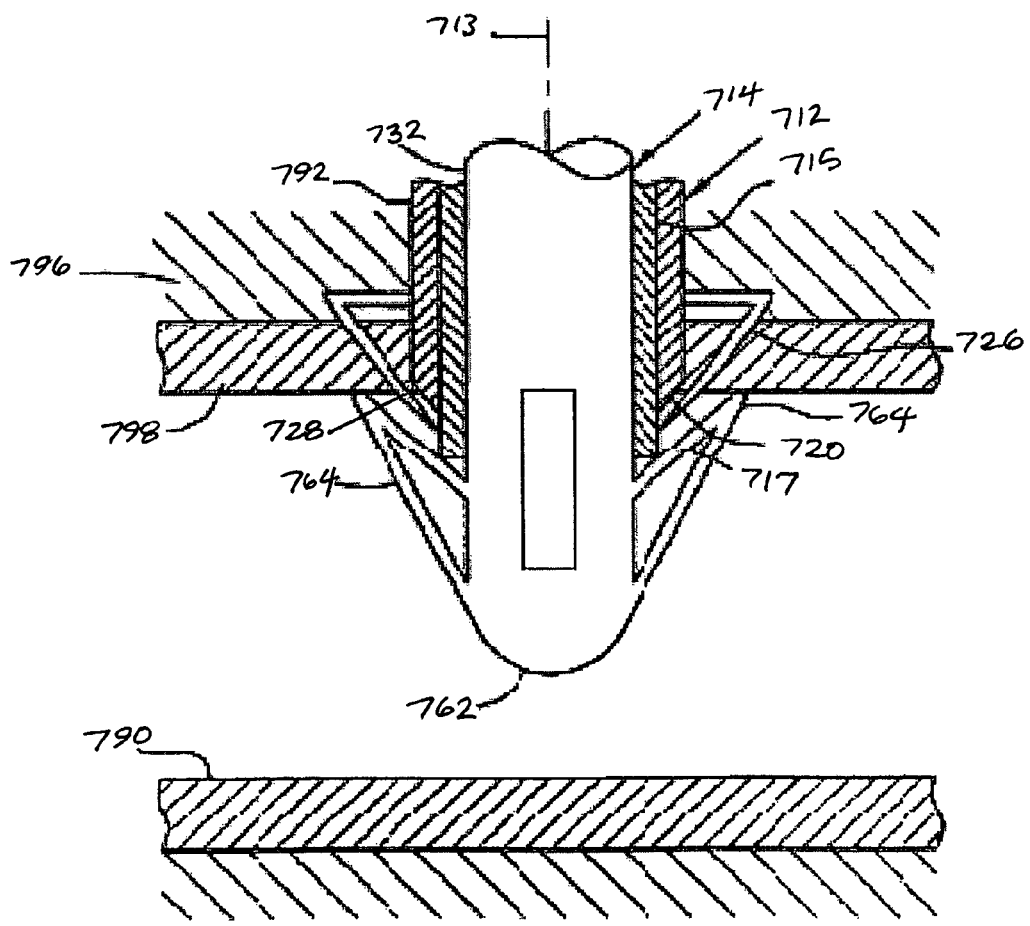
FIG. 32 is a cross-sectional view of a distal portion of yet another alternative embodiment of an apparatus for delivering a closure element, in accordance with the present invention.

In yet another alternative embodiment, shown in FIG. 32, a locator member 714, such as those described above, may include a tubular sleeve 715 within which a body 732, including splines 764, may be axially directed. For example, a proximal end (not shown) of the sleeve 715 may be fixed to a proximal end (also not shown) of the body 732, e.g., to a locator actuator (not shown), such as those described above. At least a distal portion 717 of the sleeve 715 is formed from a substantially rigid, smooth walled tube, such as a hypotube, while the remainder of the sleeve 715 may be a portion of the same tube or may be formed from a substantially flexible or semi-rigid tubular member (not shown).

When the locator member 714 is fully inserted into an introducer sheath 712, such as those described above, the distal portion 717 of the sleeve 715 extends beyond a distal end 720 of the sheath 712. The splines 764 may then be selectively deployed from within the sleeve 715, expanded to a substantially transverse expanded configuration, collapsed, and retracted back into the sleeve 715.

For example, the sheath 712 maybe positioned through a puncture 792 into a vessel 790, e.g., to perform a procedure within a patient's vasculature, as described above. The locator member 714 may then be inserted into the sheath 712 until the distal portion 717 extends beyond the distal end 720 of the sheath 712. The splines 764 may then be expanded, and the sheath 712 and locator member 714 manipulated to a desired position, e.g., such that the splines 764 contact the wall 798 of the vessel 790, thereby providing a tactile indication of the position of the sheath 712.

A closure element, such as clip 726 may then be deployed, e.g., from a housing (not shown) slidably mounted on the sheath 712. Barbs or tines 728 on the clip 726 penetrate into the wall 798 of the vessel 790, e.g., to close the opening in the wall 798 of the vessel 790, as described above. If the barbs 728 penetrate completely through the wall 798 of the vessel 790, the sleeve 715 protects the splines 764 and/or the body 733 of the locator member 714. The barbs 728 may engage but not penetrate or otherwise catch on the distal portion 717 of the sleeve 715, because of its substantially rigid and/or smooth construction. Thus, the barbs 728 may not penetrate or otherwise catch on the splines 764 when the clip 726 is deployed. The splines 764 may be collapsed and retracted into the sleeve 715, either manually or automatically, similar to the embodiments described above. When the sheath 712 is withdrawn from the puncture 792, the barbs 728 may slide along the distal portion 717 of the sleeve 715 until the distal portion 717 is withdrawn from within the clip 726, whereupon the barbs 728 may move inwards to close and/or seal the opening in the wall 798 of the vessel 790.

In alternative embodiments, the apparatus and methods of the present invention may be used to locate an introducer sheath within a blood vessel and/or to deliver closure elements other than a clip. For example, the apparatus may be used to deliver a collagen plug and the like into the passage, or a sealing material (either alone, or in conjunction with a clip).

VI. Fifth Closure System Embodiment

Turning to FIGS. 33-36, which show a first preferred embodiment of an apparatus 810 for delivering a closure element, such as a clip 805 (shown in phantom), into an opening through tissue for closing the opening (not shown). Generally, the apparatus 810 includes an introducer sheath 812, a housing or carrier assembly 814 slidably disposed on the sheath 812, and an actuator or actuator assembly 816 that is connectable to the introducer sheath 812. In addition, the apparatus 810 may also include a locator member or obturator 818, which may be part of the actuator assembly 816, as shown in FIGS. 33-35.

As best seen in FIGS. 33 and 36, the introducer sheath 812 is generally a substantially flexible or semi-rigid tubular member including a lumen 820 extending along a longitudinal axis 828 between its proximal and distal ends 822, 824. The distal end 824 has a size and shape to facilitate insertion into an opening through tissue (not shown), e.g., having a tapered tip 826 for facilitating substantially atraumatic introduction through a passage and/or at least partially into a blood vessel or other body lumen accessed via the passage. The lumen 820 has a size for accommodating insertion of one or more devices therethrough, such as a catheter, guidewire, and the like (not shown).

Returning to FIGS. 33, 36, and 37, a hub assembly 830 is attached to the proximal end 822 of the sheath 812, e.g., by an adhesive, cooperating connectors, and/or a thermo-mechanical joint. Thus, the hub assembly 830 and the sheath 812 may define a passage 838 (see FIG. 33) therebetween that extends substantially parallel to the longitudinal axis 828. The hub assembly 830 may include a keel member 1020 and one or more outer annular bodies 1022-1026 that may be attached to one another, e.g., using butt or lap joints secured with adhesives, mechanical connectors, and the like.

For example, the hub assembly 830 may include a rear main body 1022, a spacer 1023, a nose ring 1024, and a strain relief forward nose 1026 that may be substantially permanently attached to one another. The keel member 1020 may include a tubular portion 1046, and a shoulder portion 1048 connected by a radial spoke 1050 that may extend transversely with respect to the longitudinal axis 828. The proximal end 822 of the sheath 812 may be connected to the tubular portion 1046 such that a passage 1052 through the tubular portion 1046 communicates with the lumen 820. The main body 1022 and nose ring 1024 may be connected to the shoulder portion 1048 such that an annular passage 838 may be defined between the tubular portion 1046 and the main body 1022 and nose ring 1024. The passage 838 may have a "C" shape along the portion of the hub assembly 830 through which the spoke 1048 of the keel member 1020 extends.

With particular reference to FIG. 36, the hub assembly 830 may also include one or more seals and/or valves that provide a fluid-tight seal. Thus, one or more devices, such as the obturator 818 (not shown in FIG. 36), may be inserted into the lumen 820 of the sheath 812 without fluid passing proximally through the lumen 820. For example, the hub assembly 830 may include a thrust washer and/or valve 1028, a valve 1030, a guide 1032 for directing devices into the lumen 820 of the sheath 812, and a seal 1034. The various seals and/or guides may be secured to the hub assembly 830 by a spacer 1036 and/or an end cap 1038.

In addition, the hub assembly 830 may include one or more connectors on its proximal end 832, such as tabs 834 (see FIG. 33) and/or recesses or pockets (not shown) for cooperating with mating connectors on the actuator assembly 816, as described further below. Optionally, the hub assembly 830 may also include a side port 836 that extends from the shoulder portion 1048 to the passage 1052, thereby communicating with the lumen 820. The side port 836 may communicate with tubing 837 (see FIG. 35A), for example, to infuse fluids into the lumen 820 through the sheath 812. Alternatively, or in addition, the side port 836 may provide a "bleed back" indicator, such as that disclosed in application U.S. Pat. No. 6,626,918, which is incorporated herein by reference.

Returning to FIG. 36, the carrier assembly 814 is slidably disposed on an exterior of the sheath 812 and is configured for releasably holding the clip 805. The carrier assembly 814 is preferably slidable from a proximal position, e.g., near, adjacent to, or at least partially disposed within the passage 838, to one or more distal positions towards the distal end 824 of the sheath 812, as explained further below. Optionally, the hub assembly 830 may include a carrier release pin 1040 that may be inserted into a hole, slot, or other aperture 1042 in the shoulder portion 1048. An inner tip 1044 of the pin 1040 may be received in one or more corresponding holes 851, 861, 871 (best seen in FIG. 38A) in the carrier assembly 814. The pin 1040 may provide a safety feature, e.g., preventing premature advancement of the carrier assembly 814 and/or deployment of the clip 805, and/or may assist in aligning the carrier assembly 814 as will be appreciated by those skilled in the art.

As best seen in FIGS. 38A and 38B, the carrier assembly 814 may include an inner carrier member 840, a middle pusher member 842, and an outer anchor member 844 that may be nested together and coaxially disposed around the sheath 812 (shown in phantom in FIG. 38B). The carrier member 840 is an annular-shaped body 832 including proximal and distal ends 846, 848. As used herein, an "annular-shaped body" or "annular body" (whether referring to the carrier assembly 814 or the clip 805) includes any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis.

A tongue 850 may extend proximally from the proximal end 846 substantially parallel to the longitudinal axis 828. The tongue 850 may include a tab 852 or other connector, having a ramped proximal edge 852a and a substantially blunt distal edge 852b, for coupling movement of the carrier member 840 to the actuator assembly 816, as described further below. The distal end 848 of the carrier member 840 may be tapered or otherwise configured for facilitating substantially atraumatic advancement of the carrier member 840 through tissue, also as described further below.

The pusher member 842 is also an annular body 854, including proximal and distal ends 856, 858 and a tongue 860 extending from the proximal end 856 having a tab 862 thereon. The pusher member 842 is configured to slidably fit around the carrier member 840, but has a substantially shorter length than the carrier member 840. Thus, the carrier and pusher members 840, 842 may at least partially define a space 815 distal to the distal end 858 of the pusher member 842 and along an outer surface of the carrier member 840.

The anchor member or ring 844 may also be an annular body 864, including proximal and distal ends 866, 868 and a tongue 870 extending from the proximal end 866 having a tab 872 thereon, similar to the carrier and pusher members 840, 842. The anchor member 844 preferably includes an outer skin or sleeve 845 (shown in phantom in FIG. 38B) attached to and extending distally from the distal end 868 of the anchor ring 844, thereby extending over the space 815 to define a space (not shown). For example, the outer sleeve 845 may be lapped over and/or bonded to the anchor member 844.

The outer sleeve 845 may be formed from a substantially flexible material, which may be inelastic or elastic, and/or may include a substantially slippery outer surface. Exemplary materials include polytetrafluoroethylene (PTFE), polyethylene terephthalate (PET) or other polyester, latex, silicone, polyamides, polyurethanes, and/or blends or copolymers thereof. The outer sleeve 845 may have a length that is substantially longer than the carrier member 840 such that the outer sleeve 845 extends beyond the distal end 848 of the carrier member 840. For example, the outer sleeve 845 may extend up to fifteen millimeters (15 mm) or more beyond the carrier member 840 and/or may slidably surround the sheath 812. The outer sleeve 845 may protect the clip 805 or tissue through which the carrier assembly 814 is advanced, and/or may facilitate advancing the carrier assembly 814 through multiple layers of tissue, as explained further below.

Figure 38C:
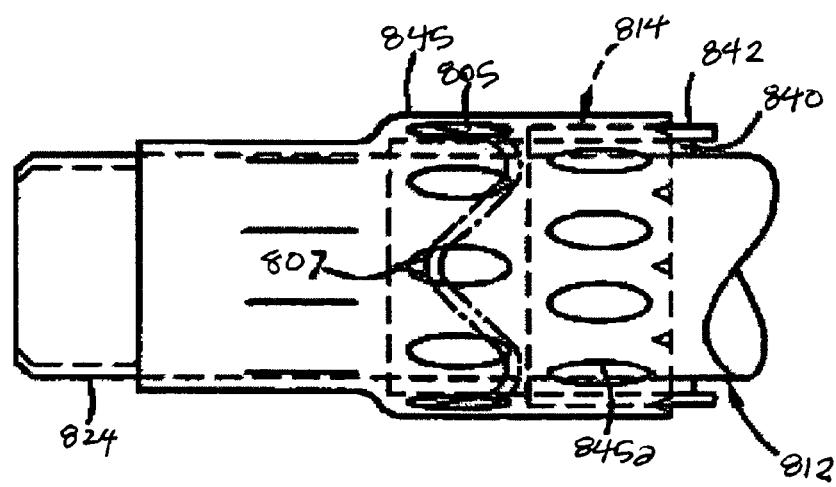
FIG. 38C is a side view of the carrier assembly of FIGS. 38A and 38B, showing slots in an outer sleeve expanding to accommodate advancing the carrier and pusher members relative to the anchor member.
Figure 38D:
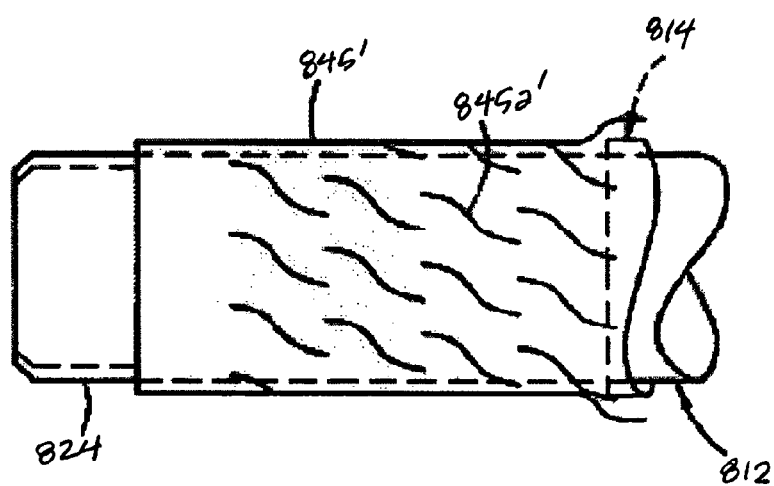
FIG. 38D is a side view of an alternative embodiment of the carrier assembly of FIG. 38C, showing spiral slots in the outer sleeve.

Optionally, the outer sleeve 845 may include weakened regions, e.g., longitudinal slots or perforations 845a or thin walled regions (not shown), that may be torn, expanded, and/or enlarged during advancement of the carrier and pusher members 840, 842 relative to the outer sleeve 834, as explained further below. For example, the outer sleeve 845 may include a plurality of longitudinal slots 845a with circumferentially adjacent slots being staggered longitudinally from one another, as shown in FIG. 38C. This slot arrangement may facilitate the outer sleeve 845 expanding or being deflected out of the way upon advancing the carrier and pusher members 840, 842 without fully exposing the clip 805, as explained further below. Alternatively, as shown in FIG. 38D, the longitudinal slots may be spiral slots 845a' formed in the outer sleeve 845,' Spiral slots 845a' may minimize tissue moving as the carrier assembly 814 is advanced through tissue (not shown), as described further below.

In a further alternative, a substantially flexible sleeve or skin (not shown) may be provided that extends over the space 815, similar to the outer sleeve 845, but that may be bonded or otherwise secured to the outer surface of the introducer sheath 812. Embodiments of such a skin may be found in U.S. Pat. No. 6,749,621, which is incorporated herein by reference. In yet another alternative, it may be possible to eliminate the anchor member 844 and/or the outer sleeve 845 completely, such that the clip 805 remains exposed on the carrier member 840.

In a preferred embodiment, the carrier, pusher, and anchor members 840, 842, 844 are coaxially disposed with respect to one another such that they telescope at least partially within one another. When the carrier, pusher, and anchor members 840, 842, 844 are coaxially disposed, the tongues 850, 860, 870 preferably overlap and/or are coextensive with one another, as shown in FIG. 38B). The tabs (only tab 872 is shown in FIG. 38B) may also be aligned with one another. Each of the tongues 850, 860, 870 is preferably tapered to facilitate attachment of the actuator assembly 816, as described further below. The tongues 850, 860, 870 may include holes 851, 861, 871 that may be aligned with one another when the carrier, pusher, and anchor members 840, 850, 860 are aligned within one another. The holes 851, 861, 871 may be sized for receiving a pin 1040 (not shown, see FIGS. 35A and 36), or an alignment detent (not shown) for ensuring that the carrier, pusher, and anchor members 840, 850, 860 are properly aligned over one another before using the apparatus 810.

The carrier assembly 814 may be used to deploy a clip 805 or other closure element from the space 815 defined by the carrier assembly 814. In a preferred embodiment, the clip 805 is a generally annular-shaped clip, including one or more barbs and/or tines 807 for engaging the tissue around an opening, e.g., in or adjacent to a wall of a blood vessel (not shown). Preferably, the clip 805 is configured for drawing the tissue around a puncture in the wall of the vessel substantially closed and/or for enhancing hemostasis within the puncture. Exemplary embodiments of a closure element are disclosed in U.S. Pat. Nos. 6,197,042, 6,461,364, 6,391, 048, 6,623,510, which are incorporated herein by reference.

Returning to FIGS. 33 and 35A, the carrier assembly 814 is actuable from the proximal end 822 of the sheath 812, preferably by the actuator assembly 816. The carrier assembly 814 may be substantially permanently, but slidably, disposed on the sheath 812. For example, the carrier assembly 814 may be initially stored at least partially within the passage 838 under the hub 830, e.g., under the strain relief nose 1026. Alternatively, the carrier assembly 814 may be provided separate as a separate assembly (not shown), e.g., with the clip 805 pre-loaded therein, that may be slidably received on the sheath 812.

Turning to FIGS. 33-35B, 39A, and 39B, the actuator assembly 816 generally includes a handle body or housing 874 and a plurality of telescoping actuator members 876, 878, 880. Preferably, the housing 874 includes mating handle covers 874a, 874b, and a nose cover 875 within which the actuator members 876, 878, 880 are slidably mounted. The handle body 874 may include one or more cooperating connectors for connecting the actuator assembly 816 to the sheath 812. For example, the nose cover 875 may include pockets 884 (see FIG. 33) for receiving tabs 834 on the hub assembly 830. Thus, the actuator assembly 16 may be substantially permanently attached to the sheath 812, as described further below. In addition, the actuator assembly 816 may include a frame subassembly 990, and side-plates 991, which may secure the obturator assembly 818 relative to the housing 874, as explained further below.

In the preferred embodiment shown in FIGS. 39A and 39B, the telescoping actuator members 876, 878, 880 include an inner tubular member 876, an intermediate tubular member 878, and an outer tubular member 880. Preferably, the actuator members 876-880 are substantially rigid members having longitudinal slots 886, 888, 890 therein, thereby defining generally "C" shaped cross-sections over at least a substantial portion of their lengths. Each of the longitudinal slots 886, 878, 890 may have a width similar to a width of the tongues 850, 860, 870 on the carrier assembly 814, as described further below. The longitudinal slots 886, 878, 890 extend predetermined distances from distal ends 892, 894, 896 of the respective tubular members 876, 878, 880 towards, but not necessarily completely to, their proximal ends (not shown).

The distal ends 892, 894, 896 include detents for engaging respective detents on the carrier assembly 814. For example, the detents may be pockets 904, 906, 908 including a tapered proximal edge and a substantially blunt distal edge (only edges 908a, 908b are shown and labeled in FIG. 39B), similar to the respective tabs 852, 862, 872 on the carrier, pusher, and anchor members 840, 842, 844 (see FIG. 38A). Thus, movement of the carrier, pusher, and anchor members 840, 842, 844 may be coupled to the inner, intermediate, and outer actuator members 876, 878, 880, respectively, when the tongues 850, 860, 870 are received in the slots 886, 888, 890.

Returning to FIGS. 33-35A, the actuator assembly 816 also includes a control member, such as knob 910 and shaft 912, that are coupled to the inner, intermediate, and/or outer actuator members 876, 878, 880. Preferably, the shaft 912 is connected only to the intermediate actuator member 878. Thus, axial movement of one or more of the actuator members 876, 878, 880 may be attained by applying an axial force to the knob 910.

The inner, intermediate, and outer actuator members 876-880 include one or more sets of cooperating detents for coupling distal movement of the inner, intermediate, and outer actuator members 876-880 in a predetermined manner, as the knob 910 is directed distally. The term "detents" refers to any combination of mating elements, such as tabs, pockets, slots, ramps, cantilevered members, and the like, that may be selectively or automatically engaged and/or disengaged to couple or decouple the actuator members 876-880 relative to one another. The cooperating detents described below are merely exemplary and not exhaustive.

Preferably, the cooperating detents include a first set of cooperating detents for releasably coupling the outer tubular member 880 to the inner and intermediate tubular members 876, 878. When the carrier assembly 814 reaches a first distal position, e.g., near the distal end 824 of the sheath 812, the outer tubular member 880 may be decoupled and preferably anchored from further substantial axial movement. As the knob 910 is directed further distally, the inner and intermediate tubular members 876, 878, and consequently the carrier and pusher members 840, 842, may continue to be directed distally, while the outer tubular member 880 and the sheath member 844 remain anchored in place.

FIGS. 40A and 40B show a preferred embodiment of a first set of cooperating detents for releasably coupling the outer tubular member 880 to the inner and intermediate tubular members 876, 878. The outer tubular member 880 includes a first detent or tab 914 (or optionally multiple detents, not shown) and the inner and intermediate tubular members 876, 878 include first pockets 916, 918 for receiving the first tab 914 therein. Thus, with the first tab 914 received in the first pockets 916, 918, any axial force (in either direction) moving one of the tubular members 876-880 moves all of them.

First and second ramps 920, 922 are provided on the outer tubular member 880 and the housing 874 of the actuator assembly 816 (only a portion of which is shown) of the sheath 812 (not shown). The first and second ramps 920, 922 slidably engage one another as the actuator members 876, 878, 880 and/or the carrier assembly 814 (not shown) reach the first distal position. Alternatively, the second ramp 922 may be provided on a portion of the hub assembly 830 (not shown). Preferably, the first ramp 920 on the outer tubular member 880 defines a free end of a first cantilevered beam 924 from which the first tab 914 extends inwardly. The beam 924 includes a hole 926 therethrough and the second ramp 922, which is relatively stationary, includes a recess or other feature 928 therein.

The actuator members 876, 878, 880 may be advanced distally (in direction of arrow) until the cooperating first and second ramps 920, 922 slidably engage one another. As the actuator members 876, 878, 880 are advanced further distally, the first ramp 920 slides up onto the second ramp 922, thereby deflecting the first beam 924 outwardly until the first tab 914 is disengaged from the first pockets 916, 918, as shown in FIG. 40B. Further, upon attaining the first distal position, a surface 929 in the hole 926 on the flange 924 and the feature 928 in the second ramp 922 preferably interlock or otherwise contact one another. This contact may secure the outer tubular member 880 from subsequent axial movement, while still allowing the inner and intermediate tubular members 876, 878 to be directed distally beyond the first distal position. In an alternative embodiment, it may be possible to eliminate the ramp 920 on the first beam 924, while still allowing the free end of the first beam 924 to be deflected radially outward by the second ramp 922.

In addition to the first set of cooperating detents described above, the actuator assembly 816 may include a second set of cooperating detents for releasably coupling the inner tubular member 876 and the intermediate tubular member 878 and/or recoupling the inner and outer tubular members 876, 880. Thus, the inner and intermediate tubular members 876, 878 may be directable to a second distal position distal to the first distal position (while the outer tubular member 880 remains substantially stationary). When the carrier and pusher members 840, 842 approach the second distal position, the cooperating detents may decouple the intermediate tubular member 878 from the inner tubular member 876 and/or anchor the inner tubular member 876 in place, e.g., relative to the outer tubular member 880. The intermediate tubular member 878, and consequently the pusher member 842 (not shown), may then be advanced further distally beyond the second distal position, as described further below.

Turning to FIGS. 41A-41D, an exemplary second set of cooperating detents is shown that includes a second tab or other detent 930 on the intermediate tubular member 878 and a second pocket 932 in the inner tubular member 876. The second tab 930 may be received in the second pocket 932 for coupling movement of the inner and intermediate tubular members 876, 878 together.

The outer tubular member 880 includes a spring element 938 that is configured for disengaging the second tab 930 from the second pocket 932 upon attaining the second distal position. For example, the spring element 938 may include a transverse beam 940 that extends from a third cantilevered beam 941 on the outer tubular member 880. The transverse beam 940 extends through slots 942, 944 in the inner and intermediate tubular members 876, 878, e.g., transversely to the longitudinal axis 828, and preferably substantially perpendicular to the longitudinal axis 828.

Preferably, the transverse beam 940 has an inverted "T" shape, as best seen in FIGS. 41C and 41D, defining one or more shoulders 946 adjacent a stem 948. The slots 942, 944 may have narrow regions 942a, 944a and wide regions 942b, 944b proximal to the narrow regions 942a, 944a. Preferably, the narrow regions 942a, 944a have a width less than the shoulders 946, but wider than the stem 948. In contrast, the wide regions 942b, 944b have a width greater than a width of the shoulders 946. In addition, the narrow regions 942a, 944a and wide regions 942b, 944b are disposed along the longitudinal axis 828 at predetermined locations such that the transverse beam 940 coincides with the wide regions 942b, 944b approximately at the second distal position.

Consequently, before the inner and intermediate tubular members 876, 878 reach the second distal position, the shoulders 946 may slide along the outer surface of the intermediate tubular member 878 while the stem 948 slides inside the narrow region 942a, 944a of the slots 942, 944. Alternatively, the shoulders 946 may slide along an outer surface (not shown) of the inner member 876 if the slot 944 is wide its entire length. The tip 950 of the transverse beam 940 may move along the inner tubular member 876, e.g., at a predetermined clearance from the inner surface thereof such that the tip 950 does not touch the inner surface of the inner tubular member 876. Alternatively, the tip 950 may slide along the inner surface of the inner tubular member 876.

When the inner and intermediate tubular members 876, 878 approach or attain the second distal position, the shoulders 946 may enter the wide regions 942b, 944b, e.g., due to the bias of the beam 941. This action may produce two substantially simultaneous results. First, when the shoulders 946 enter the wide regions 942b, 944b, i.e., such that the beam 940 moves transversely, the tip 950 of the beam 940 may push the second tab 930 radially outward, thereby disengaging the second tab 930 from the second pocket 932. Thus, further distal movement of the intermediate tubular member 878 may be allowed independent of the inner tubular member 876. In addition, the shoulders 946 of the beam 940 may enter the wide region 942b of the slot 942. Because the wide region 942b has a size corresponding substantially to a cross-section of the transverse beam 940, the inner tubular member 876 is consequently coupled to the outer tubular member 880 as it is disengaged from the intermediate tubular member 878.

Thus, the inner tubular member 876 may be substantially locked in place, e.g., to the outer tubular member 880 since the outer tubular member 880 has been previously secured in place. Preferably, these two actions, i.e., releasing the intermediate tubular member 880 and securing the inner tubular member 876 in place occur substantially simultaneously.

Returning to FIGS. 33-35B, the actuator assembly 816 also includes the obturator assembly 818 mounted within the housing 874. Generally, the obturator assembly 818 includes a flexible or semi-rigid tubular body or other elongate rail 972 having a proximal end 974, a distal end 976, and a distal portion 984. An actuator rod, wire, or other elongate member 978 is slidably disposed with respect to the rail 972, e.g., within a lumen of the rail 972.

In addition, the obturator assembly 818 includes an obturator housing 980 on the proximal end 974 of the rail 972.

The obturator housing 980 may include one or more tabs 992 for engaging complementary slots 994 in the side plates 991. Thus, the obturator assembly 818 may be secured within the housing 874 of the actuator assembly 816 when the tabs 992 are received in the slots 994. The side plates 991 may be connected to the frame subassembly 990, and the handle covers 874a, 874b are secured over the side plates 991. When the obturator assembly 818 is mounted within the housing 874, the rail 972 may extend through the actuator members 876, 878, 880, e.g., until the distal portion 982 extends beyond the distal ends 892, 894, 896 of the actuator members 876, 878, 880.

Figures 42A, 42B:
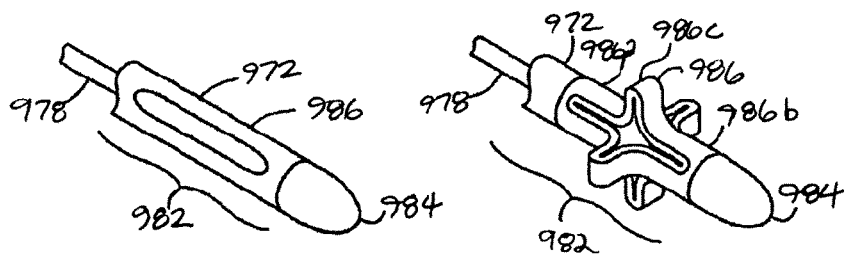
FIGS. 42A and 42B are perspective views of the distal end of the obturator of FIG. 35B, showing positioning elements on the obturator in collapsed and expanded configurations, respectively.

Turning to FIGS. 42A and 42B, the distal portion 982 of the obturator assembly 818 includes a substantially rounded, soft, and/or flexible distal tip 984. Optionally, the distal tip 984 may include a pigtail (not shown) that may facilitate atraumatic advancement of the distal portion 982 into a blood vessel or other body lumen (not shown). The obturator assembly 818 preferably has a length relative to the sheath 812 such that the distal portion 982 extends beyond the distal end 824 of the sheath 812 when the obturator assembly 818 is in a deployed position (shown in FIGS. 44C and 44D), as explained below.

One or more, and preferably a plurality of, positioning elements 986 are provided on the distal portion 982 that may be selectively expandable between a substantially axial collapsed configuration (shown in FIG. 42A) and a substantially transverse expanded configuration (shown in FIG. 42B). Preferably, the positioning elements 186 are substantially flexible splines configured for expanding substantially transversely with respect to the longitudinal axis 828.

In one embodiment, the obturator assembly 818 includes four splines 986 that are substantially equally spaced about the distal portion 982. Alternatively, the obturator assembly 818 may include a pair of splines (not shown) that are disposed generally opposite one another about the distal portion. The obturator assembly 818 may include more or fewer splines without deviating from the scope of the present invention. Additional embodiments of positioning elements are disclosed in co-pending application U.S. Pat. No. 6,780,197, the disclosure of which is expressly incorporated herein by reference.

Optionally, the splines 986 may include radiopaque markers (not shown) or may be wholly or partially formed from radiopaque material to facilitate observation of the splines 986 using fluoroscopy or other imaging systems. Alternatively, or in addition, the carrier assembly 814 may include one or more radiopaque markers, e.g., at its distal end (not shown) and/or the clip 805 may include radiopaque marker(s) or may be made from radiopaque material. This may facilitate monitoring the location of the clip 805 relative to the splines 986, as described further below.

Returning to FIGS. 42A and 42B, each spline 986 preferably has a first fixed (e.g., proximal) end 986a and a second movable (e.g., distal) end 986b. The second end 986b may be axially movable towards the first end 986a to cause an intermediate region 986c of the spline 986 to buckle and/or expand transversely outwardly, thereby defining the substantially transverse expanded configuration. In a preferred embodiment, an actuator rod 978 extends through the distal portion 982 and is coupled to the distal tip 984 of the obturator assembly 818 and/or to one of the first and second ends 986a, 986b. The actuator rod 978 may be moved axially, e.g., proximally, with respect to the rail 972 to selectively expand the splines 186 between their collapsed configuration and their expanded configuration.

Figure 44A:
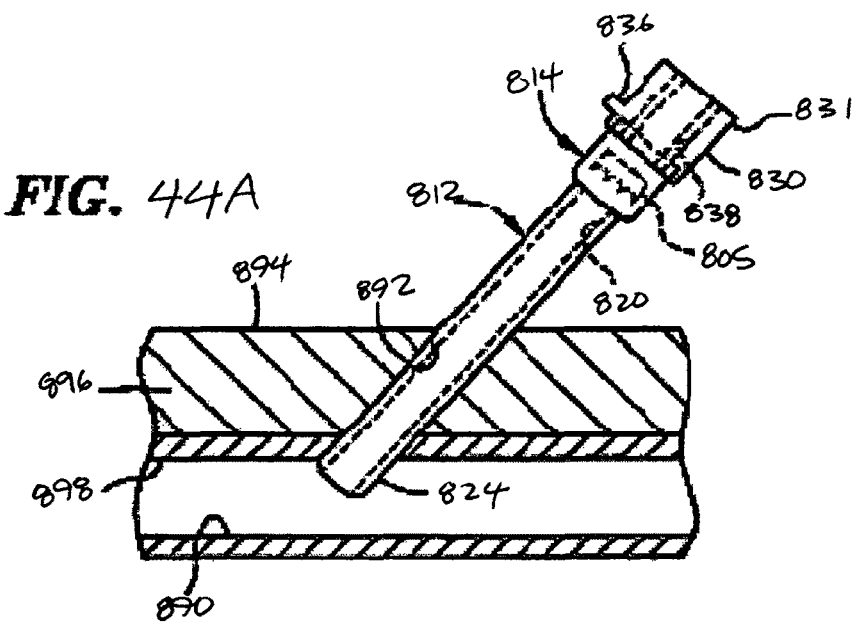
Figure 44B:
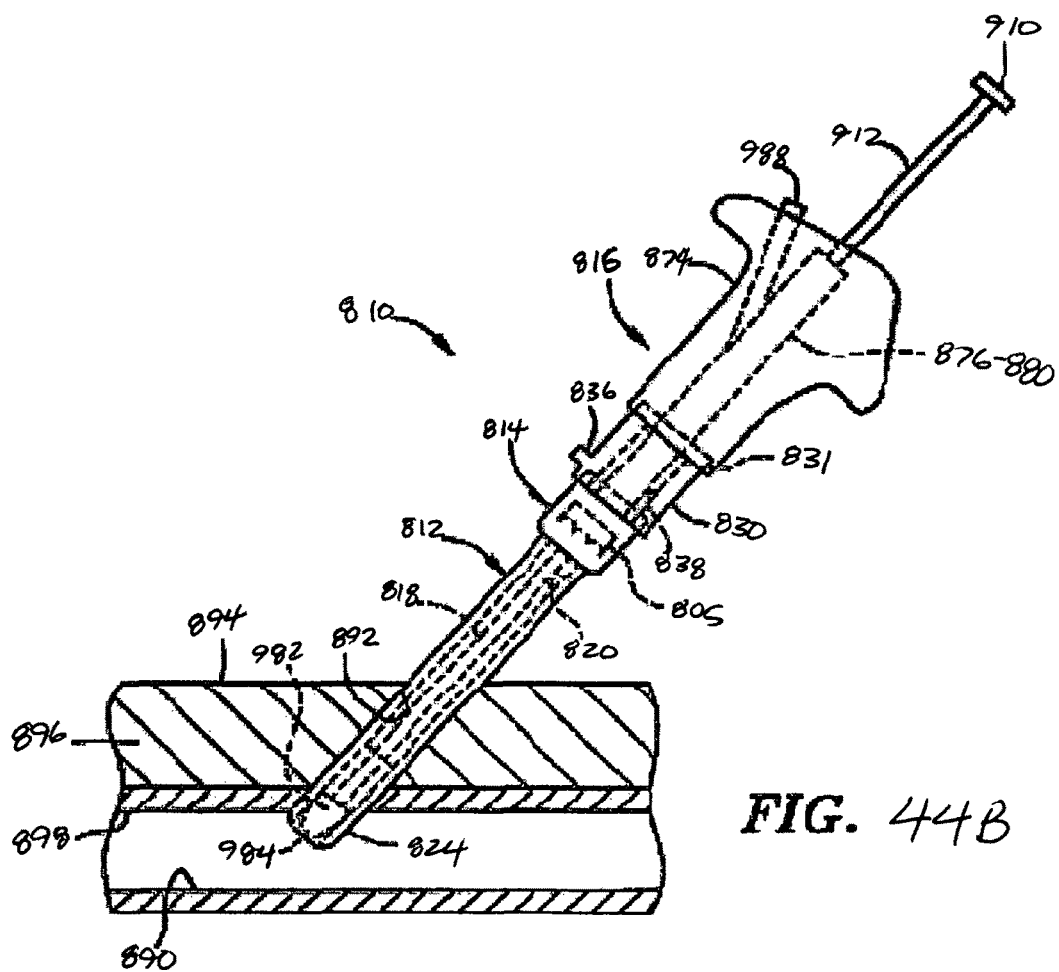
Figure 44C:
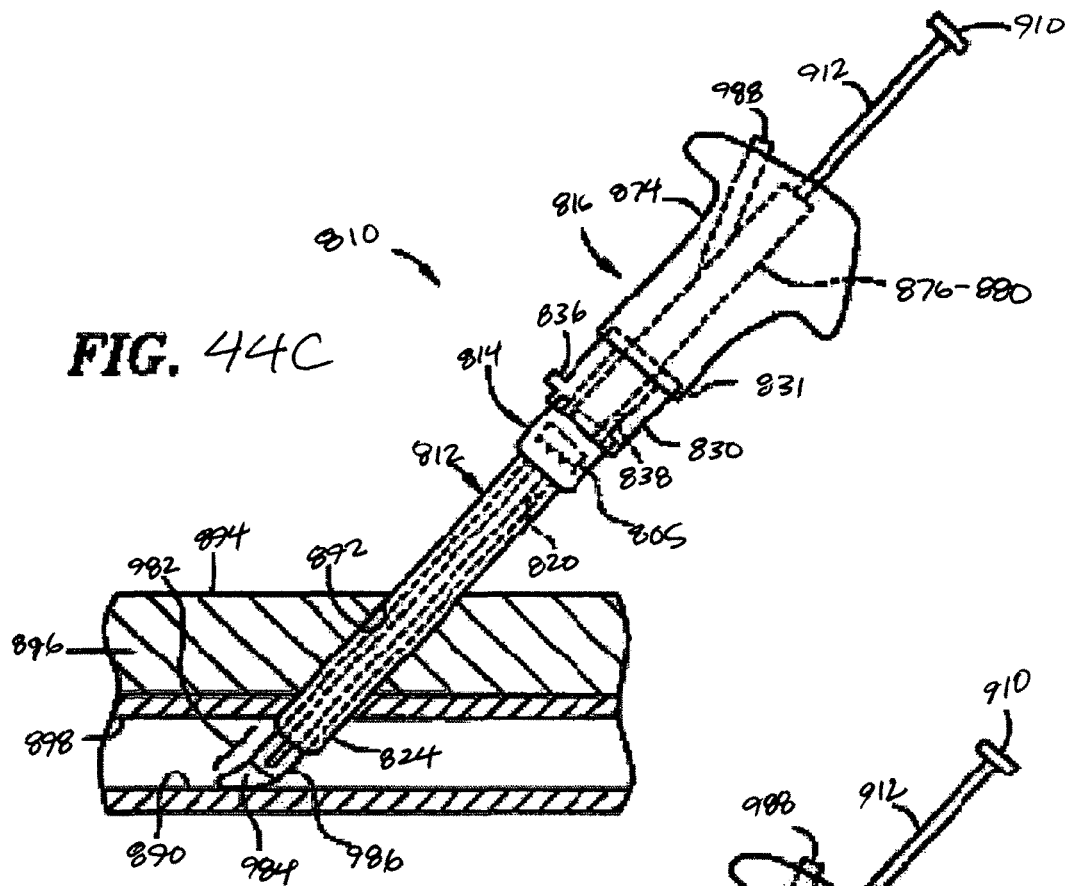
Figure 44D:
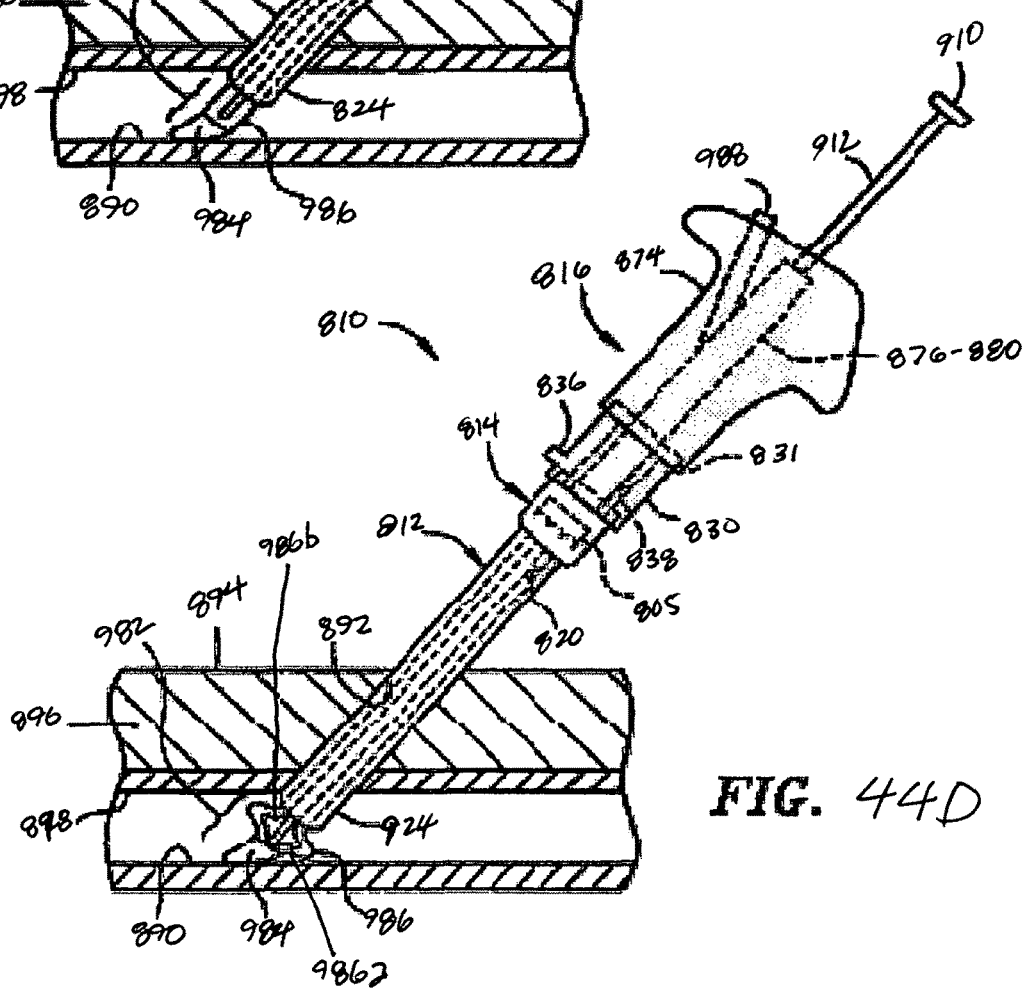

Turning to FIGS. 44B-44D, the obturator housing 980 (not shown, see FIG. 35A) is configured for selectively deploying the distal portion 982 and/or moving the splines 986 between their collapsed and expanded configurations. For example, the obturator housing 980 may include a switch 988 that may be depressed or rotated. Initially, as shown in FIG. 44B, the distal portion 982 may be retracted within the distal end 824 of the sheath 812. As the switch 988 is activated, e.g., depressed, the distal portion 982 may be deployed from the distal end 824 of the sheath 812, as shown in FIG. 44C. As the switch is further depressed, the splines 986 may be expanded to the expanded configuration, as shown in FIG. 44O.

For example, the rail 972 and rod 978 may initially be moved together, e.g., to deploy the distal portion 982, as shown in FIG. 44C. Once deployed, the rod 978 may stop moving, the rail 972 may continue to advance, thereby buckling the splines 986 as the first and second ends 986a, 986b become closer to one another, as shown in FIG. 44D. Alternatively, after deploying the distal portion 982, the rod 978 may be retracted proximally to expand the splines 986.

The obturator housing 980 (see FIG. 35A) preferably includes a lock 989 for securing the rod 978 and rail 972 relative to one another, e.g., to lock the splines 986 in their expanded configuration. The lock may be released, for example, by depressing the switch 988 again, by activating an emergency release (not shown) and/or by activating a release mechanism (not shown) when the carrier assembly 814 is advanced, as explained below. The obturator housing 980 may include a spring or other biasing mechanism (not shown) for biasing the rail 972 and/or rod 978 to return the splines 986 to their collapsed configuration and/or to retract the distal portion 982 back into the sheath 812 when the lock is released. For example, the lock may be released upon advancing the actuator members 876, 878, 880 to a predetermined position, e.g., before or after attaining the second distal position, as explained further below.

Figure 43A:
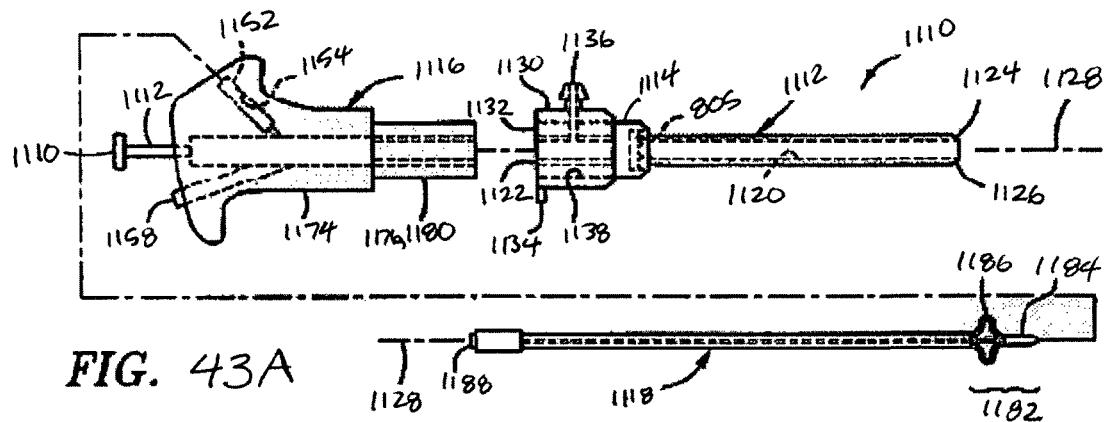
FIGS. 43A and 43B are side views of a second preferred embodiment of an apparatus for delivering a closure element, in accordance with the present invention.
Figure 43B:
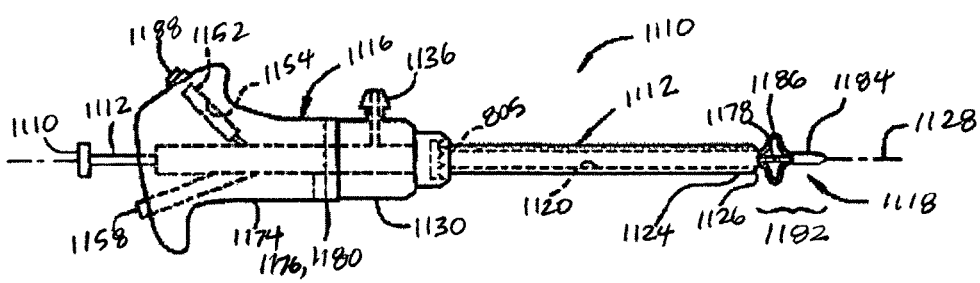

Alternatively, as shown in FIGS. 43A and 43B, an apparatus 1110 for delivering a closure element 805 may be provided that includes a separate obturator assembly 1118 that may be inserted into or otherwise connected to an actuator assembly 1116. For example, the actuator assembly 1116 may include a lateral port 1152 with an inner passage 1154 that communicates with an interior region or lumen (not shown) of actuator members 1176-1180 of the actuator assembly 1116.

At any time before advancing the carrier assembly 1114 to deploy the clip 805 thereon, the obturator assembly 1118 may be inserted into the lateral port 1152, thereby introducing a distal portion 1182 of the obturator assembly 1118 into the sheath 1112. An obturator housing 1181 of the obturator assembly 1118 may include one or more detents (not shown) for engaging complementary-shaped detents (also not shown) on the lateral port 1152. Thus, the obturator assembly 1118 may be substantially secured axially with respect to the lateral port 1152, and consequently relative to the actuator assembly 1116 and sheath 1112. Otherwise, the actuator and obturator assemblies 1116, 1118 may operate similar to the previous embodiment.

Turning to FIGS. 44A-44H, an apparatus 810 (the entire apparatus 810 is shown in FIGS. 44B-44F), such as that shown in FIG. 33, may be used to deliver a closure device, such as a clip 805, to close and/or seal an incision, puncture, or other opening. For example, the apparatus 810 may be used to deliver the clip 805 through a passage 892 that extends from a patient's skin 894, through intervening tissue 896, and into a wall 898 of a blood vessel 890. Alternatively, the apparatus 810 may be used to deliver other annular shaped devices (not shown) that may be disposed within the carrier assembly 814.

As shown in FIG. 44A, the sheath 812, without the actuator assembly 816 (not shown), may be inserted or otherwise positioned within the blood vessel 890, i.e., through the passage 892. The sheath 812 is preferably provided with the carrier assembly 814 in its proximal position, e.g., adjacent to or within the hub assembly 830. The sheath 812 may be advanced over a guide wire or other rail (not shown) previously positioned through the passage 892 into the blood vessel 890 using conventional procedures. Preferably, the blood vessel 890 is a peripheral vessel, such as a femoral or carotid artery, although other body lumens may be accessed using the sheath 812, as will be appreciated by those skilled in the art.

The passage 892, and consequently the sheath 812, may be oriented with respect to the vessel 890, thereby facilitating introduction of devices through the lumen 820 of the sheath 812 into the vessel 890 with minimal risk of damage to the vessel 890. One or more devices, such as a guide wire, a catheter, and the like (not shown), may be inserted through the sheath 812 and advanced to a desired location within the patient's body. For example, the devices may be used to perform a therapeutic or diagnostic procedure, such as angioplasty, atherectomy, stent implantation, and the like, within the patient's vasculature. After the procedure is complete, the device(s) may be removed from the sheath 812, and the actuator assembly 16 may be attached to the hub assembly 830 of the sheath 812.

Turning to FIG. 44B, along with FIGS. 39A, and 39B, the longitudinal slots 886-890 in the actuator members 876, 878, 880 may be aligned with the side port 836 extending from the hub assembly 830. This may align the "C" shaped cross-sections of the tubular members 876-880 with the spoke (not shown) extending across the passage 838. The distal portion 982 of the obturator assembly 18 may then be inserted into the lumen 820 of the sheath 812, and advanced towards the distal end 24 of the sheath 812. The actuator members 876, 878, 880 may also be inserted into the passage 838, thereby disposing the distal portion 982 in a predetermined rotational orientation relative to the sheath 812. Once the actuator members 876, 878, 880 are fully received in the passage 838, the connectors 834, 884 (not shown, see FIG. 33) may engage to secure the actuator assembly 816 to the hub assembly 830.

The carrier assembly 814 is also disposed at least partially within the passage 838 (not shown in FIGS. 39A and 39B) such that the tongues 850, 860, 870 on the carrier, pusher, and anchor members 840, 842, 844 are aligned with the side port 836. Consequently, the tongues 850, 860, 870 may be aligned with the longitudinal slots 886, 888, 890 in the actuator members 876, 878, 880 as the actuator members 876, 878, 880 are inserted into the passage 838.

Thus, as the actuator members 876, 878, 880 are advanced into the passage 838, the tongues 850, 860, 870 may be received in the longitudinal slots 886, 888, 890, preferably until the tabs 852, 862, 872 are received in the pockets 904, 906, 908, as best seen in FIG. 39B. The tongues 850, 860, 780 are preferably at least partially tapered, thereby self-aligning with the longitudinal slots 886, 888, 890, e.g., to correct any slight misalignment. With the tongues 850, 860, 870 engaged within the longitudinal slots 886, 888, 890, the carrier, pusher, and sheath members 840, 842, 844 may be coupled to the inner, intermediate, and outer tubular members 876, 878, 880, respectively. Thus, once the actuator assembly 816 is secured to the hub assembly 830, the distal portion 982 of the obturator assembly 16 is preferably disposed adjacent the distal end 824 of the sheath 812 within the lumen 820, as best seen in FIG. 44B.

Alternatively, for the apparatus 1110 shown in FIGS. 43A and 43B, the actuator assembly 1116 may be attached to the hub assembly 330 without the obturator assembly 1118. The obturator assembly 1118 may then be inserted into the lateral port 1152, through the interior of the actuator members 1176-1180, and into the lumen 1120 of the sheath 1112 at any time before deploying the clip 805. Thus, the distal portion 1182 of the obturator assembly 1118 may be disposed adjacent the distal end 1124 of the sheath 1112, similar to the actuator assembly 816.

Turning to FIG. 44C, the distal portion 982 of the obturator 818 may be advanced beyond the distal end 824 of the sheath 812, for example, by depressing the switch 988 on the actuator assembly 816. The distal tip 984 preferably is substantially soft and/or flexible such that the distal portion 982 substantially atraumatically enters the vessel 890. In this fully inserted position, cooperating detents (not shown), e.g., on the actuator housing 980 and the rail 972 of the actuator assembly 816, may be engaged to substantially secure the distal end 982 of the obturator 818 beyond the distal end 824 of the sheath 812.

Turning to FIG. 44D, the splines 986 may then be directed to their expanded configuration, for example, by further depressing the switch 988 on the actuator assembly 816. Preferably, the distal portion 982 is deployed and the splines are expanded in a single motion, e.g., by activating the switch 988. Alternatively, these steps may be performed independently from one another if desired.

Turning to FIG. 44E, the entire apparatus 810, including the sheath 812 and splines 986, may then be moved, e.g., by manipulating the actuator assembly 816. Preferably, the apparatus 810 is partially withdrawn from the vessel 890 until the splines 986 contact the wall 898 of the vessel 890, as shown. Thus, the splines 986 may provide a tactile indication of the position of the distal end 824 of the sheath 812 with respect to the wall 898 of the vessel 890. In addition, the splines 986 may assist in "presenting" the wall 898 of the vessel 890, e.g., for receiving the clip 805 (or other closure element) if the clip 805 is to engage the wall 898.

Turning to FIG. 44F, with the sheath 812 properly positioned, the carrier assembly 814 may be advanced along the sheath 812, i.e., into the passage 892 to deliver the clip 805. For example, a distal force may be applied to the knob 910, thereby advancing the actuator members 876, 878, 880 and consequently the carrier assembly 814 distally over the sheath 812. Because the actuator members 876, 878, 880 are all coupled together, as described above, the carrier assembly 814 advances with the outer sleeve 845 on the anchor member 844 substantially covering the clip 805. Because of the tapered configuration of the outer sleeve 845 and the carrier member 840, the carrier assembly 814 may be advanced through the passage 892 substantially atraumatically. In addition, because the clip 805 is substantially covered by the outer sleeve 845, the tissue surrounding the passage 892 may not be exposed to the tines 807 on the clip 805, which otherwise may inadvertently catch the tissue and damage the tissue and/or the clip 805. Further, the outer sleeve 845 may facilitate advancing the carrier assembly 814 through intervening layers of tissue, such as one or more layers of fascia (not shown) that may be encountered between the skin 894 and the wall 898 of the vessel 890.

When the carrier assembly 814 reaches a first distal position (FIG. 44F), the first set of cooperating detents (not shown, but described above with reference to FIGS. 40A and 40B) are disengaged to release the outer tubular member 880 with respect to the inner and intermediate tubular members 876, 878. The first beam 924 on the outer tubular member 880 may slidably engage the second ramp 922 on the housing 874, thereby disengaging the first tab 914 from the first pockets 916, 918. In addition, the outer tubular member 880 is preferably substantially secured at the first distal position, e.g., when the hole 926 in the first beam 924 interlocks a recess 928 in the second ramp 922 (as shown in FIG. 40B).

Figure 44G:
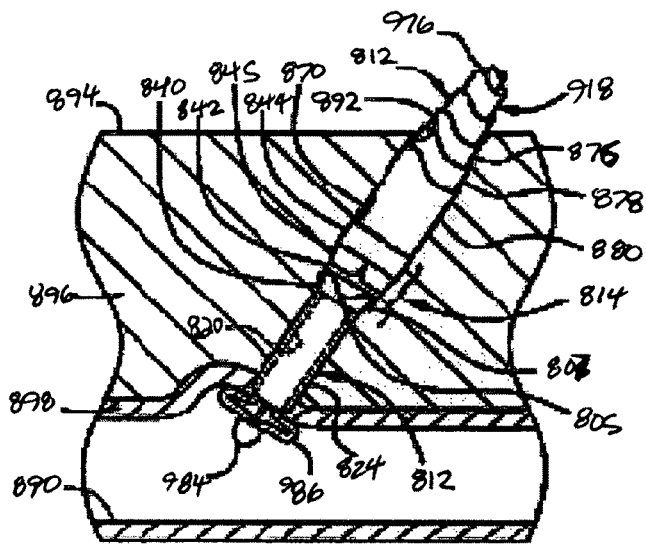

Turning to FIG. 44G, as the distal force continues to be applied to the knob 910 (not shown), the inner and intermediate tubular members 876, 880, and consequently the carrier and pusher members 840, 842, may be advanced further distally. As the carrier and pusher members 840, 842 are advanced relative to the outer sleeve 845, they may cause the outer sleeve 845 to expand to accommodate their advancing between the outer sleeve 845 and the sheath 812. To facilitate this advancement without tearing the outer sleeve 845, the outer sleeve 845 may include longitudinal slots, e.g., either straight slots 845a, as shown in FIG. 38C, or spiral slots 845a,' as shown in FIG. 38D. The slots 845a, 845a' may open as the carrier and pusher members 840, 842 are advanced, such that the outer sleeve 845 expands to assume a zigzag mesh configuration. In particular, the spiral slots 845a' may translate axial forces to torsional forces due to the spiral shape of the slots 845a,' e.g., such that the outer sleeve 845' twists as it expands, causing the surrounding tissue 896 to rotate about the longitudinal axis 828, thereby minimizing the tissue 896 being pushed distally as the carrier and pusher members 840, 842 are advanced through the tissue 896.

When the carrier and pusher members 840, 842 reach a second distal position, the second set of cooperating detents (not shown, but described above with reference to FIGS. 41A-41D) interact to release the intermediate tubular member 878 from the inner tubular member 876. For example, the transverse beam 940 may push the second tab 930 out of the second pocket 932 (as best seen in FIG. 41B). In addition, substantially simultaneously with this action, the second set of detents also preferably substantially secure the inner tubular member 876, e.g., by interlocking the transverse beam 940 in the wide portion 942b of slot 942.

Figure 44H:
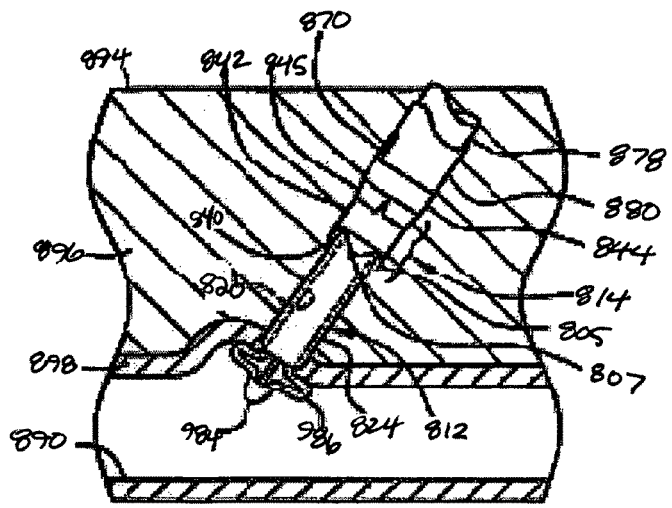

As shown in FIG. 44H, the intermediate tubular member 878 may then be advanced further distally by continuing to apply a distal force to the knob 910 (not shown). Thus, the pusher member 842 may be advanced distally relative to the carrier member 840, thereby forcing the clip 805 distally off the carrier member 840 and preferably into engagement with the wall 898 of the vessel 890 or other tissue surrounding the passage 892.

Figure 44I:
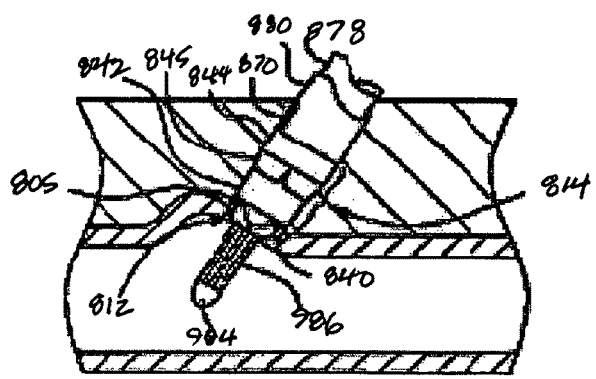
FIG. 44I is a cross-sectional view of the vessel of FIGS. 44A-44H, showing an alternative method wherein the clip is delivered into the wall of the vessel.

In a preferred method, shown in FIG. 44I, the splines 986 may automatically return to their collapsed configuration and/or may be retracted into the sheath 812 during deployment of the clip 805. For example, the splines 986 may be collapsed as the clip 805 is partially deployed from the carrier assembly 814, e.g., before the clip 805 is completely collapsed towards its closed position. The orientation of the clip 805 and the splines 986 about the longitudinal axis 828 may be such that tines 807 of the clip 805 are disposed between the splines 986 as the clip 805 is deployed. Thus, as the tines 807 are driven into the wall of the vessel 890, the tines 807 may avoid being driven into the splines 986. Embodiments of a clip and delivery apparatus that provide such an orientation are disclosed in incorporated U.S. Pat. No. 6,197,042.

For example, as the intermediate tubular member 878 is advanced to a third position beyond the second distal position, it may release the lock in the obturator housing 980, thereby causing the splines 986 to collapse and/or the distal portion 982 to retract into the sheath 812. Alternatively, the splines 986 may be collapsed before the clip 805 is ejected completely from off of the carrier member 840, or even before the pusher member 842 begins to deploy the clip 805. This may avoid any risk of contact between the clip 805 and the splines 986.

The relative lengths of the actuator members 876, 878, 880 and the sheath 812 and/or the length of the longitudinal slots 886, 888, 890 may be set such that the second distal position is at a region proximal to the wall 898 of the vessel 890. For example, as shown in FIG. 44H, it may be desirable to deploy the clip 805 within intervening tissue between the patient's skin and the wall 898 of the vessel 890. Alternatively, as shown in FIG. 44I, the clip 805 may be deployed such that the tines 807 are driven into or through the wall 898 of the vessel 890.

Once the clip 805 is successfully delivered, the apparatus 810 may be withdrawn from the passage 892. If the splines 864 of the locator member 814 are not automatically collapsed during advancement of the housing 824, the splines 864 may be affirmatively collapsed, e.g., by depressing the switch 988. The entire apparatus 810 may then be removed in one step. Alternatively, as in the embodiment of FIGS. 43A and 43B, if the obturator assembly 1118 is separable from the actuator assembly 1116, it may be withdrawn from the sheath 812 before withdrawing the actuator assembly 1116 and/or sheath 1112.

Thus, the clip 805 remains in place within the wall 898 of the vessel 890 or in the surrounding tissue 896 adjacent the vessel 890 to close and/or seal the passage 892. The clip 805 may remain substantially permanently in the patient's body. Alternatively, the clip 805 may be formed from bioabsorbable material, and may remain until the passage 892 is at least partially healed and the clip 805 is absorbed by the surrounding tissue 896.

VII. Sixth Closure System Embodiment

Turning to FIGS. 45A-46B, another preferred embodiment of an apparatus 1210 is shown for sealing a passage through tissue communicating with a body lumen, such as a blood vessel, in accordance with the present invention. Generally, the apparatus 1210 includes a plug member 1212, an elongate shaft or handle device 1214, and a locator member 1216.

Figure 45A:
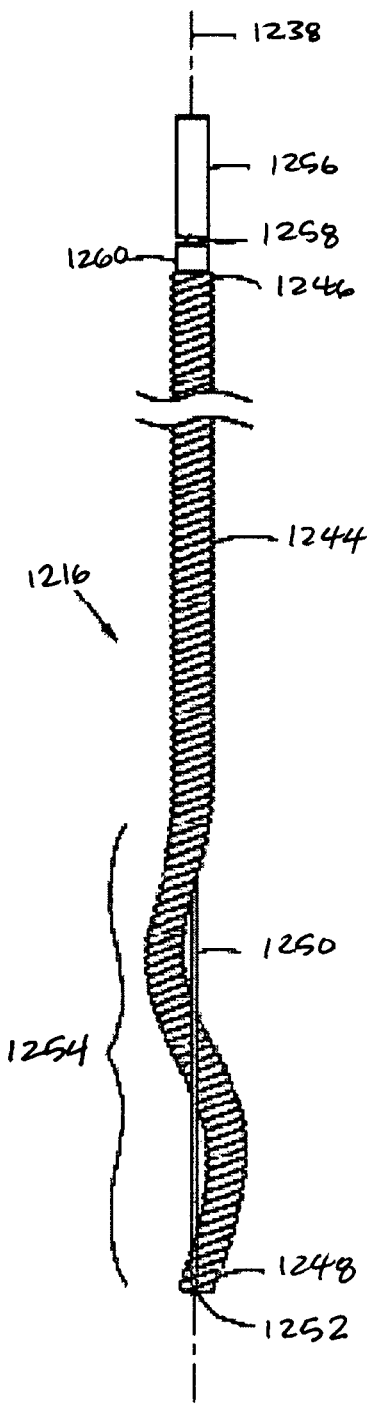
FIGS. 45A and 45B are side views of another preferred embodiment of a locator device, in accordance with the present invention.
Figure 45B:
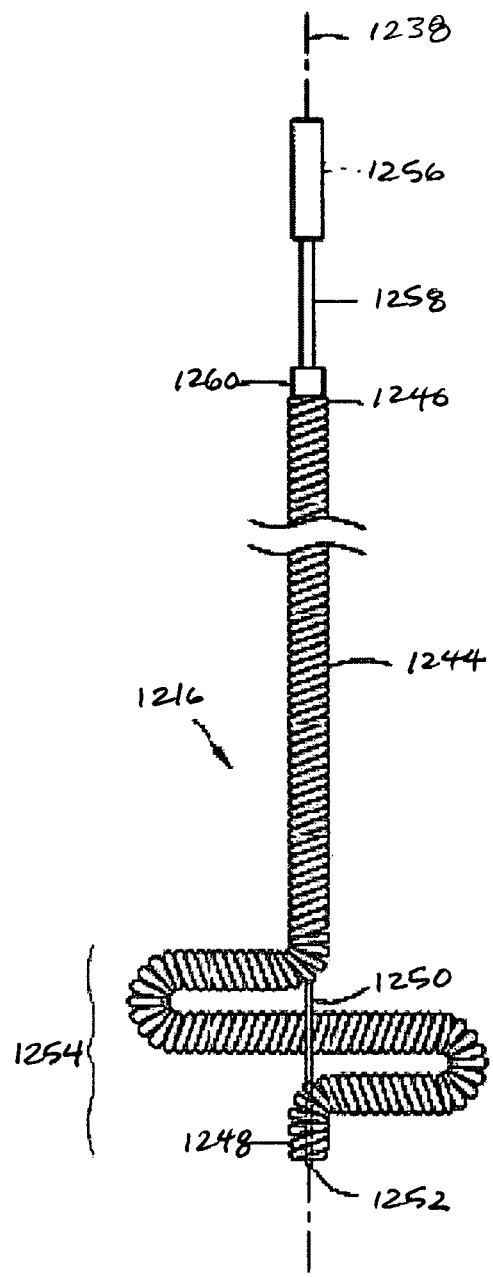

With particular reference to FIGS. 45A and 45B, the locator member 1216 includes a helically wound wire 1244 that includes proximal and distal ends 1246, 1248, defining a longitudinal axis 1238 therebetween. The helically wound wire 1244 may be formed from flexible material that is biased to assume an axial configuration, as shown in FIG. 45A, but may be deflectable, e.g., by buckling, as explained further below. The helically wound wire 1244 has a diameter such that the locator member 1216 may be advanced through a lumen 1240 of the handle device 1214 (as shown in FIGS. 46A and 46B) and/or directly into a passage through tissue. Preferably, adjacent turns of the helically wound wire 1244 are in close proximity to or substantially abut one another in a relaxed state free from external forces, yet may be slidable and/or bendable with respect to one another to facilitate buckling of the locator member 1216. Alternatively, adjacent turns of the helically wound wire 1244 may have spaces between them in the relaxed state.

In a further alternative, the helically wound wire 1244 may extend only partially from the distal end 1248 towards the proximal end 1246 (not shown). In this alternative, the locator member 1216 may include a substantially straight wire, tubular body, or other proximal portion (not shown) that may extend from the helically wound wire to the proximal end 1246 of the locator member 1216. The proximal portion may be relatively more rigid, e.g., resistant to buckling than the helically wound wire and/or may be supported by the wall of the lumen 1240 of the handle device 1214.

The locator member 1216 also includes a tether or other control element 1250 that is coupled to the helically wound wire 1244. Preferably, the tether 1250 is an elongate wire, ribbon, cable, and the like that has a distal end 1252 that is coupled to the distal end 1248 of the helically wound wire 1244. The tether 1250 may include a handle 1256 on its proximal end 1258 for selectively pulling the tether 1250 in a proximal direction to cause the helically wound wire 1244 wire to buckle, as explained further below.

The tether 1250 may extend along an outer surface of the helically wound wire 1244 at least partially from the distal end 1248 towards the proximal end 1246, thereby defining a deflectable distal portion 1254. For example, the tether 1250 may extend along the outer surface of the helically wound wire 1244 along its entire length. Alternatively, the tether 1250 may extend along the outer surface of the distal portion 1254, and then may pass between turns of the helically wound wire 1244, and extend within the helically wound wire 1244 to the proximal end 1246 of the locator member 1216. In a further alternative, the tether 1250 may extend its entire length within the helically wound wire 1244. For example, if the helically wound wire 1244 has gaps between adjacent turns, the helically wound wire 1244 may be compressed when the tether 1250 is pulled to cause the helically wound wire 1244 to buckle.

An actuator (not shown) may be provided on the proximal end 1246 of the locator member 1216. The actuator may be coupled to the proximal end 1258 of the tether 1250 and to the helically wound wire 1244 for providing controlled relative movement of the tether 1250 and the helically wound wire 1244, as will be appreciated by those skilled in the art.

When the proximal end of the tether 1250 is in its distal-most position, the helically wound wire 1244 may extend generally parallel to the longitudinal axis 1238, thereby defining an axial or inactivated configuration, such as that shown in FIG. 45A. Even if the distal portion of the helically wound wire 1248 becomes slightly curved, e.g., when inserted into a body lumen, the distal portion is still considered "generally parallel" to the longitudinal axis 1238. When the tether 1250 is directed proximally, e.g., by applying a proximal force on the proximal end 1258 and/or handle 1256, it may pull the distal end 1248 of the helically would wire 1244 towards the proximal end 1246, thereby causing the distal portion 1254 of the helically wound wire 1244 to buckle, thereby assuming a transverse or activated configuration, such as that shown in FIG. 45B.

Turning to FIGS. 46A and 46B, the plug member 1212 is a body, preferably having a generally cylindrical shape, including a proximal end 1220, a distal end 1222, and an outer surface 1230. The plug member 1212 includes a lumen 1224 that extends between a proximal opening 1226 and a distal opening or port 1228. The plug member 1212 may be formed from biocompatible material, and preferably from bioabsorbable material, and/or may be substantially rigid or partially flexible.

The plug member 1212 generally includes a helical thread pattern 1218, including one or more helical threads, that extends at least partially between its proximal and distal ends 1220, 1222. The helical thread pattern 1218 is preferably substantially rigid and may have a substantially square cross-section to facilitate sealing of a passage into which the plug member 1212 is threaded.

A sealing member (not shown) may be provided within the lumen 1224 for substantially sealing the lumen 1224 from fluid flow therethrough. The sealing member is preferably formed from a material that expands when exposed to fluids, e.g., a gel foam, and may be bioabsorbable, e.g., if the plug member 1214 is. Before exposure to fluid, the sealing member may be substantially recessed from the lumen 1224, thereby accommodating inserting devices therethrough. Upon exposure to fluid, e.g., blood, the sealing member may expand, e.g., due to hydration and the like, across the lumen 1224 and/or otherwise substantially seal the lumen 1224.

Alternatively, the sealing member may be a valve (not shown) or a coil of material that is biased to substantially seal the lumen 1224 from fluid flow. For example, the sealing member may be biased to substantially seal the lumen 1224, yet may be deflected to accommodate insertion of one or more devices therethrough. In a further alternative, the lumen 1224 may have a relatively small cross-section, and the sealing member may be omitted.

Additional information regarding plug members appropriate for use with the present invention may be found in U.S. Pat. No. 5,292,332 to Lee and U.S. Pat. No. 5,290,310 to Makower et al., the disclosures of which are expressly incorporated herein by reference.

Returning to FIGS. 46A and 46B, the handle device 1214 has a proximal end 1234, a distal end 1236, and a lumen 1240 that extends between the proximal and distal ends 1234, 1236, e.g., for accommodating insertion of the locator member 1216 and/or other devices therethrough. A handle 1242 may be provided on the proximal end 1234 of the shaft 1214 for facilitating manipulation of the apparatus 1210, e.g., to facilitate rotation of the apparatus 1210 into a passage, as described below. Preferably, the handle device 1214 is a substantially rigid tubular member having a cross-section that is substantially smaller than a cross-section of the plug member 1212, e.g., to minimize dilation of a passage into which the plug member 1212 is inserted.

The plug member 1212 and the distal end 1236 of the handle device 1214 generally include one or more connectors (not shown) for releasably securing the plug member 1212 to the handle device 1214, as described in application U.S. Pat. No. 6,780,197, which is incorporated herein by reference. Preferably, cooperating connectors (not shown) substantially couple the plug member 1212 to the handle device 1214 such that the plug member 1212 cannot move independently of the handle device 1214, e.g., such that the plug member 1212 may be rotated only by rotating the handle device 1214. Preferably, the handle 1242 includes an actuator (not shown) that may be activated to release the connectors securing the plug member 1212 to the handle device 1214.

When the locator member 1216 is fully inserted into the handle device 1214, the distal portion 1254 of the locator member 1216, is preferably disposed beyond the distal end 1236 of the handle device 1214, and, more preferably, beyond the distal end 1222 of the plug member 1212, as shown in FIG. 46B. The locator member 1216 may be coupled to the handle device 1214, e.g., by cooperating detents or other connectors on their respective proximal ends 1246, 1234. All of the distal portion 1254 of the locator member 1216 may be disposed beyond the distal end 1222 of the plug member 1212, or a portion of the distal portion 1254 may extend into the lumen 1224 of the plug member and/or the lumen 1240 of the handle device 1214.

Figure 47A:
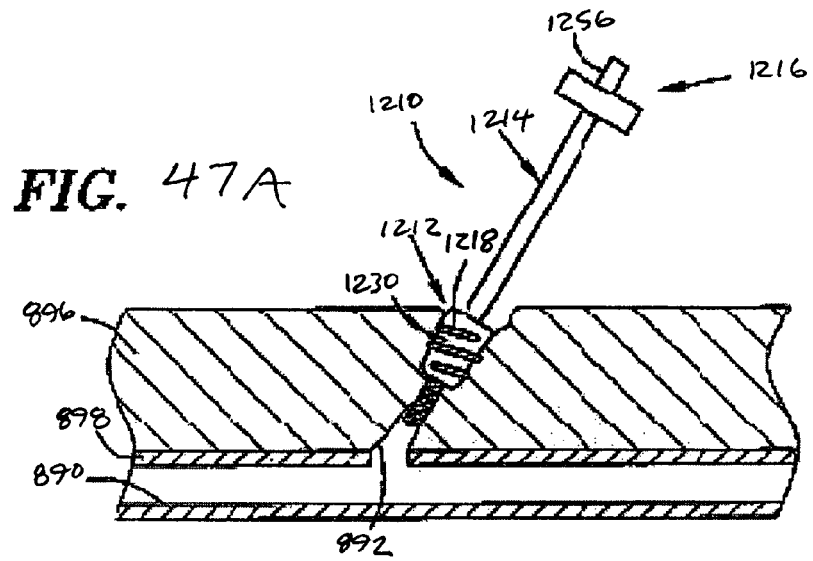
FIGS. 47A-47D are cross-sectional side views, showing a method for delivering a plug member using the apparatus of FIGS. 46A and 46B.
Figure 47B:
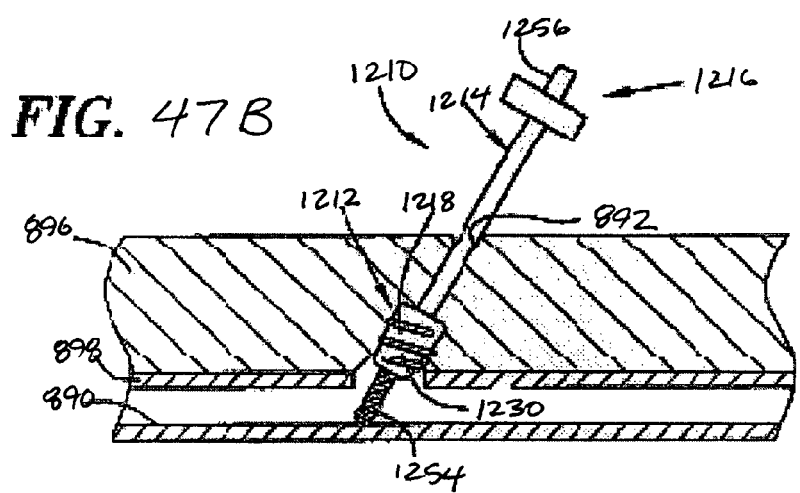

Turning to FIGS. 47A-47D, during use, the apparatus 1210 may be used to seal and/or close a passage through tissue 896, such as a puncture 892 communicating with a blood vessel 890 or other body lumen. Initially, the plug member 1212 may be connected to or otherwise disposed on the handle device 1214. The locator device 1216 may be inserted into the handle device 1214 until the distal portion 1254 extends beyond the plug member 1212, as shown in FIG. 46B (but with the distal portion 1254 in its axial configuration as shown in FIGS. 47A and 47B).

The puncture 892 may be used to provide percutaneous access to the vessel 890. For example, the puncture 892 may facilitate performing an endovascular procedure within a patient's vasculature, such as angioplasty, stenting, atherectomy, and the like, or may otherwise provide access via the vessel 890 to a region within the patient's body. Upon completion of the procedure, any instruments, such as an introducer sheath (not shown), may be removed from the vessel 890 and puncture 892.

The apparatus 1210 may then be introduced into the puncture 892, for example, by initially inserting the distal portion 1254 of the locator member 1216 into the puncture 892. The distal portion 1254 may have a substantially atraumatic distal tip, e.g., tapered and/or relatively flexible, to facilitate advancement of the apparatus 1210 into the puncture 892. As the distal portion 1254 of the locator member 1216 is advanced into the puncture 892, the plug member 1212 may be inserted into the puncture 892, as shown in FIG. 47A.

Because of the thread pattern 1218, the handle device 1214 may be rotated in a first direction to thread the plug member 1212 into the puncture 892. Consequently, the outer surface 1230 and/or the thread pattern 1218 may engage tissue 896 surrounding the puncture 892, thereby substantially sealing the puncture 892 from fluid flow, such as blood flow, within the vessel 890. The apparatus 1210 may be rotated in the first direction about its longitudinal axis 1238 to thread the plug member 1212 substantially atraumatically deeper into the puncture 892.

Turning to FIG. 47B, as the plug member 1212 is advanced, the distal portion 1254 of the locator device 1216 eventually passes through the wall 898 of the vessel 890. This advancement may be monitored by providing one or more radiopaque markers (not shown) and the like on the handle device 1214, the plug member 1212, and/or the locator member 1216, and using fluoroscopy while advancing the apparatus 1210. Alternatively, depth markers (not shown) may be provided on the exterior of the handle device 1214 for visual monitoring advancement. Tactile indication, e.g., resistance to further advancement, may also identify that the vessel 890 has been attained.

Figure 47C:
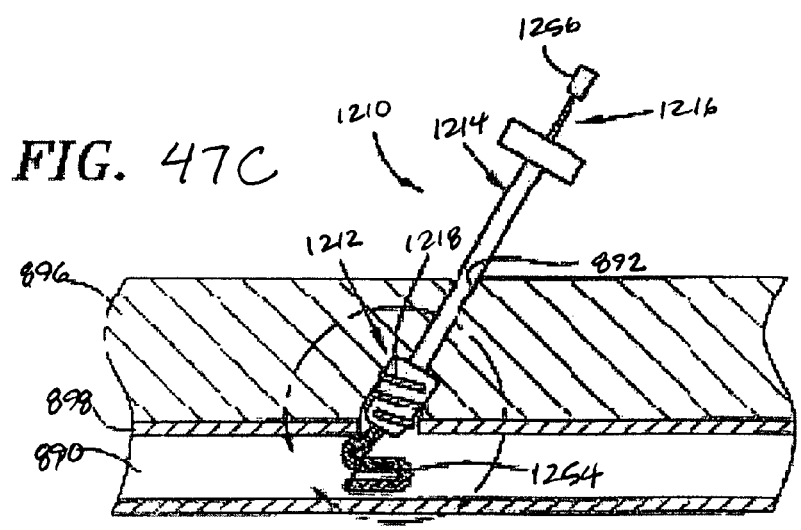
Figure 47D:
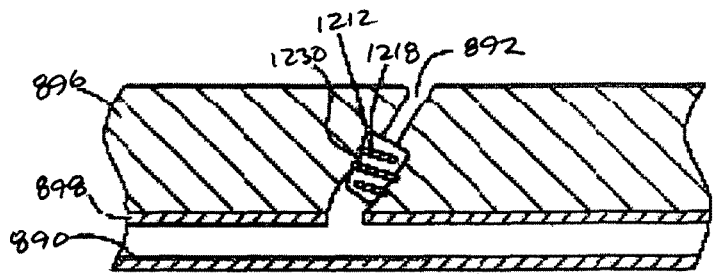
Figure 48:
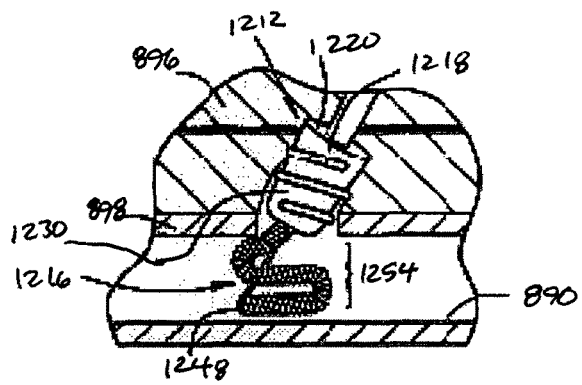
FIG. 48 is a detail of FIG. 47C, showing activation of the locator member with a blood vessel.

Once it is confirmed that the distal portion 1254 is located within the lumen 890, the locator member 1216 may be activated, e.g., by pulling the handle 1256 proximally or activating an actuator (not shown) at the proximal end of the locator member 1216. This causes the distal portion 1254 to buckle to its transverse configuration, as shown in FIG. 47C. In the transverse configuration, the distal portion 454 has a cross-section such that the distal portion 454 may not be withdrawn into the plug member 1212 and/or the puncture 892.

Rotation of the apparatus 1210 may then be reversed, i.e., in a second direction opposite the first direction, to withdraw the plug member 1212 a predetermined distance relative to the vessel 890. As the plug member 1212 is withdrawn, the distal portion 1254 of the locator member 1216 may engage a wall 898 of the vessel 890, thereby creating resistance to further rotation. This may provide tactile feedback that the plug member 1212 is disposed at a desired location, e.g., within the puncture 892 in close proximity to the vessel 890, but not extended into the vessel 890.

The plug member 1212 may then be released from the handle device 1214. The locator member 1216 may be deactivated, i.e., returned to its axial configuration, and then withdrawn from the plug member 1212, either simultaneously with withdrawal of the handle device 1214 or before withdrawal of the handle device 1214. The sealing member (not shown) preferably substantially seals the lumen 1224 (not shown, see FIGS. 46A and 46B) within the plug member 1212 to prevent fluid within the vessel 890 from passing therethrough to leak from the puncture 892. Alternatively, leakage through the lumen 1224 may be sufficiently insignificant, e.g., hemostatis may occur rapidly despite the presence of the lumen 1224, and the sealing member may be eliminated.

Preferably, as explained above, the sealing member is a material that expands when exposed to fluid. For example, as the locator member 1216 is withdrawn (either before or along with the handle device 1214), fluid, e.g., blood, may flow proximally through the lumen 1224 in the plug member 1212, e.g., until it encounters the sealing member. Although a relatively small amount of fluid may pass beyond the sealing member, the sealing member may expand substantially due to the fluid contact until it substantially seals the lumen. Alternatively, the sealing member may be a valve that may open to accommodate the locator member 1216, but may automatically close upon withdrawal of the locator member 1216.

If the plug member 1212 is bioabsorbable, it may remain within the puncture 892 as the tissue heals, thereby allowing the wall 898 of the vessel 890 and tissue 896 surrounding the passage 892 to at least partially heal before the plug member 1212 is absorbed. Alternatively, the plug member 1212 may be retrieved once the tissue between the plug member 1212 and the vessel 890 has substantially healed.

In an alternative embodiment, a guidewire (not shown) may be used during the procedure. The apparatus 1210 may be provided initially without the locator member 416, and the guidewire may be backloaded through the plug member 1212 and handle device 1214. The guidewire may be used to guide the plug member 1212 as it is threaded through the puncture 892 until it at least partially enters the vessel 890. Once the vessel 890 has been attained, the guidewire may be withdrawn, and the locator member 1216 may be inserted through the handle device 1214 until the distal portion 1254 extends beyond the plug member 1212 into the vessel 890. The distal portion 1254 may be activated, and then the procedure may proceed substantially as just described to deliver the plug member 1212.

In a further alternative, the locator member 1214 shown in FIGS. 45A and 45B may be used to position and/or deliver other closure elements. For example, the locator member 1214 may be substituted for the locator member with expandable positioning elements to deliver a clip within a housing that is slidable along a sheath (not shown) through which the locator member 1216 may be inserted. In yet another alternative, the locator member with expandable positioning elements shown and described above in connection with FIGS. 33-35B may be used in place of the locator member 1216 to position and/or deliver the plug member 1212, using methods similar to those described above.

Turning to FIGS. 49A-49D, an apparatus 1210 may be used in conjunction with an introducer sheath 1202 or other tubular member already in place within the passage 892. For example, the introducer sheath 1202 may be used to access the vessel 890 to perform a procedure within the patient's vasculature or elsewhere within the patient's body, as described above. The sheath 1202 may be disposed such that a proximal end 1204 is located outside the passage 892, and a distal end 1206 is located within the vessel 890.

Figure 49A:
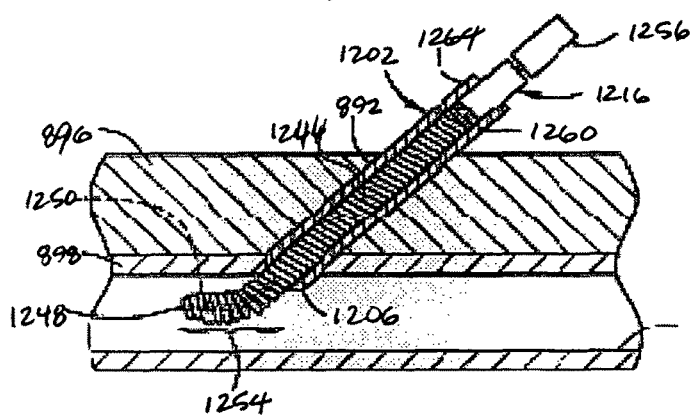
FIGS. 49A-49D are cross-sectional side views, showing another method for delivering a plug member using the apparatus of FIGS. 44A and 44B.
Figure 49B:
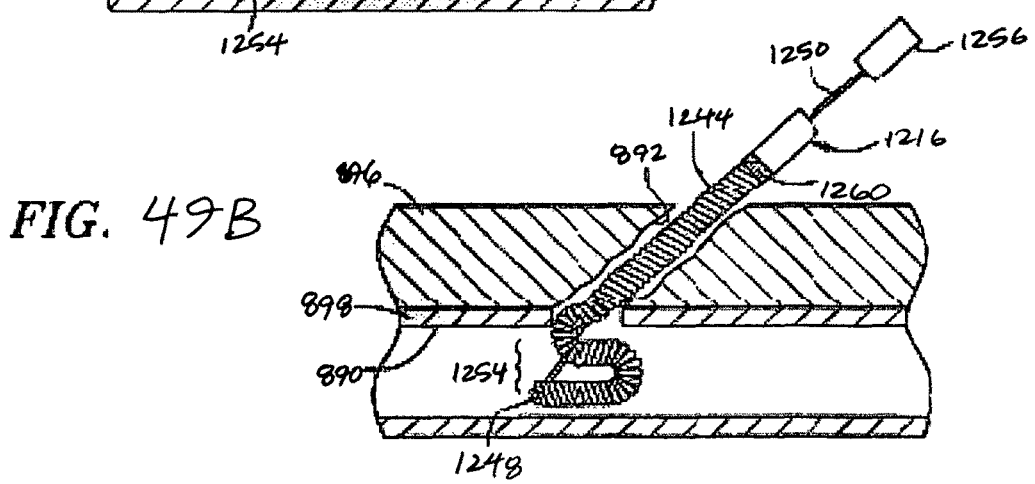
Figure 49C:
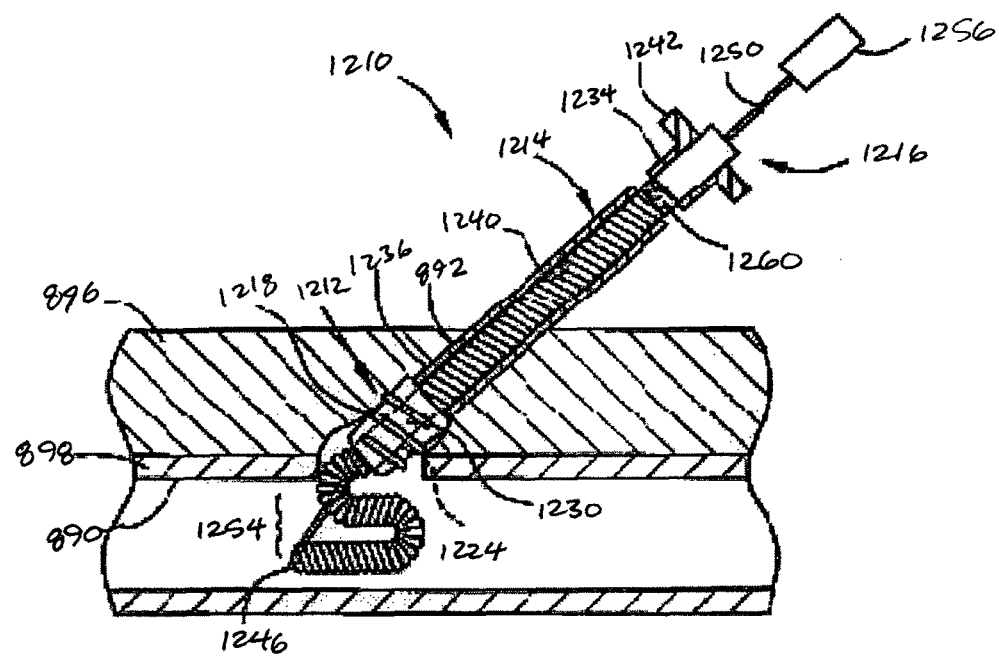
Figure 49D:
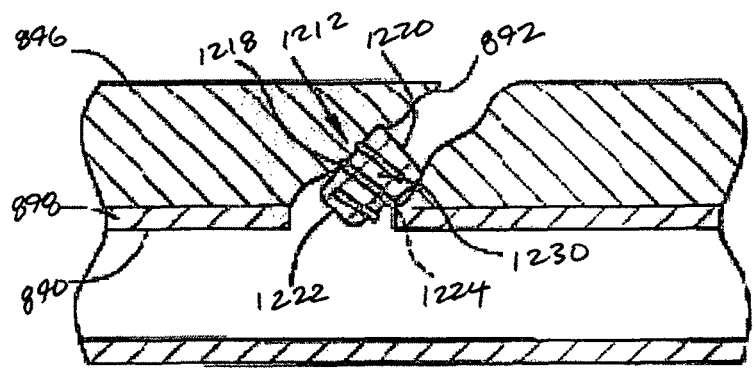

As shown in FIG. 49A, the locator member 1216 may be inserted through the introducer sheath 1202 until the distal portion 1254 extends beyond the distal end 1206 of the sheath 1202 into the vessel 890. The distal portion 1254 may be buckled from the axial configuration to the transverse configuration, as described above, and then the locator member 1216 may be manipulated, e.g., pulled proximally, such that the buckled distal portion 1254 engages or otherwise contacts a proximal wall 892 of the vessel 890. Thus, the locator member 1216 may be secured from proximal movement relative to the vessel 890 and/or may provide tactile feedback of the location of the distal portion 1216. The sheath 1202 may be removed from the passage 892 either before or after buckling the distal portion 1254 of the locator member 1216.

The plug member 1212 may then be advanced over the locator 1216 member into the passage 892. For example, the plug member 1212, disposed on the distal end 1236 of an elongate member 1214, may be threaded through the tissue 896 along the passage 892 such that threads 1218 on the plug member 1212 substantially engage the surrounding tissue 896. The locator member 1216 may pass through a passage 1224 in the plug member 1212 and/or through the lumen 1240 of the elongate member 1214. Once the plug member 1212 reaches a desired location within the passage 892, the plug member 1212 may be released from the distal end 1236 of the elongate member 1214.

To facilitate positioning of the plug member 1212 relative to the vessel 890, the locator member 1216 and/or the elongate member 1214 may include one or more depth markers. For example, the locator member 1216 may include a marker band 1260 at a predetermined location relative to the distal portion 1254. The elongate member 1214 may include a window 1262 or other opening at a predetermined location on its proximal end 1234. When the marker band 1260 on the locator member 1216 appears in the window 1262, it may provide a visual indication that the plug 1212 is disposed at a predetermined position relative to the wall 898 of the vessel 890. Alternatively, the locator member 1216 and the elongate member 1214 may include other cooperating elements, e.g., cooperating tactile elements as described above, for identifying when the plug 1212 is disposed at a predetermined location.

After the plug 1212 is released from the elongate member 1214, the distal portion 1254 of the locator member 1216 may be returned to its axial configuration, and the elongate member 1214 and the locator member 1216 may be withdrawn from the passage 892, leaving the plug member 1212 to substantially seal the passage 892, similar the embodiments described above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of closing an opening in a body tissue, the method comprising:
   elastically deforming an elastically deformable closure clip into a first closure clip position;
   positioning the elastically deformed closure clip adjacent to the opening in the body tissue such that a plurality of spikes extending from an annular portion of the elastically deformed closure clip are insertable into the tissue at a location outward from a central axis of the opening, the annular portion including a plurality of upper members and a plurality of lower members, the plurality of upper members and the plurality of lower members being curved and concentric about a longitudinal axis extending through the plurality of upper members and the plurality of lower members, each upper member being separated from two adjacently positioned lower members by a pair of legs, the plurality of spikes extending from the plurality of lower members and including at least a pair of oppositely disposed spikes that are elastically separated from one another in the first closure clip position;
   inserting the plurality of spikes into the tissue at a location outward from the central axis with the opening; and
   positioning the elastically deformed closure clip, with the annular portion, in a second closure clip position such that the plurality of spikes extending from the annular portion are elastically pulled inward toward the central axis of the opening so as to pull the tissue between the opening and each of the spikes together causing the oppositely disposed spikes to cross over one another in the second closure clip position and close the opening.

2. The method as in claim 1, further comprising releasing the elastically deformed closure clip from a distal end of a closure clip applicator when adjacent to the opening in the tissue.

3. The method as in claim 2, further comprising positioning the closure clip applicator adjacent to the opening in the body tissue using a sheath.

4. The method as in claim 3, wherein the sheath guides the positioning of the closure clip applicator so that the plurality of spikes are capable of being inserted into the tissue at the location outward from the central axis of the opening.

5. The method as in claim 4, further comprising positioning the sheath relative to the opening in the tissue using a guide.

6. The method as in claim 5, wherein the guide has a distal portion that extends through the opening of the body tissue and a proximal portion that is disposed within a lumen of the sheath during the positioning of the sheath.

7. The method as in claim 6, further comprising centering the sheath at the central axis of the opening using the guide.

8. The method as in claim 7, further comprising centering, with the sheath, the spikes of the closure clip around the opening of the tissue with respect to the central axis when the closure clip is in the second position.

9. A method of closing an opening in a body tissue, the method comprising:
   radially elastically expanding an elastically deformable closure clip into a radially elastically expanded first closure clip delivery position;
   positioning a closure clip applicator adjacent to the opening in the body tissue, the closure clip applicator supporting the radially elastically expanded closure clip at a distal end of the closure clip applicator, the radially elastically closure clip having an annular portion, the annular portion including a plurality of upper members and a plurality of lower members, the plurality of upper members and the plurality of lower members being curved and concentric about a longitudinal axis extending through the plurality of upper members and the plurality of lower members, each upper member being separated from two adjacently positioned lower members by a pair of legs, a plurality of spikes extending from each lower member toward the longitudinal axis;
   positioning the radially elastically expanded closure clip into the radially elastically expanded first closure clip delivery position adjacent to the opening in the body tissue such that the plurality of spikes extending from the annular portion of the elastic closure clip are inserted into the tissue at a location outward from a central axis of the opening, the plurality of spikes, extending from the plurality of lower members, including at least a pair of oppositely disposed spikes that are separated from one another in the radially elastically expanded first closure clip delivery position; and
   elastically contracting the radially elastically expanded closure clip to a radially elastically contracted second closure clip deployed position such that the plurality of spikes extending from the annular portion are elastically pulled inward toward to central axis of the opening so as to pull the tissue between the opening and each of the spikes together causing the oppositely disposed spikes to cross over one another in the radially elastically contracted second closure clip deployed position and close the opening.

10. The method as in claim 9, further comprising releasing the closure clip from a distal end of the closure clip applicator when adjacent to the opening in the tissue, wherein the elastic closure clip is formed of a superelastic material.

11. The method as in claim 10, further comprising positioning the closure clip applicator adjacent to the opening in the body tissue using a sheath.

12. The method as in claim 11, further comprising positioning the sheath relative to the opening in the tissue using a guide.

13. The method as in claim 12, wherein the guide has a distal portion that extends through the opening of the body tissue and a proximal portion that is disposed within a lumen of the sheath.

14. The method as in claim 13, further comprising centering the sheath at the central axis of the opening by using the guide.

15. The method as in claim 14, further comprising centering, with the sheath, the spikes of the closure clip around the opening of the tissue with respect to the central axis when the closure clip is in the second position.

16. A method of closing an opening in a body tissue, the method comprising:
   inserting a guide through the opening in the body tissue;
   using the guide to position a closure clip applicator adjacent to the opening in the body tissue with the guide, the closure clip applicator having an elastic closure clip in a radially elastically expanded first closure clip delivery position at a distal end of the closure clip applicator, the elastic closure clip having an annular portion, the annular portion including a plurality of upper members and a plurality of lower members, the plurality of upper members and the plurality of lower members being curved and concentric about a longitudinal axis extending through the plurality of upper members and the plurality of lower members, each upper member being separated from two adjacently positioned lower members by a pair of legs, a plurality of spikes extending from each lower member toward the longitudinal axis;

positioning the radially elastically expanded closure clip into the radially elastically expanded first closure clip delivery position adjacent to the opening in the body tissue such that the plurality of spikes extending from the annular portion of the elastic closure clip are inserted into the tissue at a location outward from a central axis of the guide, the plurality of sharpened, tissue-penetrating spikes, extending from the plurality of lower members, including at least a pair of oppositely disposed spikes that are separated from one another in the radially elastically expanded first closure clip delivery position; and elastically contracting the radially elastically expanded closure clip to a radially elastically contracted second closure clip deployed position such that the plurality of spikes extending from the annular portion are pulled inward toward to central axis of the guide so as to pull the tissue between the opening and each of the spike together causing the oppositely disposed spikes to cross over one another in the radially elastically contracted second closure clip deployed position and close the opening.

17. The method as in claim 16, further comprising releasing the closure clip from a distal end of the closure clip applicator when adjacent to the opening in the tissue, wherein the elastic closure clip is formed of a superelastic material.

18. The method as in claim 17, further comprising positioning the closure clip applicator adjacent to the opening in the body tissue using a sheath.

19. The method as in claim 18, wherein the guide has a distal portion that extends through the opening of the body tissue and a proximal portion that is disposed within a lumen of the sheath before the clip contracts the opening in the body tissue.

20. The method as in claim 17, further comprising centering, with the sheath, the spikes of the closure clip around the opening of the tissue with respect to the central axis when the closure clip is in the second position.

21. The method as in claim 1, wherein the annular portion of the elastically deformed closure clip forms a lumen.

22. The method as in claim 1, wherein the bodily tissue is an outer wall of a blood vessel.

23. The method as in claim 1, wherein the plurality of spikes comprise four spikes.

24. The method as in claim 1, wherein the plurality of spikes comprise barbed spikes.

* * * * *